US006783952B1

(12) United States Patent
Brown et al.

(10) Patent No.: US 6,783,952 B1
(45) Date of Patent: Aug. 31, 2004

(54) SECRETED SOLUBLE α2δ-2, α2δ-3 OR α2δ-4 CALCIUM CHANNEL SUBUNIT POLYPEPTIDES AND SCREENING ASSAYS USING SAME

(75) Inventors: Jason Peter Brown, Stapleford (GB); François Bertelli, Royston (GB)

(73) Assignee: Warner-Lambert Company, Morris Plains, NJ (US)

( * ) Notice: Subject to any disclaimer, the term of this patent is extended or adjusted under 35 U.S.C. 154(b) by 0 days.

(21) Appl. No.: 09/397,550

(22) Filed: Sep. 16, 1999

(51) Int. Cl.[7] ........................ C12N 15/12; C12N 15/63; C12N 15/00; C07K 14/00; C07H 21/04

(52) U.S. Cl. ....................... 435/69.1; 435/6; 435/320.1; 435/325; 530/350; 536/23.5

(58) Field of Search ........................ 435/69.1, 6, 320.1, 435/325; 530/350; 536/23.5

(56) References Cited

U.S. PATENT DOCUMENTS 5,429,921 A 7/1995 Harpold et al. ................ 435/4
5,846,757 A 12/1998 Harpold et al. ............... 435/29
6,441,156 B1 * 8/2002 Lerman et al. ............ 536/23.5

FOREIGN PATENT DOCUMENTS

WO 93/04083 3/1993
WO WO-9504822 A1 * 2/1995
WO 0020450 4/2000

OTHER PUBLICATIONS

Mikayama T. Molecular cloning and functional expression of a cDNA encoding glycosylation–inhibiting factor. Proc. Natl. Acad. Sci. USA vol. 90, pp. 10056–10060, 1993.*

Voet et al. Biochemistry. 1990. John Wiley & Sons. Inc., pp. 126–128 and 228–234.*

Gee, N.S., et al., The Journal of Biological Chemsitry, The Novel Anticonvulsant Drug Gabapentin (Neurontin), Binds to the δ2δSubunit of a Calcium Channel, 1996, vol. 271:10, pp. 5768–5776.

Brown, J.P., et al., The Journal of Biological Chemsitry, "Cloning and Delection Mutagenesis of the α2δCalcium Channel Subunit From Procine Cerebral Cortex", 1998, vol. 273:39, pp. 25458–25465.

Kowalski, M.T., et al. Biological Society Transactions, "Effects of Anti–Calcium Channel A2–subunit Antibodies on Calcium Flux and 1,4–Dihydropyridine Binding" 1990, p. 890.

Gurnett, C.A. et al. The J. of Biological Chemsitry. "Extracellular Interaction of the Voltage–Dependent CA2+ Channel α2δand α1 Subunits", 1997, 272:29 pp 18508–18512.

Gurnett, C.A., et al. Neuron "Dual function of the Voltage–Dependent CA2+ Channel α2δSubunit in Current Stimulation and Subunit Interaction" 1996, vol. 16, pp. 431–440.

Felix, R. et al. J. of Neuroscience, "Dissection of Functional Domains of the Voltage–Dependent CA2+ Channel α2δSubunit", 1997, vol. 17:18, pp. 6884–6891.

Field, M. J., et al., British Journal of Pharmacology, "Gabapentin (Neurontin) and S–(+)–3–Isobutylgaba Represent a Novel Class of Selective Antihyperalgesisc Agents", 1997, vol. 121, pp. 1513–1522.

Klubauer, N., et al., The Journal of Neuroscience, "Molecular Diversity of the Calcium Channel α2δSubunit", 1999, vol. 19:2, pp. 684–691.

Tokumaru, H., et al., European Journal of Pharmacology–Molecular Pharmacology Section. "Purification of the Cardiac 1,4–Dihydropyridine Receptor using Immunoaffinity Chromatography with a Monoclonal Antibody Against the α2δSubunit of the Skeletal Muscle Dihydropyridine Receptor" 1992, vol. 227, pp. 363–370.

Hill, D.R., et al., European Journal of Pharamocology–Molecular Pharmacology Section, "Locationizaiton of [3H] Gabapentin to a Novel Site in Rat Brain: Autoradiographic Studies", 1993, vol. 244, pp. 303–309.

Dissanayake, V.U.K. et al., British Journal of Pharmacology, "Spermine Modulcation fo Specific [3H]–Gabapentrin Binding to the Detergent–Solubilized porcine Cerebral Cortex α2δCalcium Channel Subunit" 1997, vol. 120, pp. 833–840.

Brickley, K. et al., Febs Letters, "Use of Site–Directed Antibodies to Probe the Topography of the two2 Subunit of Voltage–Gated CA2+ Channels", 1995, vol. 364, pp. 129–133.

Taylor, C.P., et al., Epilepsy Reserach, Potent and Stereospecific Anticonvulsant Activity of 3–Isobutyl Gaba Relates to in Vitro Binding at a Novel Site Labeled by Tritiated Gabapentin, 1993, vol. 14, pp. 11–15.

Thurlow, R.J., et al., European Journal of Pharmacology–Molecular Pharmacology Section, "[3H]Gabapentin May Label a System–L–Like Neutral Amino Acid Carrier in Brain", 1993, vol. 247, pp. 341–345.

Suman–Chauman, N., et al., European Journal of Pharmacology–Molecular Pharmacology Section, "Characterisation of [3H]Gabapentin Binding to a Novel Site in Rat Brain: Homogenate Binding Studies", 1993, vol. 244, pp. 293–301.

Ellis, S.B., et al., Science, "Sequence and Expression of MRNAS Encoding the α1 and α2 Subunit of a DHP–Sensitive Calcium Channel", 1988, vol. 241, pp. 1661–1664.

Dejongh, K.S., The Journal of Biological Chemistry, "Subunits of Purified Calcium Channels", 1990, vol. 265, pp. 14738–14741.

(List continued on next page.)

*Primary Examiner*—Gary Kunz
*Assistant Examiner*—Joseph F. Murphy
(74) *Attorney, Agent, or Firm*—Charles W. Ashbrook; Eric Baude; David R. Kurlandsky

(57) ABSTRACT

Soluble $\alpha_2\delta$ sub-type polypeptides.

Methods for cloning, expression and purification of freely soluble $\alpha_2\delta$ subtype polypeptides.

A method for the screening of ligands which bind to soluble $\alpha_2\delta$ subtype polypeptides.

23 Claims, No Drawings

OTHER PUBLICATIONS

Jay, S.D., et al., The Journal of Biological Chemistry "Strucutural Characterization of The Dihydrophridine–Sensitive Calcium Channel α2–Subunit and Th Eassociated δPeptides", 1991, vol. 266, pp. 3287–3293.

Wiser, O., et al., Febs Letters, The δ2/δSubunit of Voltage Sensitive CA2+ Channels is a Single Transmembrane Extracellular Protein Which is Involved in Regulated Secretion, 1996, vol. 379, pp. 15–20.

Brown, J.P., et al., Rev. Contemp. Pharmacother, "Mechanisms of Action of Gabapentin", 1996, vol. 7, pp. 203–214.

Brown, J.P., et al., Analytical Biochemistry, "Isolation of the [3H]Gabapentin–Binding Protein/α2δCA2+ Channel Subunit From Procine Brain: Development of a Radioligand Binding Assay for α2δSubunits Using [3H]Leucine", 1998, vol. 255, pp. 236–243.

* cited by examiner

SECRETED SOLUBLE α2δ-2, α2δ-3 OR α2δ-4 CALCIUM CHANNEL SUBUNIT POLYPEPTIDES AND SCREENING ASSAYS USING SAME

BACKGROUND OF THE INVENTION

Voltage-dependent $Ca^{2+}$ channels (VDCCs) are heteromultimeric complexes present in both neuronal and non-neuronal tissues, including heart and skeletal muscle. VDCCs are minimally composed of three subunits: a pore-forming transmembrane $\alpha_1$ subunit, a hydrophilic intracellular β subunit, and a membrane-associated $\alpha_2\delta$ subunit; a transmembrane γ subunit is also found in skeletal muscle tissue. Multiple subtypes and/or splice variants of the $\alpha_1$, β, and $\alpha_2\delta$ subunits have been found.

Gabapentin ((1-aminomethyl)cyclohexane acetic acid or Neurontin) is a structural analogue of GABA, which is mainly used as an adjunctive therapy for epilepsy. Recent research suggests that gabapentin may also have clinical utility for various indications including anxiety and pain. Although designed as a lipophilic GABA-mimetic, gabapentin does not have a high affinity for either $GABA_A$ or $GABA_B$ receptors, GABA uptake sites, or the GABA-degrading enzyme GABA-transaminase (EC 2.6.1.19).

A novel high affinity binding site for $[^3H]$gabapentin in rat, mouse, and porcin brains has been characterized. Recently, the $[^3H]$gabapentin-binding protein was isolated from pig brain and identified as the $\alpha_2\delta$-1 subunit of VDCCs. None of the prototypic anticonvulsant drugs displace $[^3H]$gabapentin binding from the $\alpha_2\delta$-1 subunit. $[^3H]$Gabapentin-binding is stereospecifically inhibited by two enantiomers of 3-isobutyl GABA. The rank order of potency of gabapentin, and S- and R-isobutyl GABA, at the $[^3H]$gabapentin binding site mirrors their anticonvulsant activity in mice. However, electrophysiological studies have yielded conflicting data on the action of gabapentin at VDCCs.

The $\alpha_2\delta$ subunit is derived from a single gene, the product of which is extensively post-translationally modified particularly through the cleavage of the signal sequence. The polypeptide is cleaved to form disulfide-bridged $\alpha_2$ and δ peptides, both of which are heavily glycosylated. Although it seems clear today that the $\alpha_2$ and δ peptides are membrane-associated peptides, it is unclear whether these peptides comprise one or several transmembrane domains. Furthermore, the location, size and structural configuration of these eventual transmembrane domains remains to be determined.

But in any event, the fact that $\alpha_2\delta$ is a membrane-associated protein, regardless of its precise structural configuration, renders its large scale expression in recombinant systems difficult. Indeed, as the $\alpha_2\delta$ protein is targeted to the membrane, it requires detergent solubilisation to release it for purification. This important drawback imposes considerable restrictions for any potential applications requiring large amounts of recombinant protein. Furthermore, the various subtypes of $\alpha_2\delta$ subunits are different proteins with very low homologies. It is therefore extremely difficult to predict their respective behaviors, for example in gene truncation experiments.

The only assay currently available for the screening of ligands that bind the $\alpha_2\delta$ subunit involves the use of pig membrane extracts as a source of the $\alpha_2\delta$ subunit. Such an assay presents major inconvenients. Firstly, because the assay material is a membrane extract, it is very difficult to accurately determine the protein composition from one assay preparation to another particularly with regard to the subtype. Also, the presence of various impurities in the assay preparation is a problem in small plate assays. Furthermore, as the protein preparation lacks homogeneity, the interaction between the targeted protein and the assay plate is often quite uneven. This renders the streamlining of the assay in a high throughput format almost impossible to achieve.

SUMMARY OF THE INVENTION

In the context of the present invention, the inventors have found that it was possible to delete a portion of the nucleotide sequence encoding a eukaryotic, preferably a mammal cerebral cortical voltage-dependent calcium channel $\alpha_2$ subunit to yield a soluble secreted protein which retains its affinity for $[^3H]$gabapentin.

The Invention Concerns:

1) A purified or isolated nucleic acid encoding a mammalian secreted soluble cerebral cortical voltage-dependent calcium channel $\alpha_2\delta$-2, $\alpha_2\delta$-3 or $\alpha_2\delta$-4 subunit polypeptide.

2) A purified or isolated nucleic acid according to 1), comprising a polynucleotide having at least 90% identity with the sequence encoding:

from amino acid 1 to between amino-acids 1027 and 1062 of SEQ ID NO:20 for $\alpha_2\delta$-2, from amino acid 1 to between amino-acids 984 and 1019 of SEQ ID NO:22 for $\alpha_2\delta$-3.

3) A purified or isolated nucleic acid according to 1), having at least 90% identity with the sequence encoding:

from amino acid 1 to between amino-acids 1047 and 1062 of SEQ ID NO:20 for $\alpha_2\delta$-2, from amino acid 1 to between amino-acids 1004 and 1019 of SEQ ID NO:22 for $\alpha_2\delta$-3.

4) A purified or isolated nucleotide sequence according to 1) wherein said sequence is the sequence of SEQ ID NO:1, SEQ ID NO:2, SEQ ID NO:3, SEQ ID NO:7, SEQ ID NO:8, SEQ ID NO:9, SEQ ID NO:13, SEQ ID NO:14, SEQ ID NO:15, SEQ ID NO:19, or SEQ ID NO:21.

5) A purified or isolated nucleic acid, having at least 90% identity with the nucleotide sequence of SEQ ID NO:19 or SEQ ID NO:21.

6) A purified or isolated polynucleotide comprising at least 10 consecutive nucleotides of the nucleotide sequence of SEQ ID NO:19 or SEQ ID NO:21.

7) A polynucleotide probe or primer hybridizing, under stringent conditions, with the nucleotide sequence of SEQ ID NO:19 or SEQ ID NO:21.

8) A method for the amplification of a nucleic acid encoding a mammalian secreted soluble cerebral cortical voltage-dependent calcium channel $\alpha_2\delta$-n subunit polypeptide wherein n is 2, 3 or 4, said method comprising the steps of:

(a) contacting a test sample suspected of containing the target secreted soluble $\alpha_2\delta$-n subunit nucleic acid, or a sequence complementary thereto, with an amplification reaction reagent comprising a pair of amplification primers located on either side of the $\alpha_2\delta$-n subunit nucleic acid region to be amplified, and (b) optionally, detecting the amplification products.

9) A kit for the amplification of a nucleic acid encoding a secreted soluble $\alpha_2\delta$-n subunit polypeptide wherein n is 2, 3 or 4, or a complementary sequence thereto in a test sample, wherein said kit comprises:

(a) a pair of oligonucleotide primers which can hybridize, under stringent conditions, to the secreted soluble $\alpha_2\delta$-n subunit nucleic acid region to be amplified;

(b) optionally, the reagents necessary for performing the amplification reaction.

10) A recombinant vector comprising a nucleic acid according to 1).

11) A recombinant host cell comprising a nucleic acid according to 1).

12) A method for producing a secreted soluble $\alpha_2\delta$-n subunit wherein n is 2, 3 or 4, and said method comprises the steps of:

(a) inserting the nucleic acid encoding the desired $\alpha_2\delta$-n subunit polypeptide in an appropriate vector;

(b) culturing, in an appropriate culture medium, a host cell previously transformed or transfected with the recombinant vector of step (a);

(c) harvesting the culture medium thus obtained or lyse the host cell, for example by sonication or osmotic shock;

(d) separating or purifying, from said culture medium, or from the pellet of the resultant host cell lysate, the thus produced $\alpha_2\delta$-n subunit polypeptide of interest.

13) A purified or isolated recombinant polypeptide comprising the amino acid sequence of a secreted soluble $\alpha_2\delta$-2, $\alpha_2\delta$-3 or $\alpha_2\delta$-4 subunit polypeptide.

14) A recombinant polypeptide according to 13), having at least 80% amino-acid identity with a polypeptide comprising:

from amino acid 1 to between amino acids 1027 and 1062 of the amino acid sequence of SEQ ID NO:20, or from amino acid 1 to between amino acids 1019 and 1079 of the amino acid sequence of SEQ ID NO:22.

15) A recombinant polypeptide according to 14), wherein said recombinant polypeptide is selected from the group consisting of the amino acid sequences of SEQ ID NO:4, SEQ ID NO:5, SEQ ID NO:6, SEQ ID NO:10, SEQ ID NO:11, SEQ ID NO:12, SEQ ID NO:16, SEQ ID NO:17 and SEQ ID NO:18.

16) A method for the screening of ligands which bind a cerebral cortical voltage-dependent calcium channel $\alpha_2\delta$-n subunit wherein n is 2, 3 or 4, said method comprising the steps of:

contacting a secreted soluble recombinant calcium channel $\alpha_2\delta$-n subunit polypeptide with:

a: ligand of interest; and a labelled compound which binds the $\alpha_2\delta$-n subunit; and measuring the level of binding of the labelled compound to the $\alpha_2\delta$-n subunit.

17) A method according to 16), wherein said method is a scintillation proximity assay.

18) A method according to 16), wherein said method is a flashplate assay.

19) A method according to 16), wherein said method is a filter binding assay.

20) A method according to 16), wherein said secreted soluble recombinant calcium channel $\alpha_2\delta$-n subunit polypeptide is selected from polypeptides having at least 80%, preferably 90%, more preferably 95%, and most preferably 98 or 99% amino-acid identity with the polypeptide comprising from amino acid 1 to between amino-acids 984 and 1063, preferably between amino-acids 994 and 1054, and most preferably between amino-acids 1019 and 1054 of SEQ ID NO:5 or SEQ ID NO:16.

21) A method according to 16), wherein sad secreted soluble recombinant calcium channel $\alpha_2\delta$-n subunit polypeptide is selected from the group consisting of SEQ ID NO:6, 7, 8, 9, 13, 14 and 15, with the polypeptides of SEQ ID NO:9 and SEQ ID NO:15 being most preferred.

22) A kit for the screening of ligands which bind bind a cerebral cortical voltage-dependent calcium channel $\alpha_2\delta$-n subunit wherein n is 2, 3 or 4, said kit comprising:

a secreted soluble recombinant calcium channel $\alpha_2\delta$-n subunit; and a labelled compound which binds to the $\alpha_2\delta$-n subunit.

Hence, the invention concerns nucleotide sequence fragments of a cerebral cortical voltage dependent calcium channel $\alpha_2\delta$-2, $\alpha_2\delta$-3 or $\alpha_2\delta$-4 subunit cDNA encoding a soluble secreted $\alpha_2\delta$-2, $\alpha_2\delta$-3 or $\alpha_2\delta$-4 subunit polypeptide (hereinafter a $\alpha_2\delta$-2, $\alpha_2\delta$-3 or $\alpha_2\delta$-4 subunit). Preferably, these nucleotide sequences encode a soluble secreted $\alpha_2\delta$-2, $\alpha_2\delta$-3 or $\alpha_2\delta$-4 subunit polypeptide bearing a gabapentin or a $[^3H]$gabapentin binding site. More preferably, the soluble secreted $\alpha_2\delta$-2, $\alpha_2\delta$-3 or $\alpha_2\delta$-4 subunit nucleic acid is derived from a eukaryotic, preferably a mammal, more preferably a human $\alpha_2\delta$-2, $\alpha_2\delta$-3 or $\alpha_2\delta$-4 subunit.

A further object of the present invention concerns recombinant vectors comprising a nucleic acid sequence encoding a soluble secreted $\alpha_2\delta$-2, $\alpha_2\delta$-3 or $\alpha_2\delta$-4 subunit polypeptide.

The invention also encompasses host cells and transgenic non-human mammals comprising said nucleic acid sequences or recombinant vectors.

The invention also concerns a soluble secreted $\alpha_2\delta$-2, $\alpha_2\delta$-3 or $\alpha_2\delta$-4 subunit polypeptide which is characterized in that it is a soluble secreted polypeptide having affinity for $[^3H]$gabapentin. Preferably, the soluble secreted polypeptide is derived from a mammal, more preferably a human $\alpha_2\delta$-2, $\alpha_2\delta$-3 or $\alpha_2\delta$-4 subunit.

The inventors have also found that it was possible to use a soluble secreted form of a voltage-dependant calcium channel $\alpha_2\delta$-2, $\alpha_2\delta$-3 or $\alpha_2\delta$-4 subunit polypeptide in an assay for the screening of ligands which bind the $\alpha_2\delta$-2, $\alpha_2\delta$-3 or $\alpha_2\delta$-4 subunit.

The invention therefore also concerns a method for the screening of ligands which bind a calcium channel $\alpha_2\delta$-2, $\alpha_2\delta$-3 or $\alpha_2\delta$-4 subunit.

The method comprises the steps of:

contacting a secreted soluble recombinant calcium channel $\alpha_2\delta$-2, $\alpha_2\delta$-3 or $\alpha_2\delta$-4 subunit polypeptide with:

a ligand of interest; and a labelled compound which binds a $\alpha_2\delta$-2, $\alpha_2\delta$-3 or $\alpha_2\delta$-4 subunit, and measuring the level of binding of the labelled compound to the secreted soluble $\alpha_2\delta$-2, $\alpha_2\delta$-3 or $\alpha_2\delta$-4 subunit.

The invention also concerns a kit for the screening of ligands which bind a calcium channel $\alpha_2\delta$-2, $\alpha_2\delta$-3 or $\alpha_2\delta$-4 subunit.

The kit comprises:

a secreted soluble recombinant calcium channel $\alpha_2\delta$-2, $\alpha_2\delta$-3 or $\alpha_2\delta$-4 subunit polypeptide; and a labelled compound which binds a calcium channel $\alpha_2\delta$-2, $\alpha_2\delta$-3 or $\alpha_2\delta$-4 subunit.

DETAILED DESCRIPTION OF THE INVENTION

The invention concerns truncated $\alpha_2\delta$-2, $\alpha_2\delta$-3 or $\alpha_2\delta$-4 subunit cDNA sequences. These truncated sequences encode soluble secreted polypeptides which retain their affinity for $[^3H]$gabapentin.

Throughout the present specification, the expression "nucleotide sequence" is used to designate indifferently a polynucleotide or a nucleic acid. More precisely, the expression "nucleotide sequence" encompasses the nucleic material and the sequence information and is not restricted to the sequence information (i.e. the succession of letters chosen among the four base letters) that biochemically characterizes a specific DNA or RNA molecule.

As used interchangeably herein, the terms "oligonucleotides", "nucleic acids" and "polynucleotides" include RNA, DNA, or RNA/DNA hybrid sequences of more than one nucleotide in either single chain or duplex form.

Further to its general meaning understood by the one skilled in the art, the term "nucleotide" is also used herein to encompass modified nucleotides which comprise at least one of the following modifications (a) an alternative linking group, (b) an analogous form of purine, (c) an analogous form of pyrimidine, or (d) an analogous sugar. For examples of analogous linking groups, purines, pyrimidines, and sugars, see for example PCT publication N°WO 95/04064.

The polynucleotide sequences of the invention may be prepared by any know method, including synthetic, recombinant, or a combination thereof as well as through any purification methods known in the art.

A) Secreted $\alpha_2\delta$-2, $\alpha_2\delta$-3 or $\alpha_2\delta$-4 Subunit Polypeptides The invention comprises polynucleotide sequences encoding a soluble secreted eukaryotic, preferably a soluble secreted mammal $\alpha_2\delta$-2, $\alpha_2\delta$-3 or $\alpha_2\delta$-4 subunit polypeptide. These sequences particularly include but are not restricted to 1) those sequences encoding a soluble secreted polypeptide of this $\alpha_2\delta$-2, $\alpha_2\delta$-3 or $\alpha_2\delta$-4 subunit which preferably retains its binding affinity for [$^3$H]gabapentin and 2) nucleotide fragments useful as nucleic acid primers or probes for amplification or detection purposes.

The expression "soluble secreted $\alpha_2\delta$-2, $\alpha_2\delta$-3 or $\alpha_2\delta$-4 subunit" is intended to designate polypeptide sequences which, when produced by a recombinant host cell, are secreted at least partially into the culture medium rather than remaining associated with the host cell membrane.

1) cDNA Fragments Encoding Soluble Secreted $\alpha_2\delta$-2, $\alpha_2\delta$-3, $\alpha_2\delta$-4 Subunit Polypeptides One of the important embodiments of the present invention concerns truncated nucleotide sequences of $\alpha_2\delta$-2, $\alpha_2\delta$-3 or $\alpha_2\delta$-4 subunit cDNAs which encode soluble secreted $\alpha_2\delta$-2, $\alpha_2\delta$-3 or $\alpha_2\delta$-4 subunit polypeptides. The inventors have found that it was possible to generate deletion mutants of $\alpha_2\delta$-2, $\alpha_2\delta$-3 or $\alpha_2\delta$-4 subunit cDNAs which, when expressed, produce a significant amount of soluble secreted proteins, preferably soluble secreted proteins, which retain their [$^3$H]gabapentin binding affinity. These truncated nucleotide sequences of the invention are of significant value to the skilled person as they now allow fast and reliable access to significant concentrations of selected soluble secreted $\alpha_2\delta$-2, $\alpha_2\delta$-3 or $\alpha_2\delta$-4 subunit polypeptides. To that end, the inventors have determined the minimal and optimal fragment lengths required to express a polypeptide which: 1) binds [$^3$H]gabapentin with sufficient affinity and; 2) is obtained in a soluble secreted form.

The discussion provided below provides comments on possible truncations, giving as an example the human $\alpha_2\delta$-2, $\alpha_2\delta$-3 or $\alpha_2\delta$-4 subunit. However, given the very substantial cross-species homology for $\alpha_2\delta$-2, $\alpha_2\delta$-3 or $\alpha_2\delta$-4 subunit sequences, the comments below can also be applied to other eukaryotic species, and more particularly other mammalian species such as rat, mouse, rabbit or pig. Their $\alpha_2\delta$-2, $\alpha_2\delta$-3 or $\alpha_2\delta$-4 subunit sequences, which for most are available in public databases, share a very substantial homology with the human $\alpha_2\delta$-2, $\alpha_2\delta$-3 or $\alpha_2\delta$-4 subunit sequences.

The inventors believe that the soluble secreted $\alpha_2\delta$-2 subunit polypeptides which are as close as possible to the native sequence and which are therefore more likely to retain their native folding and hence their [$^3$H]gabapentin binding properties are those corresponding to the native protein in which amino-acid stretch_1027_to_the C-terminal end_of the amino-acid sequence of SEQ ID NO:20 has been deleted. The skilled scientist can quite easily determine within this amino-acid stretch the optimal $\alpha_2\delta$-2 subunit polypeptides.

The inventors also believe that the soluble secreted $\alpha_2\delta$-3 subunit_polypeptides which are as close as possible to the native sequence and which are therefore more likely to retain their native folding and hence their [$^3$H]gabapentin binding properties are those corresponding to the native protein in which amino-acid stretch_984_to_C-terminal end_of the amino-acid sequence of SEQ ID NO:22 has been deleted. The skilled scientist can quite easily determine within this amino-acid stretch the optimal $\alpha_2\alpha$-3 subunit polypeptides.

The invention therefore particularly concerns a nucleotide sequence encoding a polypeptide having at least 80% identity with the polypeptide comprising from amino-acid 1 to between amino-acids_1027_and_1145_, preferably to between amino-acids_1062_and_1145 of SEQ ID NO:20.

Preferred nucleotide sequences include those of SEQ ID NO:1, SEQ ID NO:2 and SEQ ID NO:3.

The invention also concerns a nucleotide sequence encoding a polypeptide having at least 80% identity with the polypeptide comprising from amino-acid 1 to between amino-acids_984_and 1085_, preferably to between amino-acids 1019_and_1085 of SEQ ID NO:22.

Preferred nucleotide sequences include those of SEQ ID NO:7, SEQ ID NO:8 and SEQ ID NO:9.

B) Amplification of the Soluble Secreted $\alpha_2\delta$-2, $\alpha_2\delta$-3 or $\alpha_2\delta$-4 Subunit Nucleotide Sequences Another object of the invention consists of a method for the amplification of a nucleic acid encoding a soluble secreted $\alpha_2\delta$-2, $\alpha_2\delta$-3 or $\alpha_2\delta$-4 subunit polypeptide, preferably a polypeptide bearing a [$^3$H]gabapentin binding site, said method comprising the steps of:

(a) contacting a test sample suspected of containing the target $\alpha_2\delta$-2, $\alpha_2\delta$-3 or $\alpha_2\delta$-4 subunit nucleic acid, a fragment or a variant thereof, or a sequence complementary thereto, with an amplification reaction reagent comprising a pair of amplification primers which can hybridize under stringent conditions, the $\alpha_2\delta$-2, $\alpha_2\delta$-3 or $\alpha_2\delta$-4 subunit nucleic acid region to be amplified, and (b) optionally, detecting the amplification products.

The expression [$^3$H]gabapentin binding site, when used herein is intented to designate a site which can bind either [$^3$H]gabapentin or other ligands such as (S+)3-isobutyl gaba or (R−)-3-isobutyl gaba.

In a first preferred embodiment of the above method, the nucleic acid encodes a secreted soluble $\alpha_2\delta$-2, $\alpha_2\delta$-3 or $\alpha_2\delta$-4 subunit polypeptide of SEQ ID NO:4, SEQ ID NO:5, SEQ ID NO:6, SEQ ID NO:10, SEQ ID NO:11, SEQ ID NO:12, SEQ ID NO:16, SEQ ID NO:17 and SEQ ID NO:18.

In a second preferred embodiment of the above amplification method, the amplification product is detected by hybridization with a labelled probe having a sequence which is complementary to the amplified region.

C) Recombinant Vectors and Hosts Cells for the Expression of a Secreted Soluble $\alpha_2\delta$-2, $\alpha_2\delta$-3 or $\alpha_2\delta$-4 Subunit Polypeptide 1) Recombinant Vectors The present invention also encompasses a family of recombinant vectors comprising any one of the nucleic acids described herein. Firstly, the invention deals with a recombinant vector comprising a nucleic acid selected from the group consisting of:

(a) a purified or isolated nucleic acid encoding a secreted soluble $\alpha_2\delta$-2, $\alpha_2\delta$-3 or $\alpha_2\delta$-4 subunit having at least 80% amino acid identity with the polypeptide of SEQ ID NO:20 or 22, or a sequence complementary thereto;

(b) a purified or isolated nucleic acid having at least 90% nucleotide identity with a polynucleotide selected from the group consisting of the nucleotide sequences of SEQ ID NO:1, SEQ ID NO:2, SEQ ID NO:3, SEQ ID NO:7, SEQ ID NO:8, SEQ ID NO:9, SEQ ID NO:13, SEQ ID NO:14, SEQ ID NO:15 or a sequence complementary thereto;

(c) a purified or isolated polynucleotide comprising at least 10 consecutive nucleotides of a nucleic acid described in (a) or (b) or a sequence complementary thereto.

In a first preferred embodiment a recombinant vector of the invention is used to amplify the inserted polynucleotide of the invention in a suitable host cell, this polynucleotide being amplified every time the recombinant vector replicates.

Recombinant expression vectors comprising a nucleic acid encoding secreted soluble $\alpha_2\delta$-2, $\alpha_2\delta$-3 or $\alpha_2\delta$-4 subunit polypeptides that are described in the present specification are also part of the invention. These include, but are not restricted to, nucleic acids encoding from amino-acid 1 to between amino-acids 1027 and 1145, preferably between amino-acids 1062 and 1145 of SEQ ID NO:20, as well as nucleic acids encoding from amino-acid 1 to between amino-acids 984 and 1085, preferably between amino-acids 1019 and 1085, of SEQ ID NO:22.

Another preferred embodiment of the recombinant vectors according to the invention consist of expression vectors comprising a nucleic acid encoding $\alpha_2\delta$-2, $\alpha_2\delta$-3 or $\alpha_2\delta$-4 subunit polypeptides of the invention, and more preferably a nucleic acid encoding a polypeptide selected from the group consisting of the amino acid sequences of SEQ ID NO:4, SEQ ID NO:5, SEQ ID NO:6, SEQ ID NO:10, SEQ ID NO:11, SEQ ID NO:12, SEQ ID NO:16, SEQ ID NO:17 and SEQ ID NO:18.

Within certain embodiments, expression vectors can be employed to express the secreted soluble $\alpha_2\delta$-2, $\alpha_2\delta$-3 or $\alpha_2\delta$-4 subunit polypeptides which can then be purified and for example, be used as a immunogen in order to raise specific antibodies directed against said secreted soluble $\alpha_2\delta$-2, $\alpha_2\delta$-3 or $\alpha_2\delta$-4 subunit polypeptides.

Preferred eukaryotic vectors of the invention are listed hereafter as illustrative but not limitative examples: pcDNA3, pFLAG, pCMV-Script, pIND, pMC1NEO, pHIL, pGAPZA, pMT/V5-His-TOPO, pMT/V5-His, pAc5.1/V5-HisA, pDS47/V5-His, pcDNA4, pcDNA6, pEF1, pEF4, pEF6, pUB6, pZeoSV2, pRc/CMv2, pcDM8, pCR3.1, pDisplay, pSecTag2, pVP22, pEMZ, pCMV/Zeo, pSinRep5, pCEP, pREP, pHook-1.

Preferred bacteriophage recombinant vectors of the invention are P1 bacteriophage vectors such as described by Sternberg N. L. (1992;1994).

A suitable vector for the expression of a soluble secreted $\alpha_2\delta$-2, $\alpha_2\delta$-3 or $\alpha_2\delta$-4 subunit polypeptide is a baculovirus vector that can be propagated in insect cells and in insect cell-lines. Specific suitable host vectors includes, but are not restricted to: pFastBac-1, pIZ/V5-His, pBacMan-1, pBlueBac4.5, pBlueBacHis2, pMelBacA, pVL1392, pVL1393.

The recombinant expression vectors from the invention may also be derived from an adenovirus such as those described by Feldman and Steig. (1996) or Ohno et al. (1994). Another preferred recombinant adenovirus according to this specific embodiment of the present invention is the human adenovirus type two or five (Ad 2 or Ad 5) or an adenovirus of animal origin (French Patent Application n°FR 93 05 954).

a) Regulatory Expression Sequences

Expression requires that appropriate signals are provided in the vectors, said signals including various regulatory elements such as enhancers/promoters from both viral and mammalian sources that drive expression of the genes of interest in host cells. The regulatory sequences of the expression vectors of the invention are operably linked to the nucleic acid a soluble secreted $\alpha_2\delta$-2, $\alpha_2\delta$-3 or $\alpha_2\delta$-4 subunit polypeptide. As used herein, the term "operably linked" refers to a linkage of polynucleotide elements in a functional relationship. For instance, a promoter or an enhancer is operably linked to a coding sequence if it affects the transcription of the coding sequence. More precisely, two DNA molecules (such as a polynucleotide containing a promoter region and a polynucleotide encoding a desired polypeptide or polynucleotide) are said to be "operably linked" if the nature of the linkage between the two polynucleotides does not: (1) result in the introduction of a frame-shift mutation or (2) interfere with the ability of the polynucleotide containing the promoter to direct the transcription of the coding polynucleotide.

Generally, recombinant expression vectors include origins of replication, selectable markers permitting transformation of the host cell, and a promoter derived from a highly expressed gene to direct transcription of a downstream structural sequence. The heterologous structural sequence is assembled in an appropriate frame with the translation, initiation and termination sequences, and preferably a leader sequence capable of directing sequences of the translated protein into the periplasmic space or the extra-cellular medium. In a specific embodiment wherein the vector is adapted for transfecting and expressing desired sequences in eukaryotic host cells, preferred vectors comprise an origin of replication from the desired host, a suitable promoter and an enhancer, and also any necessary ribosome binding sites, polyadenylation site, transcriptional termination sequences, and optionally 5'-flanking non-transcribed sequences.

DNA sequences derived from the SV 40 viral genome, for example SV 40 origin early promoter, enhancer, and polyadenylation sites may be used to provide the required non-transcribed genetic elements.

b) Promoter Sequences

Suitable promoter regions used in the expression vectors according to the invention are chosen taking into account the host cell in which the heterologous nucleic acids have to be expressed.

A suitable promoter may be heterologous with respect to the nucleic acid for which it controls the expression, or alternatively can be endogenous to the native polynucleotide containing the coding sequence to be expressed.

Additionally, the promoter is generally heterologous with respect to the recombinant vector sequences within which the construct promoter/coding sequence has been inserted. Preferred eukaryotic promoters are the CMV, polyhidran or OPIE2.

Recombinant Host Cells

Host cells that have been transformed or transfected with one of the nucleic acids described herein, or with one of the recombinant vector, particularly recombinant expression vector, described herein are also part of the present invention.

Are included host cells that are transformed (prokaryotic cells) or are transfected (eukaryotic cells) with a recombinant vector such as one of those described above.

Preferred host cells used as recipients for the expression vectors of the invention are the following:

(a) prokaryotic host cells: *Escherichia coli*, strains. (i.e. DH10 Bac strain) *Bacillus subtilis, Salmonella typhimurium* and strains from species such as Pseudomonas, Streptomyces and Staphylococcus;

(b) eukaryotic host cells: HeLa cells (ATCC N°CCL2; N°CCL2.1; N°CCL2.2), Cv 1 cells (ATCC N°CCL70), COS cells (ATCC N°CRL 1650; N°CRL 1651), Sf-9 cells (ATCC N°CRL 1711), C127 cells (ATCC N°CRL-1804), 3T3 cells (ATCC N°CRL-6361), CHO cells (ATCC N°CCL-61), human kidney 293 cells (ATCC N°45504; N°CRL-1573), BHK (ECACC N°84100 501; N°84111301), sf 9, sf 21 and hi-5 cells.

D) Production of Recombinant Secreted Soluble $\alpha_2\delta$-2, $\alpha_2\delta$-3 or $\alpha_2\delta$-4 Subunit Polypeptides The present invention also concerns a method for producing one of the amino acid sequences described herein and especially a polypeptide selected from the group consisting of the amino acid sequences of SEQ ID NO:4, SEQ ID NO:5, SEQ ID NO:6, SEQ ID NO:10, SEQ ID NO:11, SEQ ID NO:12, SEQ ID NO:16, SEQ ID NO:17 or SEQ ID NO:18 wherein said method comprises the steps of:

(a) inserting the nucleic acid encoding the desired amino acid sequence in an appropriate vector;

(b) culturing, in an appropriate culture medium, a host cell previously transformed or transfected with the recombinant vector of step (a);

(c) harvesting the culture medium thus obtained or lyse the host cell, for example by sonication or osmotic shock;

(d) separating or purifying, from said culture medium, or from the pellet of the resultant host cell lysate, the thus produced recombinant polypeptide of interest.

In some instances, it is required to tag the secreted soluble $\alpha_2\delta$-2, $\alpha_2\delta$-3 or $\alpha_2\delta$-4 subunit polypeptide prior to purification. The tag is then in most instances encoded into the nucleotide sequence that is need to express the polypeptide. Examples of such tags include, but are not limited to sequences encoding C-myc, FLAG, a sequence of histidine residues, heamaglutin A, V5, Xpress or GST. Most of these tags can be incorporated directly into the sequence, for instance through PCR amplification by incorporating the appropriate coding sequence in one of the PCR amplification primers. However, the tag can also be introduced by other means such as covalent binding of the appropriate nucleic acid sequence encoding the tag moiety with the 3' or 5' end of the nucleic acid sequence encoding the polypeptide sequence. This is the case for GST.

Purification of the recombinant secreted soluble $\alpha_2\delta$-2, $\alpha_2\delta$-3, $\alpha_2\delta$-4 subunit polypeptides according to the present invention is then carried out by passage onto a nickel or copper affinity chromatography column, such as a Ni NTA column or a Q-Sepharose column.

In another embodiment of the above method, the polypeptide thus produced is further characterized, for example by binding onto an immuno-affinity chromatography column on which polyclonal or monoclonal antibodies directed to the secreted soluble $\alpha_2\delta$-2 subunit polypeptide of interest have been previously immobilised.

In another embodiment of the invention, the secreted soluble $\alpha_2\delta$-2, $\alpha_2\delta$-3, $\alpha_2\delta$-4 subunit polypeptide can be only partially purified. For instance, it can be purified along with other contaminating proteins using an appropriate chromatography matrix such as an ion-exchange chromatography column. In such instances, it is not required to tag the desired polypeptide of interest.

The most preferred embodiment contemplated by the inventors concerns the use of a purified tagged secreted soluble $\alpha_2\delta$-2, $\alpha_2\delta$-3 or $\alpha_2\delta$-4 subunit polypeptide. A particularly preferred tag is a nucleotide sequence encoding from 2 to 10, and preferably 6 histidine residues.

With regard to the secreted soluble $\alpha_2\delta$-2, $\alpha_2\delta$-3 or $\alpha_2\delta$-4 subunit polypeptide used subsequently in the screening assay of the invention, several possibilities are also open to the skilled person.

In a first and preferred embodiment, the secreted soluble $\alpha_2\delta$-2, $\alpha_2\delta$-3 or $\alpha_2\delta$-4 subunit polypeptide comprises a tag moiety which can be selected among the tags referred to above. Such tagged polypeptides are particularly useful in SPA or flashplate assays. A preferred tag is the nucleotide sequence encoding histidine residues referred to above.

In a second embodiment, the secreted soluble $\alpha_2\delta$-2, $\alpha_2\delta$-3 or $\alpha_2\delta$-4 subunit polypeptide can be used without a tag. This is the case for instance in SPA or flashplate assays comprising beads or plates coated with wheat germ lectin. In such an embodiment, the tag is not needed as the carbohydrate moieties of the secreted soluble $\alpha_2\delta$-2, $\alpha_2\delta$-3 or $\alpha_2\delta$-4 subunit polypeptide bind directly to the wheat germ lectin-coated beads or plates.

1) Labelled Compounds which Bind the Secreted Soluble $\alpha_2\delta$-2, $\alpha_2\delta$-3 or $\alpha_2\delta$-4 Subunit Polypeptide In cases where the $\alpha_2\delta$-2, $\alpha_2\delta$-3 or $\alpha_2\delta$-4 binding site is the [$^3$H]gabapentin binding site, the preferred labelled compound which can be used is of course gabapentin itself. However, gabapentin is not the only labelled compound which can be used in this context. Indeed, it has been previously demonstrated that saturation binding analyses on porcine synaptic plasma cerebral cortex membranes performed in the presence of L-leucine indicate a competitive interaction of the amino acid with the [$^3$H]gabapentin binding site, significantly reducing [$^3$H]gabapentin binding affinity for the site. The inventors believe that this competitive interaction is true across across all the amino-acids listed in table 1 below.

TABLE 1

Binding affinities of selected amino acids ($IC_{50}$ <500 nM) for the [$^3$H]gabapentin site in porcine cortical membranes

| COMPOUND | $IC_{50}$ (NM) ARITHMETIC MEAN (N = 3) ± S.E.M. |
|---|---|
| Gabapentin | 42.1 ± 5.5 |
| L-Norleucine | 23.6 ± 6.7 |
| L-Allo-Isoleucine | 32.8 ± 6.0 |
| L-Methionine | 49.6 ± 10.0 |
| L-Leucine | 61.3 ± 20.9 |
| L-Isoleucine | 68.8 ± 1.9 |
| L-Valine | 330 ± 18 |
| L-Phenylalanine | 351 ± 89 |

It is therefore possible to use commercialy available labelled forms of these high affinity ligands in replacement of gabapentin. The utility of [$^3$H]L-leucine has been demonstrated in a filter binding assay and in a flashplate assay format. The inventors believe that labelled amino acids but also other compounds, with affinities preferably below 500 nM in the binding assay can be used as replacements of gabapentin.

With regard to the label, several embodiments can be used in the context of the invention. Preferred labels are of course radioactive labels, a list of which is provided further in this specification.

2) Assay Formats and Conditions

Several assay formats can be used to carry out the method of the present invention. Preferred assay formats include scintillation assays such as the scintillation proximity assay (SPA) or the flashplate assay. Other assay formats well known to those skilled in the arts such as the filter binding assay and the centrifugation assay are also contemplated in the present invention.

SPA and flashplate assays are preferred assay formats for the present invention. Additional details on these assays are provided below.

Scintillation Assay Format

Scintillation assays technology either involves the use of scintillant beads (for the SPA assay) or plates (for the flashplate assay). SPA beads are usually made from either cerium-doped yttrium ion silicate (y2SiO5:Ce) or polyvinyltoluene (PVT) containing an organic scintillant such as PPO. Flashplates commonly used are those such as Ni chelate flashplates although other flashplates can also be used.

Assays are usually carried out in aqueous buffers using radioisotopes such as $^{3}H$, $^{125}l$, $^{14}c$, $^{35}S$ or $^{33}P$ that emit low-energy radiation, the energy of which is easily dissipated in an aqueous environment. For example, the electrons emitted by $^{3}H$ have an average energy of only 6 keV and have a very short path length (−1 ~tm) in water. If a molecule labelled with one of these isotopes is bound to the bead or flashplate surface, either directly or via interaction with another molecule previously coupled to the bead or flashplate, the emitted radiation will activate the scintillant and produce light. The amount of light produced, which is proportional to the amount of labelled molecules bound to the beads, can be measured conveniently with a liquid scintillation (LS) counter. If the labelled molecule is not attached to the bead or a flashplate surface, its radiation energy is absorbed by the surrounding aqueous solvent before it reaches the bead, and no light is produced. Thus, bound ligands give a scintillation signal, but free ligands do not, and the need for a time-consuming separation step, characteristic of conventional radioligand binding assays, is eliminated. The manipulations required in the assays are reduced to a few simple pipetting steps leading to better precision and reproducibility.

The conditions under which SPA and flashplate assays are performed in the context of the present invention are provided below.

Scintillation Assay Conditions a) SPA Assay

The SPA assays is first developed to optimize the conditions under which the radioligand binds the secreted soluble $\alpha_2\delta$-2, $\alpha_2\delta$-3 or $\alpha_2\delta$-4 subunit polypeptide. The parameters which can be varied to optimize radioligand binding in a typical SPA assay using Amersham beads include assay temperature, $\alpha_2\delta$-2, $\alpha_2\delta$-3 or $\alpha_2\delta$-4 subunit polypeptide interaction with the radioligand and the SPA beads, radioligand concentration as well as pH variations.

The temperature at which the assay can be carried out can vary from 1 to 30° C. Preferred temperatures range from 18 to 23° C., with 21° C. being the most preferred temperature. The interaction of the $\alpha_2\delta$ subunit polypeptide with the SPA beads can be optimized by adjusting the concentration of the polypeptide and by introducing a reagent which will favor this interaction. When 50 mg of Amersham SPA beads are used, the $\alpha_2\delta$-1 subunit polypeptide concentration may vary from 0.1 to 10 pmoles per well, with the optimal concentration being generally around 5 to 6 pmoles per well.

As for the reagent favoring the interaction between the secreted soluble $\alpha_2\delta$-2, $\alpha_2\delta$-3 or $\alpha_2\delta$-4 subunit polypeptide and the radioligand as well as the Amersham SPA beads, the inventors found that imidazole could be efficiently used for that purpose when the $\alpha_2\delta$-2, $\alpha_2\delta$-3 or $\alpha_2\delta$-4 subunit polypeptide is tagged with an amino acid sequence including 6 histidine residues. Furthermore, and more importantly, it was found that imidazole also enhanced binding of the radioligand to the $\alpha_2\delta$-2, $\alpha_2\delta$-3 or $\alpha_2\delta$-4 polypeptide.

The concentration of the radioligand is evaluated with respect to the concentration of secreted soluble $\alpha_2\delta$-2, $\alpha_2\delta$-3 or $\alpha_2\delta$-4 subunit polypeptide present in the assay medium. Generally, the concentration of radioligand varies from 1 nM to 100 nM. A preferred [$^{3}$H]gabapentin concentration is about 5 to 20 nM, with a most preferred concentration being about 10 nM. A preferred [$^{3}$H]leucine concentration is also about 5 to 20 nM, with a most preferred concentration being about 10 nM. It is to be noted that the concentration of other radioligands having affinities similar to those of [$^{3}$H] gabapentin and [$^{3}$H]leucine should also be in the range of about 5 to 20 nM.

Once the optimal radioligand binding conditions have been determined, a test ligand can be introduced in the assay medium to evaluate the level of displacement of the radioligand. The concentration of test ligand to be introduced in the assay medium usually varies from 0.1 nM to about 100 $\mu$M. A preferred test ligand concentration of about 10 $\mu$M is usually a starting point in a high throughput screening assay. Then, depending on the number of hits obtained, it may be lowered or increased.

It is to be noted that the parameters set forth above, which have been evaluated for a typical SPA assay using Amersham SPA beads can be adjusted by the skilled person, for example if SPA beads of a different type are used.

b) Flashplate Assay

Similarly to the SPA assays, the flashplate can first be developed in order to optimize the conditions under which the radioligand binds the $\alpha_2\delta$ subunit polypeptide. The parameters which can be varied to optimize radioligand binding in a typical flashplate assay using NEN Ni chelate flashplates also include assay temperature, secreted soluble $\alpha_2\delta$-2, $\alpha_2\delta$-3 or $\alpha_2\delta$-4 subunit polypeptide interaction with both the radioligand and the flashplates, radioligand concentration as well as pH variations.

The temperature at which the assay can be carried out can vary from 1 to 30° C. Preferred temperatures range from 18 to 23° C., with 21° C. being the most preferred temperature.

The interaction of the secreted soluble $\alpha_2\delta$-2, $\alpha_2\delta$-3 or $\alpha_2\delta$-4 subunit polypeptide with the flashplates can be optimized by adjusting the concentration of the polypeptide and by introducing a reagent which will favor this interaction. When a standard NEN Ni chelate flashplate is used, the secreted soluble $\alpha_2\delta$-2, $\alpha_2\delta$-3 or $\alpha_2\delta$-4 subunit polypeptide volume usually varies between 0.5 and 20 $\mu$l for a concentration of secreted soluble $\alpha_2\delta$-2, $\alpha_2\delta$-3 or $\alpha_2\delta$-4 subunit polypeptide of 0.6 pmol/$\mu$l. As the published maximum binding capacity of NEN p plates is about 6 pmol per well, the inventors consider that an optimal concentration of secreted $\alpha_2\delta$-2, $\alpha_2\delta$-3 or $\alpha_2\delta$-4 subunit polypeptide is probably around 5 pmol per well at 8 $\mu$l.

With regard to the reagent favoring the interaction between the secreted soluble $\alpha_2\delta$-2, $\alpha_2\delta$-3 or $\alpha_2\delta$-4 subunit polypeptide and the radioligand as well as the flashplates, the inventors believe that imidazole could also be efficiently used for that purpose when the secreted soluble $\alpha_2\delta$-2, $\alpha_2\delta$-3 or $\alpha_2\delta$-4 subunit polypeptide is tagged with an amino acid sequence including 6 histidine residues. The inventors also believe that imidazole concentrations can substantially enhance binding of the radioligand to the secreted soluble $\alpha_2\delta$-2, $\alpha_2\delta$-3 or $\alpha_2\delta$-4 polypeptide. The optimal concentration of imidazole used to enhance radioligand binding varies depending on the concentration of secreted soluble $\alpha_2\delta$-2, $\alpha_2\delta$-3 or $\alpha_2\delta$-4 subunit polypeptide used in the assay. For instance, when the volume of the $\alpha_2\delta$-1 subunit polypeptide is about 10 $\mu$l ($\alpha_2\delta$-2, $\alpha_2\delta$-3 or $\alpha_2\delta$-4 polypeptide concentration of 0.6 pmol/$\mu$l), the optimal imidazole concentration can vary between 1 and 20 mM, with a concentration of about 10 mM being preferred. As mentioned previously, other compounds such as histidine as well as pH variations may be used to enhance radioligand binding.

The concentration of the radioligand is evaluated with respect to the concentration of $\alpha_2\delta$-2, $\alpha_2\delta$-3 or $\alpha_2\delta$-4 subunit polypeptide present in the assay medium. Generally, the concentration of radioligand varies from 1 nM to 100 nM. A preferred [$^3$H]gabapentin concentration is about 5 to 20 nM, with a most preferred concentration being about 10 nM. A preferred [$^3$H]leucine concentration is also about 5 to 20 nM, with a most preferred concentration being about 10 nM. It is to be noted that the concentration of other radioligands having affinities similar to those of [$^3$H]gabapentin and [$^3$H]leucine should also be in the range of about 5 to 20 nM.

Once the optimal radioligand binding conditions have been determined, a test ligand can be introduced in the assay medium to evaluate the level of displacement of the radioligand. The concentration of test ligand to be introduced in the assay medium usually varies from 0.1 nM to about 100 $\mu$M. A preferred test ligand concentration of about 10 $\mu$M is usually a starting point in a high throughput screening assay. Then, depending on the number of hits obtained, it may be lowered or increased.

The inventors have tested the displacement of a particular radioligand, [$^3$H]gabapentin, with (S+)-3-isobutly gaba. The data provided in the examples which follow clearly shows that the assay can be used in high throughput competition studies.

E) Purified Recombinant Secreted Soluble $\alpha_2\delta$-2, $\alpha_2\delta$-3 or $\alpha_2\delta$-4 Polypeptides Another object of the present invention consists of a purified or isolated recombinant polypeptide comprising the amino acid sequence of a secreted soluble $\alpha_2\delta$-2, $\alpha_2\delta$-3 or $\alpha_2\delta$-4 subunit polypeptide.

Preferred isolated recombinant polypeptides of the invention include those having at least 80%, preferably 90%, more preferably 95, and most preferably 98 or 99%, amino-acid identity with polypeptides comprising from amino acid 1 to between amino-acids 1027 and 1145, preferably between amino-acids 1062 and 1145 of SEQ ID NO:20, as well as those having at least 80%, preferably 90%, more preferably 95, and most preferably 98 or 99%, amino-acid identity with polypeptides comprising from amino acid 1 to between amino-acids 984 and 1085, preferably between amino-acids 1019 and 1085 of SEQ ID NO:22.

In a further preferred embodiment, the polypeptide comprises an amino acid sequence having at least 80%, preferably 90%, more preferably 95%, and most preferably 98% or 99% amino acid identity with the amino acid sequence of SEQ ID NO:4, SEQ ID NO:5, SEQ ID NO:6, SEQ ID NO:10, SEQ ID NO:11, SEQ ID NO:12, SEQ ID NO:16, SEQ ID NO:17 and SEQ ID NO:18.

F) Modified Secreted Soluble $\alpha_2\delta$-2, $\alpha_2\delta$-3 or $\alpha_2\delta$-4 Subunit Polypeptides The invention also relates to secreted soluble $\alpha_2\delta$-2, $\alpha_2\delta$-3 or $\alpha_2\delta$-4 subunit polypeptide comprising amino acid changes ranging from 1, 2, 3, 4, 5, 10, 20, 25, 30, 35, 40 substitutions, additions or deletions of one amino acid as regards to polypeptides of anyone of the amino acid sequences of the present invention. Preferred sequences are those of SEQ ID NO:4, SEQ ID NO:5, SEQ ID NO:6, SEQ ID NO:10, SEQ ID NO:11, SEQ ID NO:12, SEQ ID NO:16, SEQ ID NO:17 and SEQ ID NO:18.

In the case of an amino acid substitution in the amino acid sequence of a polypeptide according to the invention, one or several consecutive or non-consecutive amino-acids are replaced by "equivalent" amino-acids. The expression "equivalent" amino acid is used herein to designate any amino acid that may be substituted for one of the amino-acids belonging to the native protein structure without decreasing the binding properties of the corresponding peptides to the antibodies raised against the polypeptides of the invention. In other words, the "equivalent" amino-acids are those which allow the generation or the synthesis of a polypeptide with a modified sequence when compared to the amino acid sequence of the secreted soluble $\alpha_2\delta$-2, $\alpha_2\delta$-3 or $\alpha_2\delta$-4 subunit polypeptides of interest, said modified polypeptide being able to bind to the antibodies raised against the secreted soluble $\alpha_2\delta$-2, $\alpha_2\delta$-3 or $\alpha_2\delta$-4 subunit polypeptide of interest and/or to induce antibodies recognizing the parent polypeptide.

Alternatively, amino acid changes encompassed are those which will not abolish the biological activity of the resulting modified polypeptide. These equivalent amino-acids may be determined either by their structural homology with the initial amino-acids to be replaced, by the similarity of their net charge or of their hydrophobicity, and optionally by the results of the cross-immunogenicity between the parent peptides and their modified counterparts.

The peptides containing one or several "equivalent" amino-acids must retain their specificity and affinity properties to the biological targets of the parent protein, as it can be assessed by a ligand binding assay or an ELISA assay.

Examples of amino-acids belonging to specific classes include Acidic (Asp, Glu), Basic (Lys, Arg, His), Non-polar (Ala, Val, Leu, Ile, Pro, Met, Phe, Trp) or uncharged Polar (Gly, Seu, Thr, lys, Tyr, Asn, Gln) amino-acids.

Preferably, a substitution of an amino acid in $\alpha_2\delta$-2, $\alpha_2\delta$-3 or $\alpha_2\delta$-4 subunit polypeptide of the invention, or in a peptide fragment thereof, consists in the replacement of an amino acid of a particular class for another amino acid belonging to the same class.

By an equivalent amino acid according to the present invention is also contemplated the replacement of a residue in the L-form by a residue in the D form or the replacement of a Glutamic acid (E) residue by a Pyro-glutamic acid compound. The synthesis of peptides containing at least one residue in the D-form is, for example, described by Koch (1977).

A specific embodiment of a modified peptide of interest according to the present invention, includes, but is not limited to, a peptide molecule, which is resistant to proteolysis. This is a peptide in which the —CONH— peptide bond is modified and replaced by a ($CH_2NH$) reduced bond, a (NHCO) retro inverso bond, a ($CH_2$—O) methylene-oxy bond, a ($CH_2S$) thiomethylene bond, a ($CH_2CH_2$) carba bond, a (CO—$CH_2$) cetomethylene bond, a (CHOH—$CH_2$) hydroxyethylene bond), a (N—N) bound, a E-alcene bond or also a —CH═CH-bond. The invention also encompasses secreted soluble $\alpha_2\delta$-2, $\alpha_2\delta$-3 or $\alpha_2\delta$-4 subunit polypeptide in which at least one peptide bond has been modified as described above.

The polypeptides according to the invention may also be prepared by the conventional methods of chemical synthesis, either in a homogenous solution or in solid phase. As an illustrative embodiment of such chemical polypeptide synthesis techniques, it may be cited the homogenous solution technique described by Houbenweyl (1974).

The secreted soluble $\alpha_2\delta$-2, $\alpha_2\delta$-3 or $\alpha_2\delta$-4 subunit polypeptide of interest, or a fragment thereof may thus be prepared by chemical synthesis in liquid or solid phase by successive couplings of the different amino acid residues to be incorporated (from the N-terminal end to the C-terminal end in liquid phase, or from the C-terminal end to the N-terminal end in solid phase) wherein the N-terminal ends and the reactive side chains are previously blocked by conventional groups.

For solid phase synthesis, the technique described by Merrifield (1965a; 1965b) may be used in particular.

G) Antibody Production

The secreted soluble $\alpha_2\delta$-2, $\alpha_2\delta$-3 or $\alpha_2\delta$-4 subunit polypeptides of the invention and their peptide fragments of interest can be used for the preparation of antibodies. Polyclonal antibodies may be prepared by immunization of a mammal, especially a mouse or a rabbit, with a polypeptide according to the invention that is combined with an adjuvant of immunity, and then by purifying the specific antibodies contained in the serum of the immunized animal on an affinity chromatography column on which has previously been immobilized the polypeptide that has been used as the antigen.

Monoclonal antibodies may be prepared from hybridomas according to the technique described by Kohler and Milstein (1975).

The present invention also deals with antibodies produced by the trioma technique and by the human B-cell hybridoma technique, such as described by Kozbor et al. (1983).

Antibodies of the invention also include chimeric single chain Fv antibody fragments (U.S. Pat. No. 4,946,778; Martineau et al., (1998), antibody fragments obtained through phage display libraries Ridder et al. (1995) and humanized antibodies (Leger et al., (1997)).

H) Screening Assays

The invention concerns a method for the screening of ligands which bind soluble secreted $\alpha_2\delta$-2, $\alpha_2\delta$-3 or $\alpha_2\delta$-4 subunit polypeptide. More particularly, the targeted $\alpha_2\delta$-2, $\alpha_2\delta$-3 or $\alpha_2\delta$-4 subunit binding site is preferably the [$^3$H] gabapentin binding site. The various parameters of the method of the invention are described in further detail below.

EXAMPLES

Example 1

Construction of a Nucleotide Sequence Encoding a Soluble Secreted Human $\alpha_2\delta$-2 Subunit Polypeptide Deletion Mutant of SEQ ID NO:23 a) Primer Design

PCR primers were designed to generate the secreted soluble human $\alpha_2\delta$-2 deletion mutant of SEQ ID NO:23 as follows:

5' PCR primer: This was designed to engineer in a KOZAK translation initiation consensus sequence prior to the coding sequence (Kozak *JBC* 266 19867–19870)

3' PCR primer: This was designed to engineer in six histidine residues followed by a stop-codon at the desired location in the coding sequence. In addition to the stop codon the $\alpha_2\delta$-2 primers also included an Eco RI restriction site.

The bold region in each primer sequence denotes the 'tagged' region; addition of sequences not present in the template. Primers were custom synthesized by Perkin Elmer Applied Biosystems UK to the ABI ready pure grade, supplied lyophilized then resuspended to 15 μM in 10 mM TE. JB197 and 198 were provided with 5' phosphate groups:

5' Primer JB197 (5'-TCGCCACCATGGCGGTGCCGGCTC-3', SEQ ID NO:25).

3' Primer JB198 (5'-TCGGAATTCCTCAGTGATGGTGATGGTGATGGGCCCCGCGGCCACAGTC-3', SEQ ID NO:28).

b) Protocol for PCR Mediated 5' Kozak and 3' 6His Tagging of Human $\alpha_2\delta$-2

The full length human $\alpha_2\delta$-2 gene (Gen Bank Accession Number AF042792) in a pcDNA 3 vector as described in Brown, J. P. and Gee, N. S., Cloning and deletion mutagenesis of the $\alpha_2\delta$ calcium channel subunit from porcine cerebral cortex, *The journal of biological chemistry*, 273 (39):25458–25465) was used as the template in the following PCR reaction.

The reagents were added in the following order in triplicate to a 96 well PCR plate:

| | μl |
|---|---|
| 10× Pfx Amplification buffer | 5 |
| 10 mM dNTPs | 1.5 |
| 50 mM $MgSO_4$ | 1 |
| 15 μM JB197 | 1.5 |
| 15 μM JB198 | 1.5 |
| 100 ng/μl pcDNA3.1-humans-$\alpha_2\delta$-2 | 1 |
| 10× PCR Enhancer | 5 |
| $H_2O$ | 32.7 |
| 2.5 UNITS/μL PFX POLYMERASE | 0.8 μL |

The plate was the cycled on an MJ Tetrad DNA engine according to the following cycling conditions:

| | |
|---|---|
| 94° C./2 mins | |
| followed by: | |
| for 30 cycles | 94° C./45 sec |
| | 58° C./45 sec |
| | 68° C./4 mins |
| followed by: | |
| 68° C./10 mins | |
| followed by: | |
| hold at 4° C. | |

The 3366 bp product was then gel purified from a 1% TAE agarose gel using QIAEX beads and eluted in approximately 50 μl TE.

Example 2

Cloning of the PCR Fragments of Example 1 Into the Baculovirus Transfer Vector pFastBac1

The PCR products of Example 1 were cloned into StuI digested, calf intestinal phosphatase dephosphorylated, phenol chloroform extracted and QIAEX gel purified pFastBac1 (Life Technologies) using the Rapid DNA ligation kit (Roche Diagnostics) transforming XL1-blue ($\alpha_2\delta$-1b) *E. Coli* cells:

a) Screening for Positive Recombinants

Given that the PCR product was cloned by blunt-end ligation a screen was required to select a recombinant with the gene ligated in the positive orientation with respect to the polyhedrin promoter in pFastBac1. This was achieved by restriction digest of miniprep DNA (Qiagen miniprep kit) prepared from colony minicultures and analysis on a 1% TAE agarose gel. A positive clone was identified according to the following digest patterns:

| SEQ ID NO:23 in pFastBac1 Eco RI digest performed on miniprep DNA | Predicted fragments (bp) |
|---|---|
| PCR product cloned in a positive orientation | 4773 and 3368 |
| PCR product cloned in a negative orientation | 8127 and 14 |

b) Sequencing Analysis of Selected Clones

One positive was selected for this clone and used to prepare a plasmid DNA stock of the desired construct (QIAGEN maxi kit). Confirmatory sequence reactions were performed using the Big Dye terminator sequencing kit and run on an ABI 310 Prism Genetic Analyzer. Sequence analysis of both coding strands was performed using a selection of sequencing oligonucleotide primers.

Example 3

Protocol for Establishing Baculovrus Banks for the Expression of the $\alpha_2\delta$-2 Deletion Mutant SEQ ID NO:23

Essentially, the protocol used to generate the baculovirus banks is that outlined in the Life Technologies Bac-to Bac™ baculovirus expression systems manual.

a) Transposition of DH10Bac *E Coli* Cells

One ng (5 $\mu$l ) of the recombinant pFastBac-1 construct containing the nucleotide sequence encoding the porcine $\alpha_2\delta$-2 deletion mutant of SEQ ID NO:23 was added to 100 $\mu$l of DH10Bac cells thawed on ice. The cells were then mixed gently by tapping the tube then incubated on ice for 30 minutes before heat shock treatment by incubation in a 42° C. water bath for 45 seconds. The mixture was then chilled on ice for 2 minutes before the addition of 900 $\mu$l of S.O.C. medium. The mixture was then placed in a shaking incubator (200 rpm) at 37° C. for 4 hours. The cells were then serially diluted (10 fold dilutions from $10^{-1}$ to $10^{-3}$) and 10 $\mu$l of each dilution plated on LB agar plates containing 50 $\mu$g/ml kanamycin, 7 $\mu$g/ml gentamicin, 10 $\mu$g/ml tetracycline, 100 $\mu$g/ml Bluo-gal and 40 $\mu$g/ml IPTG. The plates were incubated at 37° C. for between 1 and 3 days until discrete colonies of blue and white colour were discernible.

b) Isolation of Recombinant DNA

White colonies (containing the recombinant bacmid) were picked and grown for 24 hours (to stationary phase) at 37° C. with shaking (200 rpm) in 2 ml of LB containing 50 $\mu$g/ml kanamycin, 7 $\mu$g/ml gentamicin and 10 $\mu$g/ml tetracycline. 1.5 ml of culture was then transferred to a microfuge tube and centrifuged at 14,000×g for 1 minute. The supernatant was removed and the cells resuspended gently in 0.3 ml of 15 mM Tris-HCl (pH8.0), 10 mM EDTA, 100 $\mu$g/ml RNase A. 0.3 ml of 0.2N NaOH, 1% SDS was then added and the mixture mixed gently before incubation at 22° C. for 5 minutes. Then 0.3 ml of 3M Potassium acetate (pH5.5) was added and the sample placed on ice for 10 minutes. After centrifugation at 14,000×g for 10 minutes the supernatant was transferred to a tube containing 0.8 ml of isopropanol, mixed then placed on ice for 10 minutes before centrifugation at 14,000×g for 10 minutes. The supernatant was then discarded and the pellet rinsed with 0.5 ml of 70% ethanol before centrifugation at 14,000×g for 5 minutes. This 70% ethanol rinse was then repeated before removing all of the supernatant and air drying the pellet for 10 minutes at room temperature. The pellet was finally resuspended in 40 $\mu$l of TE.

c) Transfection of sf9 Cells with the Recombinant Bacmid DNA

A 6-well tissue culture plate was seeded with $0.9\times10^6$ sf9 cells (cells at log phase having grown from a culture passaged at $0.3\times10^6$ cells/ml) per 35 mm well in 2 ml of Sf-900 II SFM media containing 50 units/ml penicillin and 50 $\mu$g/ml streptomycin. Cells were left to attach at 27° C. for 1 hour. Bacmid DNA prepared as described above (5 $\mu$l) was added to 200 $\mu$l of Sf-900 II SFM media containing 6 $\mu$l of CELLFECTIN and mixed before incubation at room temperature for 45 minutes. The cells were washed once with 2 ml of Sf-900 II SFM media without antibiotics then 0.8 ml of Sf-900 II SFM media was added to each tube containing the lipid-DNA complex. The wash buffer was removed from the cells and the 1 ml of diluted lipid-DNA complex overlaid on the cells. The cells were incubated for 5 hours at 27° C. after which time the transfection mixture was removed and 2 ml of Sf-900 II SFM media containing 50 units/ml penicillin and 50 $\mu$g/ml streptomycin was added. The cells were then incubated for 72 hours.

After incubation for 72 hours the media was removed from the cells and centrifuged at 500×g for 5 minutes. The supernatant was then transferred to a fresh tube, this was labelled as the P0 bank and stored at 4° C. in the dark. The P1 bank was prepared by passaging sf9 cells at approx $5\times10^6$ cells/ml to $2\times10^6$ cells/ml (100 ml in a 250 ml Erlenmeyer flask) and adding 0.5 ml of the P0 bank harvested above. The cells were then incubated shaking (200 rpm) at 27° C. for 4 days. Under sterile conditions the culture was centrifuged at 500×g for 10 minutes and the supernatant 0.2 $\mu$M filtered (P1 bank). The P2 bank was prepared by adding 2 ml of P1 bank per 400 ml culture (in 1L Erlenmeyer flasks) passaged as above to $2\times10^6$cells/ml. The culture was incubated as before for 4 days and the supernatant harvested and filtered as described for the P1 bank. The supernatant was first pooled then aliquoted (10 ml) and stored at 4° C.

Example 4

Expression of the $\alpha_2\delta$-2 Deletion Mutant of SEQ ID NO:23

To sf9 cells passaged from ~$5\times10^6$ cells/ml to 2×106 cells/ml in Sf-900 II SFM media was added 0.1 ml virus per 100 ml of cells of the appropriate viral bank (400 ml volumes in 1 L Erlenmeyer flasks). The cells were then cultured for 4–5 days at 27° C. with 110 rpm shaking. Expression of the protein was confirmed by SDS-PAGE and Western blotting using an anti penta-His monoclonal antibody (Qiagen) and was detected in the culture supernatant and cell lysate.

Example 5

Purification of $\alpha_2\delta$-2Deletion Mutant of SEQ ID NO:23

The $\alpha_2\delta$-2 deletion mutant of SEQ ID NO:23 was purified from the cell lysate following the purification strategy outlined below:

The culture was centrifuged at 6,000×g for 10 minutes and the supernatant removed. The weight of the cell pellet was determined before re-suspension in 20 mM Tris pH8.0, 100 mMKCl, 1% P40-Nonidet (100 ml per 20 g of wet cells). A protease inhibitor cocktail (Sigma, Cat# P8849), 1 ml/L, was added to the mixture. The solution was then stirred for 10 minutes before centrifugation for 1 hour at 30,000×g and 4° C. The supernatant was concentrated (30 kDa cut off) to approx. ~300 ml then centrifuged for 1 hour at 100,000×g.

Supernatant containing the soluble proteins was diluted 1:3 in 10 mM Tris-HCl pH8.0 (equilibration buffer) and loaded onto a pre-equilibrated Q-Sepharose column (2.5 cm i.d.×30 cm h.) at a flow rate of 900 ml/h. After washing with equilibration buffer until a stable $A_{280\ nm}$ baseline had been achieved, protein was eluted with 20 mM Tris-HCl pH8.0, 0.5M KCl, 10 mM Imidazole.

The eluate was then loaded onto a Ni-NTA (Qiagen) column (2.5 cm i.d.×6 cm h.) pre-equilibrated in 20 mM Tris pH8.0, 0.5M KCl, 10 mM imidazole at a flow rate of 2 ml/min. The column was washed successively with buffer A (20 mM Tris pH8.0, 0.5M KCl, 20 mM Imidazole), buffer B (100 mM Tris-HCl pH8.0, 1M KCl), and buffer A again. Elution was performed with buffer C (20 mM Tris-HCl pH8.0, 100 mM KCl, 0.5M Imidazole). The Ni-NTA eluate (~50 ml) was concentrated (30 kDa cut-off) to ~2 ml and applied at 1 ml/min and in 0.2 ml aliquots, to an FPLC Superdex-200 column equilibrated in 10 mM HEPES, pH7.4, 150 mM NaCl. Fractions containing the polypeptide of SEQ ID NO:23 were pulled.

Example 6

SPA Assay of [$^3$H]gabapentin Binding to the Secreted Soluble Human $\alpha_2\delta$-2 Subunit of SEQ ID NO:23

The assay is carried out at 21° C. Assay components are added in the following order (all reagents are diluted in 10 mM HEPES (pH 7.4 at 21° C.) to 96-well Optiplates:

| | |
|---|---|
| 25 μl | imidazole at various concentrations (diluted from a 1M stock pH 8.0, see assay details) |
| 50 μl | 10 mM HEPES pH 7.4 |
| 25 μl | (50 mg) SPA beads (Amersham) |
| 100 μl | s-$\alpha_2\delta$-2 subunit polypeptide of SEQ ID No 23 (2 μl protein diluted to 100 μl) |
| 25 μl | radioligand ([$^3$H]gabapentin obtained from example 5) |

Immediately after adding radioligand, the optiplates were loaded in the Packard Top Count scintillation counter to follow the binding time course. Imidazole was first used in the assay to optimize the specific interaction of the protein's 6His tag with the SPA bead. Imidazole itself (up to 100 mM) in the filtration assay has no effect on [$^3$H]gabapentin binding (n=1).

Example 7

Ni Flashplate Assay of [$^3$H]gabapentin Binding to Secreted Soluble Human $\alpha_2\delta$-2 Subunit of SEQ ID NO:23

Assays are carried out at 21° C. in a final volume of 250 μl in 96-well NEN Ni chelate flash plates. Assay components are added in the following order (all reagents were diluted in 10 mM HEPES (pH 7.4 at 21° C.)):

| | |
|---|---|
| 25 μl | 10 mM HEPES pH 7.4 |
| 25 μl | imidazole at various concentrations (diluted from a 1M stock pH 8.0, see assay details) |
| 75 μl | 10 mM HEPES pH 7.4 |
| 100 μl | s-$\alpha_2\delta$-2-6His (2 μl protein diluted to 100 μl) obtained from example 5 |
| 25 μl | radioligand ([$^3$H]gabapentin (65 Ci/mmole) |

Immediately after adding the radioligand, flash plates are loaded in the Packard Top Count scintillation counter to follow the binding time course. The '[$^3$H] flash plate' programme (cpm) is used to monitor activity. Imidazole is first used in the assay to optimize the specific interaction of the protein's 6His tag with the Ni flashplate.

Example 8

Ni Flasholate Assay of [$^3$H]Leucine Binding to Secreted Soluble Human $\alpha_2\delta$-2-6His The procedure described in example 7 is repeated, except that [$^3$H]gabapentin is replaced by 25 μl (10.1 nM) of [$^3$H]Leucine (41 Ci/mmole).

Example 9

Ni Flasbplate Assay Studying Competitive Binding of [$^3$H]gabapentin and (S+)-3-isobutyl GABA to Human $\alpha_2\delta$-2-6His (SEQ ID NO:23)

Assays are carried out at 21° C. in a final volume of 250 μl in 96-well NEN Ni chelate flash plates. Wells are set up for both 'total' and 'non-specific' binding. Specific binding is defined as that remaining after subtraction of the average of the 'non-specific binding' values from the average of the 'total' binding values. Assay components are added in the following order (all reagents were diluted in 10 mM HEPES (pH 7.4 at 21° C.)):

| | | |
|---|---|---|
| | 25 μl | 10 mM HEPES pH 7.4 or 25 μl of the test compound at the appropriate concentration in HEPES |
| | 25 μl | 200 mM imidazole (diluted from a 1M stock pH 8.0, see assay details) |
| Total binding | 75 μl | 10 mM HEPES pH 7.4 |
| Non-specific binding | 50 μl | 10 mM HEPES pH 7.4 and 25 μl 100 μM (S+)-3-isobutyl GABA |
| | 100 μl | $\alpha_2\delta$-2-6His (2 μl protein* diluted to 100 μl) |
| | 25 μl | radioligand ([$^3$H]gabapentin or [$^3$H]Leucine) |

*The source of $\alpha_2\delta$-2-6His is that purified by fplc Superdex-200 gel filtration (see example 5)

Immediately after adding radioligand, flash plates are loaded in the Packard Top Count scintillation counter to follow the binding time course. Incubation time before the assay is 3 hours. The '[$^3$H] flash plate' programme (cpm) is used to monitor activity Competition studies are compared across the flash-plate and filter binding methodologies in order to validate the new assay technology with the established filter binding methodology.

GraphPad Prism software is used to process competition curve data and determine $IC_{50}$ and hill slope values. Twelve point competition curves with half log dilution steps of test compounds are used in the experiments.

Example 10

Filter Binding Assay of [$^3$H]gabapentin Binding to the Recombinant Polypeptide of SEQ ID NO:23

Assays were carried out at 21° C. in a final volume of 250 μl in 96-deep well plates. Assay components were (all reagents were diluted in 10 mM HEPES (pH 7.4 at 21° C.)):

| | |
|---|---|
| 25 μl | compound to test |
| 200 μl | Polypeptide of SEQ ID NO:23 (3 μl protein diluted to 200 μl) |
| 25 μl | radioligand ([$^3$H]gabapentin (65 Ci/mmole) |

Plates were incubated at room temperature for 1 h prior to filtering on to 96-well GF/B Unifilter plates pre-soaked in 0.3% polyethylenimine. Filters were washed with 3×1 ml 50 mM Tris-HCl (pH 7.4 at 4° C.), and dried over-night. Scintillant (Microscint O, 50 μl) was added and the plates counted using a Packard Top Count scintillation counter. Specific binding was ~98% of the 'total' value. In [$^3$H] gabapentin saturation studies, the $K_D$ (nM) obtained was about 10.62. Table 2 below provides the results of the competition studies.

Example 11

Construction of a Nucleotide Sequence Encoding a Soluble Secreted Mouse $\alpha_2\delta$-3 Deletion Mutant of SEQ ID NO:25 as Follows a) Primer Design PCR primers were designed to generate the secreted soluble mouse $\alpha_2\delta$-3 deletion mutant of SEQ ID NO:25 as follows:

5' PCR primer: This was designed to engineer in a KOZAK translation initiation consensus sequence prior to the coding sequence (Kozak *JBC* 266 19867–19870)

3' PCR primer: This was designed to engineer in six histidine residues followed by a stop-codon at the desired location in the coding sequence. In addition to the stop codon the $\alpha_2\delta$-3 primers also included an Eco RI restriction site.

The bold region in each primer sequence denotes the 'tagged' region; addition of sequences not present in the template. Primers were custom synthesized by Perkin Elmer Applied Biosystems UK to the ABI ready pure grade, supplied lyophilized then resuspended to 15 μM in 10 mM TE. JB201 and 202 were provided with 5' phosphate groups:

5' Primer JB201 (5'-TCGCCACCATGGCCGGGCCGGGC-3', SEQ ID NO:27)

3' Primer JB202 (5'-TCTCAGTGATGGTGATGGTGATGCGATGCACCCCCACACTCTC-3', SEQ ID NO:28)

b) Protocol for PCR Mediated 5' Kozak and 3' 6His Tagging of Mouse $\alpha_2\delta$-3

The full length mouse $\alpha_2\delta$-3 gene (Gen Bank Accession number AJ010949) in the pcDNA3 vector as described in Brown, J. P. and Gee, N. S., Cloning and deletion mutagenesis of the Δ2δ calcium channel subunit from porcine cerebral cortex, *The journal of biological chemistry*, 273 (39):25458–25465) was used as the template in the following PCR reaction.

The reagents were added in the following order in triplicate to a 96 well PCR plate:

| | μl |
|---|---|
| 10× Pfx Amplification buffer | 5 |
| 10 mM dNTPs | 1.5 |
| 50 mM $MgSO_4$ | 1 |
| 15 μM JB201 | 1.5 |
| 15 μM JB202 | 1.5 |
| 100 ng/μl pcDNA3-mouse-$\alpha_2\delta$-3 | 1 |
| 10× PCR Enhancer | 5 |
| $H_2O$ | 32.7 |
| 2.5 UNITS/μL PFX POLYMERASE | 0.8 μL |

The plate was the cycled on an MJ Tetrad DNA engine according to the following cycling conditions:

| | |
|---|---|
| 94° C./2 mins | |
| followed by: | |
| for 30 cycles | 94° C./45 sec |
| | 60° C./45 sec |
| | 68° C./4 mins |
| followed by: | |
| 68° C./10 mins | |
| followed by: | |
| hold at 4° C. | |

The 3244 bp product was then gel purified from a 1% TAE agarose gel using QIAEX beads and eluted in approximately 50 μl.

The truncated protein of SEQ ID N°24 was expressed such the procedure of example 2,3 and 4.

REFERENCES

Perez-Reyes, E., and Schneider, T. (1994) *Drug Dev. Res.* 33, 295–318

Catterall, W. A. (1995) *Annu. Rev. Biochem.* 64, 493–531

Birnbaumer, L., Campbell, K. P., Catterall, W. A., Harpold, M. M., Hoffman, F., Horne, W. A., Mori, Y., Schwartz, A, Snutch, T. P., Tanabe, T., and Tsien, R. W. (1994) *Neuron* 13, 505–506

Brust, P. F., Simerson, S., McCue, A. F., Deal, C. R., Schoonmaker, S., Williams, M. E., Velicelebi, G., Johnson, E. C., Harpold, M. M., and Ellis, S. B. (1993) *Neuropharmacology* 32, 1089–1102

Itagaki, K., Koch, W. J., Bodi, L, Klockner, U., Slish, D. F., and Schwartz, A. (1992) *FEBS Lett.* 297, 221–225

Mikami, A, Imoto, F_Tanabe, T., Niidome, T., Mori, Y., Takeshima, H., Narumiya, S., and Numa, S. (1989) *Nature* 340, 230–233

Mori, Y., Friedrich, T., Kim, M. S., Mikami, A., Nakai, J., Ruth, P., Bosse, E., Hofmann, F., Flockerzi, V., Furuichi, T., Mikoshiba, K., Imoto, K, Tanabe, T., and Numa, S. (1991) *Nature* 350, 398–402

Singer, D., Biel, M., Lotan, I., Flockerzi, V., Hofmann, F., and Dascal, N. (1991) *Science* 253, 1553–1657

Ramsay, R. E. (1994) *Neurology* 44, Suppl. 5, 23–30

Watson, W. P., and Little, H. J. (1995) *Br. J. Pharmacol.* 116, 33P (abstr.)

Singh, L., Field, M. J., Ferris, P., Hunter, J. C., Oles, R. J., Williams, R. G., and Woodruff, G. N. (1996) *Psychopharmacology* 127, 1–9

Xiao, W. H., and Bennet, G. L (1995) *Soc. Neurosci.* 21, 897 (abstr.)

Mellick, G. A., Mellicy, L. B., and Mellick, L. B. (1995) *J. Pain Symptom Manage.* 10, 265–266

Shimoyama, N., Shimoyama, M., Davis, A. M., Inturrisi, C. E., and Elliott, K. J. (1997) *Neurosci. Lett.* 222, 65–67

SegaL A. Z., and Rordorf, G. (1996) *Neurology* 46, 1175–1176

Mellick, G. A., and Mellick, L. B. (1996) *Sleep* 19, 224–226

Patel, J., and Naritoku, D. K (1996) *Clin. Neuropharmacol.* 19,185–188

Suman Chauhan, N., Webdale, L., Hill, D. R., and Woodruff, G. N. (1993) *Eur, J. Pharmacol.* 244, 293–301

Macdonald, R. L., and Kelly, F_M. (1993) *Epilepsia* 34, Suppl. 5, S1–S8

Taylor, C. P. (1994) *Neurology* 44, Suppl. 5, 10–16

Gotz, E., Feuerstein, T. J., Lais, A., and Meyer, D. K (1993) *Arzneimittelforschung* 43, 636–638

Loscher, W., Honack, D., and Taylor, C. P. (1991) *Neurosci. Lett.* 128,150–154

Honmou, O., Knesis, J. D., and Richerson, G. B. (1995) *Epilepsy Res.* 20, 193–202

Honmou, O., Oyelese, A. A., and Kocsis, J. D. (1995) *Brain Res.* 692,273–277

Petroff, O. A. C., Rothman, D. L., Behar, K. L., Lamoureux, D., and Mattson, R. H. (1996) *Ann. Neurol.* 39, 95–99

Reimann, W. (1983) *Eur. J. Pharmacol.* 94, 341–344

Dooley, D. J., Bartoszyk, G. D., Hartenstein, J., Reimann, W., Rock, D. M., and Satzinger, G. (1986) *Golden Jubilee Conference and Northern European Epilepsy Meeting.* Abstracts, University of York, UK, September 1986 (Abstract 8).

Thurlow, R. J., Brown, J. P., Gee, N. S., Hill, D. R., and Woodruff, G. N. (1993) *Eur. J. Pharmacol.* 247,341–345

Gee, N. S., Brown, J. P., Dissanayake, V. U. I., Offord, J., Thurlow, R., and Woodruff, G. N. (1996) *J. Biol. Chem.* 271, 5768–5776

Dissanayake, V. U. I-, Gee, N. S., Brown, J. P., and Woodruff, G. N. (1997) *Br. J. Pharmacol.* 120, 833–840

Taylor, C. P., Vartanian, M. G., Yuen, P. W., Bigge, C., Suman Chauhan, N., and Hill, D. R. (1993) *Epilepsy Res.* 14,11–15

Rock, D. M., Kelly, K. M., and Macdonald, R. L. (1993) *Epilepsy Res.* 16, 89–98

Wamil, A. W., Mclean, M. J., Nashville, T. N., and Taylor, C. P. (1991) *Neurology* 41, Suppl. 1, 140 (abstr.)

De Jongh, K S., Warner, C., and Catterall, W. A. (1990) *J. Biol. Chem.* 265, 14738–14741

Jay, S. D., Sharp, A. H., Kahl, S. D., Vedvick, T. S., Harpold, M. M., and Campbell, K. P. (1991) *J. Biol. Chem.* 266, 3287–3293

Burgess, A. J., and Norman, R. I. (1988) *Eur. J. Biochem.* 178, 527–533

Ellis, S. B., Williams, M. E., Ways, N. R., Brenner, R., Sharp, A. H., Leung, A. T., Campbell, K. P., McKenna, E., Koch, W. J., Hai, A., Schwartz, A., and Harpold, M. M. (1988) *Science* 241, 1661–1664

Brickley, K., Campbell, V., Berrow, N., Leach, R., Norman, R. I., Wray, D., Dolphin, A. C., and Baldwin, S. A- (1995) *FEBS Lett.* 364,129–133

Brice, N. L., Berrow, N. S., Campbell, V., Page, K. M., Brickley, K., Tedder, I., Dolphin, A C. (1997) *Eur. J. Neurosci.* 9, 749–759

Wiser, O., Trus, M., Tobi, D., Halevi, S., Giladi, E., and Atlas, D. (1996) *FEBS Lett.* 379,15–20

Xu, X., and Arnason, U. (1994) *Gene* (Amst.) 148, 357–362

Williams, M. E., Feldman, D. H., McCue, A. F., Brenner, R., Velicelebi, G., Ellis, S. B., and Harpold, M. M. (1992) *Neuron* 8, 71–84

Kim, H. L., Kim, H., Lee, P., King, R. G., and Chin, H. (1992) *Proc. Natl. Acad Sci. U. S. A.* 89,3251–3255

Brown, J. P., Dissanayake, V. U. K., Briggs, A. R., Milic, M. R., and Gee, N. S. (1998) *Anal. Biochem.* 255, 236–243

Higuchi, R. (1990) in *PCR Protocols: A Guide to Methods and Applications* (Innis, M. A., Gelfand, D. H., Sninsky, J. J., and White, T. J. eds) pp. 177–183, Academic Press, Ltd., London Bradford, M. M. (1976) *Anal. Biochem.* 72, 248–252

Kyte, J., and Doolittle, F. (1982) *J. Mol. Biol.* 157, 105–132

Summers, M. F., Henderson, L. E., Chance, M. R., Bess, J. W., Jr., South, T. L., Blake, P. R., Sagi, I., Perez-Alvarado, G., Sowder, R. C., Hare, D. R., and Arthur, L. O. (1992) *Protein Sci.* 1, 563–574

Klug, A. and Rhodes, D. (1987) *Trends. Biochem. Sci.* 12, 464–469

Pieler, T., and Bellefroid, E. (1994) *Mol. Biol. Rep.* 20, 1–8

Preston, R. A., Manolson, M. F., Becherer, M, Weidenhammer, E., Kirkpatrick, D., Wright, R, and Jones, E. W. (1991) *Mol. Cell, Biol.* 11, 5801–5812

Tan, X., Waterham, H. R., Veenhuis, M., and Cregg, J. M. (1995) *J. Cell Biol.* 128, 307–319

Scotland, P. B., Colledge, M., Melnikova, I., Dai, Z., and Froehner, S. C. (1993) *J. Cell Biol.* 123, 719–728

Henderson, L. E., Copeland, T. D., Sowder, R. C., Smythers, G. W., and Oroszlan, S. (1981) *J. Biol. Chem.* 256, 8400–8406

Beaucage et al., *Tetrahedron Lett* (1981) 22: 1859–1862.

Brown El., Belagaje R, Ryan M J, Khorana H G, *Methods Enzymol* (1979); 68, 109–151.

Feldman and Steg, (1996) *Medecine/Sciences, synthese*, 12, 47–55.

Houbenweyl, (1974), in *Meuthode der Organischen Chemie*, E. Wunsch Ed., Volume 15-I et 15-II, Thieme, Stuttgart.

Koch Y. (1977), *Biochem. Biophys. Res. Commun.*, 74, 488–491.

Kohler G. and Milstein C., (1975) *Nature*, 256, 495.

Kozbor et al., (1983) *Hybridoma*, 2(1), 7–16.

Leger O J, et al. (1997) *Hum Antibodies*, 8(1), 3–16.

Martineau P, Jones P, Winter G. (1998), *J. Mol Biol*, 280(1), 117–127.

Merrifield R B, 1965a, *Nature*, 207(996), 522–523.

Merrifield R B, 1965b, *Nature*, 207 (996), 22–523.

Narang S A, Hsiung H M, Brousseau R, *Methods Enzymol* 1979, 68, 90–98.

Ohno et al., (1994), *Science*, 265, 781–784.

O'Reilly et al., (1992) Baculovirus expression vectors: a Laboratory Manual. W. H. Freeman and Co., New York.

Ridder R Schmitz R, Legay F, Gram H, (1995) *Biotechnology* (NY), 13(3), 255–260.

Smith et al., (1983), *Mol. Cell. Biol.*, 3, 2156–2165.

Sternberg N. L. (1992), *Trends Genet*, 8, 1–16.

Sternberg N. L. (1994) *Mamm. Genome*, 5, 397–404.

Sambrook, J. Fritsch, E. F. and T. Maniatis (1989). Molecular cloning: a laboratory manual, 2ed. Cold Spring Harbor Laboratory, Cold Spring Harbor, N.Y.

Sanchez-Pescador R., (1988), *J. Clin. Microbiol.*, 26(10), 1934–1938.

Urdea et al., M S (1988) *Nucleic Acids Research*, 11, 4937–4957.

Urdea et al., M S (1991) *Nucleic Acids Symp Ser.*, 24, 197–200.

What is claimed is:

1. A purified or isolated nucleic acid encoding a secreted soluble calcium channel subunit polypeptide that binds gabapentin said nucleic acid consisting of a polynucleotide sequence encoding;

from amino-acid 1 to between amino-acids 1027 and 1062 of SEQ ID NO:20, or from amino-acid 1 to between amino-acids 984 and 1019 of SEQ ID NO:22.

2. A purified or isolated nucleic acid encoding a secreted soluble calcium channel subunit polypeptide that binds gabapentin wherein the sequence of said nucleic acid sequence encodes:

a polypeptide consisting of from amino-acid 1 to between amino-acids 1047 and 1062 of SEQ ID NO:20, or from amino-acid 1 to between amino-acids 1004 and 1019 of SEQ ID NO:22.

3. A purified or isolated nucleotide sequence encoding a secreted soluble calcium channel subunit polypeptide wherein said sequence consists of the sequence of SEQ ID NO:1, SEQ ID NO:2, SEQ ID NO:3, SEQ ID NO:7, SEQ ID NO:8, SEQ ID NO:9, SEQ ID NO:13, SEQ ID NO:14, or SEQ ID NO:15.

4. A recombinant vector comprising a nucleic acid according to claim 1.

5. A recombinant host cell comprising a nucleic acid according to claim 1.

6. A method for producing a secreted soluble calcium channel subunit polypeptide, said method comprises the steps of:

(a) inserting the nucleic acid according to claim 1 in an appropriate vector;

(b) culturing, in an appropriate culture medium, a host cell previously transformed or transfected with the recombinant vector of step (a);

(c) harvesting the culture medium thus obtained or lyse the host cell, for example by sonication or osmotic shock;

(d) separating or purifying, from said culture medium, or from the pellet of the resultant host cell lysate, the thus produced calcium channel subunit polypeptide of interest.

7. The nucleic acid of claim 1, said nucleic acid consisting of a polynucleotide sequence encoding a polypeptide from amino-acid 1 to between amino-acids 1027 and 1062 of SEQ ID NO:20.

8. The nucleic acid of claim 1, said nucleic acid consisting of a polynucleotide sequence encoding a polypeptide from amino-acid 1 to between amino-acids 984 and 1019 of SEQ ID NO:22.

9. The nucleic acid of claim 2, wherein said nucleic acid sequence encodes a polypeptide consisting of from amino-acid 1 to between amino-acids 1047 and 1062 of SEQ ID NO:20.

10. The nucleic acid of claim 2, wherein said nucleic acid sequence encodes a polypeptide consisting of from amino-acid 1 to between amino-acids 1004 and 1019 of SEQ ID NO:22.

11. The nucleotide sequence of claim 3, wherein said sequence consists of the sequence of SEQ ID NO:1, SEQ ID NO:2, or SEQ ID NO:3.

12. The nucleotide sequence of claim 3, wherein said sequence consists of the sequence of SEQ ID NO:7, SEQ ID NO:8, or SEQ ID NO:9.

13. The nucleotide sequence of claim 3, wherein said sequence consists of the sequence of SEQ ID NO:13, SEQ ID NO:14, or SEQ ID NO:15.

14. A purified or isolated nucleic acid consisting of a nucleic acid that encodes a polypeptide tag fused to a calcium channel subunit polypeptide consisting of:

from amino-acid 1 to between amino-acids 1027 and 1062 of SEQ ID NO:20, or from amino-acid 1 to between amino-acids 984 and 1019 of SEQ ID NO:22.

15. The purified or isolated nucleic acid of claim 14, wherein said calcium channel subunit is a polypeptide from amino-acid 1 to between amino-acids 1027 and 1062 of SEQ ID NO:20.

16. The purified or isolated nucleic acid of claim 14, wherein said calcium channel subunit is a polypeptide from amino-acid 1 to between amino-acids 984 and 1019 of SEQ ID NO:22.

17. A purified or isolated nucleic acid consisting of a nucleic acid that encodes a polypeptide tag fused to a calcium channel subunit polypeptide consisting of from amino-acid 1 to between amino-acids 1047 and 1062 of SEQ ID NO:20, or from amino-acid 1 to between amino-acids 1004 and 1019 of SEQ ID NO:22.

18. The purified or isolated nucleic acid of claim 17, wherein said calcium channel subunit polypeptide consists of from amino-acid 1 to between amino-acids 1047 and 1062 of SEQ ID NO:20.

19. The purified or isolated nucleic acid of claim 17, wherein said calcium channel subunit polypeptide consists of from amino-acid 1 to between amino-acids 1004 and 1019 of SEQ ID NO:22.

20. A purified or isolated nucleotide sequence consisting of a nucleic acid that encodes a polypeptide tag fused to a nucleic acid encoding a calcium channel subunit polypeptide selected from the group consisting of the nucleic acid sequences of SEQ ID NO:1, SEQ ID NO:2, SEQ ID NO:3, SEQ ID NO:7, SEQ ID NO:8, SEQ ID NO:9, SEQ ID NO:13, SEQ ID NO:14, and SEQ ID NO:15.

21. The nucleic acid of claim 19, wherein said nucleic acid encoding a calcium channel subunit polypeptide is selected from the group consisting of the sequence of SEQ ID NO:1, SEQ ID NO:2, and SEQ ID NO:3.

22. The nucleic acid of claim 19, wherein said nucleic acid encoding a calcium channel subunit polypeptide is selected from the group consisting of the sequence of SEQ ID NO:7, SEQ ID NO:8, and SEQ ID NO:9.

23. The nucleic acid of claim 19, wherein said nucleic acid encoding a calcium channel subunit polypeptide is selected from the group consisting of the sequence of SEQ ID NO:13, SEQ ID NO:14, and SEQ ID NO:15.

* * * * *

SEQUENCE LISTING

<160> NUMBER OF SEQ ID NOS: 28

<210> SEQ ID NO 1
<211> LENGTH: 3186
<212> TYPE: DNA
<213> ORGANISM: Homo sapiens

<400> SEQUENCE: 1

```
atggcggtgc cggctcggac ctgcggcgcc tctcggcccg gcccagcgcg gactgcgcgc     60
ccctggcccg gctgcggccc ccaccctggc cccggcaccc ggcgcccgac gtccgggccc    120
ccgcgcccgc tgtggctgct gctgccgctt ctaccgctgc tcgccgcccc cggcgcctct    180
gcctacagct tcccccagca gcacacgatg cagcactggg cccggcgtct ggagcaggag    240
gtcgacggcg tgatgcggat ttttggaggc gtccagcagc tccgtgagat ttacaaggac    300
aaccggaacc tgttcgaggt acaggagaat gagcctcaga agttggtgga gaaggtggca    360
ggggacattg agagccttct ggacaggaag gtgcaggccc tgaagagact ggctgatgct    420
gcagagaact tccagaaagc acaccgctgg caggacaaca tcaaggagga agacatcgtg    480
tactatgacg ccaaggctga cgctgagctg gacgaccctg agagtgagga tgtggaaagg    540
gggtctaagg ccagcaccct aaggctggac ttcatcgagg acccaaactt caagaacaag    600
gtcaactatt catacgcggc tgtacagatc cctacggaca tctacaaagg ctccactgtc    660
atcctcaatg agctcaactg gacagaggcc ctggagaatg tgttcatgga aaaccgcaga    720
caagacccca cactgctgtg gcaggtcttc ggcagcgcca caggagtcac tcgctactac    780
ccggccaccc cgtggcgagc ccccaagaag atcgacctgt acgatgtccg aaggagaccc    840
tggtatatcc agggggcctc gtcacccaaa gacatggtca tcatcgtgga tgtgagtggc    900
agtgtgagcg gcctgaccct gaagctgatg aagacatctg tctgcgagat gctggacacg    960
ctgtctgatg atgactatgt gaatgtggcc tcgttcaacg agaaggcaca gcctgtgtca   1020
tgcttcacac acctggtgca ggccaatgtg cgcaacaaga aggtgttcaa ggaagctgtg   1080
cagggcatgg tggccaaggg caccacaggc tacaaggccg gctttgagta tgcctttgac   1140
cagctgcaga actccaacat cactcgggcc aactgcaaca agatgatcat gatgttcacg   1200
gatggtggtg aggaccgcgt gcaggacgtc tttgagaagt acaattggcc aaaccggacg   1260
gtgcgcgtgt ttactttctc cgtggggcag cataactatg acgtcacacc gctgcagtgg   1320
atggcctgtg ccaacaaagg ctactatttt gagatccctt ccatcggagc catccgcatc   1380
aacacacagg aatatctaga tgtgttgggc aggcccatgg tgctggcagg caaggaggcc   1440
aagcaggttc agtggaccaa cgtgtatgag gatgcactgg gactggggtt ggtggtaaca   1500
gggaccctcc ctgttttcaa cctgacacag gatggccctg ggaaaaagaa gaaccagctg   1560
atcctgggcg tgatgggcat tgacgtggct ctgaatgaca tcaagaggct gacccccaac   1620
tacacgcttg gagccaacgg ctatgtgttt gccattgacc tgaacggcta cgtgttgctg   1680
caccccaatc tcaagcccca gaccaccaac ttccgggagc ctgtgactct ggacttcctg   1740
gatgcggagc tagaggatga gaacaaggaa gagatccgtc ggagcatgat tgatggcaac   1800
aagggccaca agcagatcag aacgttggtc aagtccctgg atgagaggta catagatgag   1860
gtgacacgga actacacctg ggtgcctata aggagcacta actacagcct ggggctggtg   1920
ctcccaccct acagcacctt ctacctccaa gccaatctca gtgaccagat cctgcaggtc   1980
aagtattttg agttcctgct ccccagcagc tttgagtctg aaggacacgt tttcattgct   2040
```

```
cccagagagt actgcaagga cctgaatgcc tcagacaaca acaccgagtt cctgaaaaac   2100
tttattgagc tcatggagaa agtgactcca gactccaagc agtgcaacaa cttccttctg   2160
cacaacctga tcttggacac gggcatcacg cagcagctgg tagagcgtgt gtggagggac   2220
caggatctca acacgtacag cctactggcc gtgttcgctg ccacagacgg tggcatcacc   2280
cgagtcttcc ccaacaaggc agctgaggac tggacagaga accctgagcc cttcaatgcc   2340
agcttctacc gccgcagcct ggataaccac ggttatgtct tcaagccccc acaccaggat   2400
gccctgttaa ggccgctgga gctggagaat gacactgtgg gcatcctcgt cagcacagct   2460
gtggagctca gcctaggcag gcgcacactg aggccagcag tggtgggcgt caagctggac   2520
ctagaggctt gggctgagaa gttcaaggtg ctagccagca accgtaccca ccaagaccag   2580
cctcagaagt gcggccccaa cagccactgt gagatggact gcgaggttaa caatgaggac   2640
ttactctgtg tcctcattga tgatggagga ttcctggtgc tgtcaaacca gaaccatcag   2700
tgggaccagg tgggcaggtt cttcagtgag gtggatgcca acctgatgct ggcactctac   2760
aataactcct tctacacccg caaggagtcc tatgactatc aggcagcctg tgcccctcag   2820
ccccctggca acctgggtgc tgcaccccgg ggtgtctttg tgcccaccgt tgcagatttc   2880
cttaacctgg cctggtggac ctctgctgcc gcctggtccc tgttccagca gcttctctac   2940
ggcctcatct accacagctg gttccaagca gaccccgcgg aggccgaggg gagccccgag   3000
acgcgcgaga gcagctgcgt catgaaacag acccagtact acttcggctc ggtaaacgcc   3060
tcctacaacg ccatcatcga ctgcggaaac tgctccaggc tgttccacgc gcagagactg   3120
accaacacca atcttctctt tgtggtggcc gagaagccgc tgtgcagcca gtgcgaggct   3180
ggccgg                                                              3186
```

<210> SEQ ID NO 2
<211> LENGTH: 3248
<212> TYPE: DNA
<213> ORGANISM: Homo sapiens

<400> SEQUENCE: 2

```
atggcggtgc cggctcggac ctgcggcgcc tctcggcccg gcccagcgcg gactgcgcgc     60
ccctggcccg gctgcggccc ccaccctggc cccggcaccc ggcgcccgac gtccgggccc    120
ccgcgcccgc tgtggctgct gctgccgctt ctaccgctgc tcgccgcccc cggcgcctct    180
gcctacagct tcccccagca gcacacgatg cagcactggg cccggcgtct ggagcaggag    240
gtcgacggcg tgatgcggat ttttggaggc gtccagcagc tccgtgagat ttacaaggac    300
aaccggaacc tgttcgaggt acaggagaat gagcctcaga agttggtgga gaaggtggca    360
ggggacattg agagccttct ggacaggaag gtgcaggccc tgaagagact ggctgatgct    420
gcagagaact tccagaaagc acaccgctgg caggacaaca tcaaggagga agacatcgtg    480
tactatgacg ccaaggctga cgctgagctg gacgaccctg agagtgagga tgtggaaagg    540
gggtctaagg ccagcaccct aaggctggac ttcatcgagg acccaaactt caagaacaag    600
gtcaactatt catacgcggc tgtacagatc cctacggaca tctacaaagg ctccactgtc    660
atcctcaatg agctcaactg gacagaggcc ctggagaatg tgttcatgga aaaccgcaga    720
caagacccca cactgctgtg gcaggtcttc ggcagcgcca caggagtcac tcgctactac    780
ccggccaccc cgtggcgagc ccccaagaag atcgacctgt acgatgtccg aaggagaccc    840
tggtatatcc agggggcctc gtcacccaaa gacatggtca tcatcgtgga tgtgagtggc    900
```

-continued

```
agtgtgagcg gcctgaccct gaagctgatg aagacatctg tctgcgagat gctggacacg    960
ctgtctgatg atgactatgt gaatgtggcc tcgttcaacg agaaggcaca gcctgtgtca   1020
tgcttcacac acctggtgca ggccaatgtg cgcaacaaga aggtgttcaa ggaagctgtg   1080
cagggcatgg tggccaaggg caccacaggc tacaaggccg gctttgagta tgcctttgac   1140
cagctgcaga actccaacat cactcgggcc aactgcaaca agatgatcat gatgttcacg   1200
gatggtggtg aggaccgcgt gcaggacgtc tttgagaagt acaattggcc aaaccggacg   1260
gtgcgcgtgt ttactttctc cgtggggcag cataactatg acgtcacacc gctgcagtgg   1320
atggcctgtg ccaacaaagg ctactatttt gagatccctt ccatcggagc catccgcatc   1380
aacacacagg aatatctaga tgtgttgggc aggcccatgg tgctggcagg caaggaggcc   1440
aagcaggttc agtggaccaa cgtgtatgag gatgcactgg gactggggtt ggtggtaaca   1500
gggaccctcc ctgttttcaa cctgacacag gatggccctg ggaaaagaa gaaccagctg    1560
atcctgggcg tgatgggcat tgacgtggct ctgaatgaca tcaagaggct gacccccaac   1620
tacacgcttg gagccaacgg ctatgtgttt gccattgacc tgaacggcta cgtgttgctg   1680
caccccaatc tcaagcccca gaccaccaac ttccgggagc ctgtgactct ggacttcctg   1740
gatgcggagc tagaggatga gaacaaggaa gagatccgtc ggagcatgat tgatggcaac   1800
aagggccaca agcagatcag aacgttggtc aagtccctgg atgagaggta catagatgag   1860
gtgacacgga actacacctg ggtgcctata aggagcacta actacagcct ggggctggtg   1920
ctcccaccct acagcacctt ctacctccaa gccaatctca gtgaccagat cctgcaggtc   1980
aagtattttg agttcctgct ccccagcagc tttgagtctg aaggacacgt tttcattgct   2040
cccagagagt actgcaagga cctgaatgcc tcagacaaca acaccgagtt cctgaaaaac   2100
tttattgagc tcatggagaa agtgactcca gactccaagc agtgcaacaa cttccttctg   2160
cacaacctga tcttggacac gggcatcacg cagcagctgg tagagcgtgt gtggagggac   2220
caggatctca acacgtacag cctactggcc gtgttcgctg ccacagacgg tggcatcacc   2280
cgagtcttcc ccaacaaggc agctgaggac tggacagaga accctgagcc cttcaatgcc   2340
agcttctacc gccgcagcct ggataaccac ggttatgtct tcaagccccc acaccaggat   2400
gccctgttaa ggccgctgga gctggagaat gacactgtgg gcatcctcgt cagcacagct   2460
gtggagctca gcctaggcag gcgcacactg aggccagcag tggtgggcgt caagctggac   2520
ctagaggctt gggctgagaa gttcaaggtg ctagccagca accgtaccca ccaagaccag   2580
cctcagaagt gcggccccaa cagccactgt gagatggact gcgaggttaa caatgaggac   2640
ttactctgtg tcctcattga tgatggagga ttcctggtgc tgtcaaacca gaaccatcag   2700
tgggaccagg tgggcaggtt cttcagtgag gtggatgcca acctgatgct ggcactctac   2760
aataactcct tctacacccg caaggagtcc tatgactatc aggcagcctg tgcccctcag   2820
ccccctggca acctgggtgc tgcaccccgg ggtgtctttg tgcccaccgt tgcagatttc   2880
cttaacctgg cctggtggac ctctgctgcc gcctggtccc tgttccagca gcttctctac   2940
ggcctcatct accacagctg gttccaagca gaccccgcgg aggccgaggg gagccccgag   3000
acgcgcgaga gcagctgcgt catgaaacag acccagtact acttcggctc ggtaaacgcc   3060
tcctacaacg ccatcatcga ctgcggaaac tgctccaggc tgttccacgc gcagagactg   3120
accaacacca atcttctctt tgtggtggcc gagaagccgc tgtgcagcca gtgcgaggct   3180
ggccggctgc tgcagaagga gacgcactgc ccagcggacg gcccggagca gtgtgagcta   3240
gtgcagag                                                             3248
```

-continued

<210> SEQ ID NO 3
<211> LENGTH: 3327
<212> TYPE: DNA
<213> ORGANISM: Homo sapiens

<400> SEQUENCE: 3

```
atggcggtgc cggctcggac ctgcggcgcc tctcggcccg gcccagcgcg gactgcgcgc     60
ccctggcccg gctgcggccc ccaccctggc cccggcaccc ggcgcccgac gtccgggccc    120
ccgcgcccgc tgtggctgct gctgccgctt ctaccgctgc tcgccgcccc cggcgcctct    180
gcctacagct tcccccagca gcacacgatg cagcactggg cccggcgtct ggagcaggag    240
gtcgacggcg tgatgcggat ttttggaggc gtccagcagc tccgtgagat ttacaaggac    300
aaccggaacc tgttcgaggt acaggagaat gagcctcaga agttggtgga gaaggtggca    360
ggggacattg agagccttct ggacaggaag gtgcaggccc tgaagagact ggctgatgct    420
gcagagaact tccagaaagc acaccgctgg caggacaaca tcaaggagga agacatcgtg    480
tactatgacg ccaaggctga cgctgagctg gacgaccctg agagtgagga tgtggaaagg    540
gggtctaagg ccagcaccct aaggctggac ttcatcgagg acccaaactt caagaacaag    600
gtcaactatt catacgcggc tgtacagatc cctacggaca tctacaaagg ctccactgtc    660
atcctcaatg agctcaactg gacagaggcc ctggagaatg tgttcatgga aaaccgcaga    720
caagacccca cactgctgtg gcaggtcttc ggcagcgcca caggagtcac tcgctactac    780
ccggccaccc cgtggcgagc ccccaagaag atcgacctgt acgatgtccg aaggagaccc    840
tggtatatcc aggggcctc gtcacccaaa gacatggtca tcatcgtgga tgtgagtggc     900
agtgtgagcg gcctgaccct gaagctgatg aagacatctg tctgcgagat gctggacacg    960
ctgtctgatg atgactatgt gaatgtggcc tcgttcaacg agaaggcaca gcctgtgtca   1020
tgcttcacac acctggtgca ggccaatgtg cgcaacaaga aggtgttcaa ggaagctgtg   1080
cagggcatgg tggccaaggg caccacaggc tacaaggccg gctttgagta tgcctttgac   1140
cagctgcaga actccaacat cactcgggcc aactgcaaca agatgatcat gatgttcacg   1200
gatggtggtg aggaccgcgt gcaggacgtc tttgagaagt acaattggcc aaaccggacg   1260
gtgcgcgtgt ttactttctc cgtggggcag cataactatg acgtcacacc gctgcagtgg   1320
atggcctgtg ccaacaaagg ctactatttt gagatccctt ccatcggagc catccgcatc   1380
aacacacagg aatatctaga tgtgttgggc aggcccatgg tgctggcagg caaggaggcc   1440
aagcaggttc agtggaccaa cgtgtatgag gatgcactgg gactggggtt ggtggtaaca   1500
gggaccctcc ctgttttcaa cctgacacag gatggccctg ggaaaaagaa gaaccagctg   1560
atcctgggcg tgatgggcat tgacgtggct ctgaatgaca tcaagaggct gacccccaac   1620
tacacgcttg gagccaacgg ctatgtgttt gccattgacc tgaacggcta cgtgttgctg   1680
caccccaatc tcaagcccca gaccaccaac ttccgggagc ctgtgactct ggacttcctg   1740
gatgcggagc tagaggatga gaacaaggaa gagatccgtc ggagcatgat tgatggcaac   1800
aagggccaca agcagatcag aacgttggtc aagtccctgg atgagaggta catagatgag   1860
gtgacacgga actacacctg ggtgcctata aggagcacta actacagcct ggggctggtg   1920
ctcccaccct acagcacctt ctacctccaa gccaatctca gtgaccagat cctgcaggtc   1980
aagtattttg agttcctgct ccccagcagc tttgagtctg aaggacacgt tttcattgct   2040
cccagagagt actgcaagga cctgaatgcc tcagacaaca acaccgagtt cctgaaaaac   2100
```

-continued tttattgagc tcatggagaa agtgactcca gactccaagc agtgcaacaa cttccttctg 2160
cacaacctga tcttggacac gggcatcacg cagcagctgg tagagcgtgt gtggagggac 2220
caggatctca acacgtacag cctactggcc gtgttcgctg ccacagacgg tggcatcacc 2280
cgagtcttcc ccaacaaggc agctgaggac tggacagaga accctgagcc cttcaatgcc 2340
agcttctacc gccgcagcct ggataaccac ggttatgtct tcaagccccc acaccaggat 2400
gccctgttaa ggccgctgga gctggagaat gacactgtgg gcatcctcgt cagcacagct 2460
gtggagctca gcctaggcag gcgcacactg aggccagcag tggtgggcgt caagctggac 2520
ctagaggctt gggctgagaa gttcaaggtg ctagccagca accgtaccca ccaagaccag 2580
cctcagaagt gcggccccaa cagccactgt gagatggact gcgaggttaa caatgaggac 2640
ttactctgtg tcctcattga tgatggagga ttcctggtgc tgtcaaacca gaaccatcag 2700
tgggaccagg tgggcaggtt cttcagtgag gtggatgcca acctgatgct ggcactctac 2760
aataactcct tctacacccg caaggagtcc tatgactatc aggcagcctg tgcccctcag 2820
ccccctggca acctgggtgc tgcaccccgg ggtgtctttg tgcccaccgt tgcagatttc 2880
cttaacctgg cctggtggac ctctgctgcc gcctggtccc tgttccagca gcttctctac 2940
ggcctcatct accacagctg gttccaagca gaccccgcgg aggccgaggg gagccccgag 3000
acgcgcgaga gcagctgcgt catgaaacag acccagtact acttcggctc ggtaaacgcc 3060
tcctacaacg ccatcatcga ctgcggaaac tgctccaggc tgttccacgc gcagagactg 3120
accaacacca atcttctctt tgtggtggcc gagaagccgc tgtgcagcca gtgcgaggct 3180
ggccggctgc tgcagaagga gacgcactgc ccagcggacg gcccggagca gtgtgagcta 3240
gtgcagagac cgcgataccg gagaggcccg cacatctgct tcgactacaa cgcgacagaa 3300
gatacctcag actgtggccg cggggcc 3327

<210> SEQ ID NO 4
<211> LENGTH: 1062
<212> TYPE: PRT
<213> ORGANISM: Homo sapiens

<400> SEQUENCE: 4

Met Ala Val Pro Ala Arg Thr Cys Gly Ala Ser Arg Pro Gly Pro Ala
1 5 10 15

Arg Thr Ala Arg Pro Trp Pro Gly Cys Gly Pro His Pro Gly Pro Gly
20 25 30

Thr Arg Arg Pro Thr Ser Gly Pro Pro Arg Pro Leu Trp Leu Leu Leu
35 40 45

Pro Leu Leu Pro Leu Leu Ala Ala Pro Gly Ala Ser Ala Tyr Ser Phe
50 55 60

Pro Gln Gln His Thr Met Gln His Trp Ala Arg Arg Leu Glu Gln Glu
65 70 75 80

Val Asp Gly Val Met Arg Ile Phe Gly Gly Val Gln Gln Leu Arg Glu
85 90 95

Ile Tyr Lys Asp Asn Arg Asn Leu Phe Glu Val Gln Glu Asn Glu Pro
100 105 110

Gln Lys Leu Val Glu Lys Val Ala Gly Asp Ile Glu Ser Leu Leu Asp
115 120 125

Arg Lys Val Gln Ala Leu Lys Arg Leu Ala Asp Ala Ala Glu Asn Phe
130 135 140

Gln Lys Ala His Arg Trp Gln Asp Asn Ile Lys Glu Glu Asp Ile Val
145 150 155 160

-continued

```
Tyr Tyr Asp Ala Lys Ala Asp Ala Glu Leu Asp Asp Pro Glu Ser Glu
                165                 170                 175

Asp Val Glu Arg Gly Ser Lys Ala Ser Thr Leu Arg Leu Asp Phe Ile
            180                 185                 190

Glu Asp Pro Asn Phe Lys Asn Lys Val Asn Tyr Ser Tyr Ala Ala Val
        195                 200                 205

Gln Ile Pro Thr Asp Ile Tyr Lys Gly Ser Thr Val Ile Leu Asn Glu
    210                 215                 220

Leu Asn Trp Thr Glu Ala Leu Glu Asn Val Phe Met Glu Asn Arg Arg
225                 230                 235                 240

Gln Asp Pro Thr Leu Leu Trp Gln Val Phe Gly Ser Ala Thr Gly Val
                245                 250                 255

Thr Arg Tyr Tyr Pro Ala Thr Pro Trp Arg Ala Pro Lys Lys Ile Asp
            260                 265                 270

Leu Tyr Asp Val Arg Arg Arg Pro Trp Tyr Ile Gln Gly Ala Ser Ser
        275                 280                 285

Pro Lys Asp Met Val Ile Ile Val Asp Val Ser Gly Ser Val Ser Gly
    290                 295                 300

Leu Thr Leu Lys Leu Met Lys Thr Ser Val Cys Glu Met Leu Asp Thr
305                 310                 315                 320

Leu Ser Asp Asp Asp Tyr Val Asn Val Ala Ser Phe Asn Glu Lys Ala
                325                 330                 335

Gln Pro Val Ser Cys Phe Thr His Leu Val Gln Ala Asn Val Arg Asn
            340                 345                 350

Lys Lys Val Phe Lys Glu Ala Val Gln Gly Met Val Ala Lys Gly Thr
        355                 360                 365

Thr Gly Tyr Lys Ala Gly Phe Glu Tyr Ala Phe Asp Gln Leu Gln Asn
    370                 375                 380

Ser Asn Ile Thr Arg Ala Asn Cys Asn Lys Met Ile Met Met Phe Thr
385                 390                 395                 400

Asp Gly Gly Glu Asp Arg Val Gln Asp Val Phe Glu Lys Tyr Asn Trp
                405                 410                 415

Pro Asn Arg Thr Val Arg Val Phe Thr Phe Ser Val Gly Gln His Asn
            420                 425                 430

Tyr Asp Val Thr Pro Leu Gln Trp Met Ala Cys Ala Asn Lys Gly Tyr
        435                 440                 445

Tyr Phe Glu Ile Pro Ser Ile Gly Ala Ile Arg Ile Asn Thr Gln Glu
    450                 455                 460

Tyr Leu Asp Val Leu Gly Arg Pro Met Val Leu Ala Gly Lys Glu Ala
465                 470                 475                 480

Lys Gln Val Gln Trp Thr Asn Val Tyr Glu Asp Ala Leu Gly Leu Gly
                485                 490                 495

Leu Val Val Thr Gly Thr Leu Pro Val Phe Asn Leu Thr Gln Asp Gly
            500                 505                 510

Pro Gly Glu Lys Lys Asn Gln Leu Ile Leu Gly Val Met Gly Ile Asp
        515                 520                 525

Val Ala Leu Asn Asp Ile Lys Arg Leu Thr Pro Asn Tyr Thr Leu Gly
    530                 535                 540

Ala Asn Gly Tyr Val Phe Ala Ile Asp Leu Asn Gly Tyr Val Leu Leu
545                 550                 555                 560

His Pro Asn Leu Lys Pro Gln Thr Thr Asn Phe Arg Glu Pro Val Thr
                565                 570                 575
```

-continued

```
Leu Asp Phe Leu Asp Ala Glu Leu Glu Asp Glu Asn Lys Glu Glu Ile
            580                 585                 590

Arg Arg Ser Met Ile Asp Gly Asn Lys Gly His Lys Gln Ile Arg Thr
        595                 600                 605

Leu Val Lys Ser Leu Asp Glu Arg Tyr Ile Asp Glu Val Thr Arg Asn
    610                 615                 620

Tyr Thr Trp Val Pro Ile Arg Ser Thr Asn Tyr Ser Leu Gly Leu Val
625                 630                 635                 640

Leu Pro Pro Tyr Ser Thr Phe Tyr Leu Gln Ala Asn Leu Ser Asp Gln
                645                 650                 655

Ile Leu Gln Val Lys Tyr Phe Glu Phe Leu Leu Pro Ser Ser Phe Glu
            660                 665                 670

Ser Glu Gly His Val Phe Ile Ala Pro Arg Glu Tyr Cys Lys Asp Leu
        675                 680                 685

Asn Ala Ser Asp Asn Asn Thr Glu Phe Leu Lys Asn Phe Ile Glu Leu
    690                 695                 700

Met Glu Lys Val Thr Pro Asp Ser Lys Gln Cys Asn Asn Phe Leu Leu
705                 710                 715                 720

His Asn Leu Ile Leu Asp Thr Gly Ile Thr Gln Gln Leu Val Glu Arg
                725                 730                 735

Val Trp Arg Asp Gln Asp Leu Asn Thr Tyr Ser Leu Leu Ala Val Phe
            740                 745                 750

Ala Ala Thr Asp Gly Gly Ile Thr Arg Val Phe Pro Asn Lys Ala Ala
        755                 760                 765

Glu Asp Trp Thr Glu Asn Pro Glu Pro Phe Asn Ala Ser Phe Tyr Arg
    770                 775                 780

Arg Ser Leu Asp Asn His Gly Tyr Val Phe Lys Pro Pro His Gln Asp
785                 790                 795                 800

Ala Leu Leu Arg Pro Leu Glu Leu Glu Asn Asp Thr Val Gly Ile Leu
                805                 810                 815

Val Ser Thr Ala Val Glu Leu Ser Leu Gly Arg Arg Thr Leu Arg Pro
            820                 825                 830

Ala Val Val Gly Val Lys Leu Asp Leu Glu Ala Trp Ala Glu Lys Phe
        835                 840                 845

Lys Val Leu Ala Ser Asn Arg Thr His Gln Asp Gln Pro Gln Lys Cys
    850                 855                 860

Gly Pro Asn Ser His Cys Glu Met Asp Cys Glu Val Asn Asn Glu Asp
865                 870                 875                 880

Leu Leu Cys Val Leu Ile Asp Asp Gly Gly Phe Leu Val Leu Ser Asn
                885                 890                 895

Gln Asn His Gln Trp Asp Gln Val Gly Arg Phe Phe Ser Glu Val Asp
            900                 905                 910

Ala Asn Leu Met Leu Ala Leu Tyr Asn Asn Ser Phe Tyr Thr Arg Lys
        915                 920                 925

Glu Ser Tyr Asp Tyr Gln Ala Ala Cys Ala Pro Gln Pro Pro Gly Asn
    930                 935                 940

Leu Gly Ala Ala Pro Arg Gly Val Phe Val Pro Thr Val Ala Asp Phe
945                 950                 955                 960

Leu Asn Leu Ala Trp Trp Thr Ser Ala Ala Ala Trp Ser Leu Phe Gln
                965                 970                 975

Gln Leu Leu Tyr Gly Leu Ile Tyr His Ser Trp Phe Gln Ala Asp Pro
            980                 985                 990

Ala Glu Ala Glu Gly Ser Pro Glu Thr Arg Glu Ser Ser Cys Val Met
```

-continued

```
        995                 1000                1005

Lys Gln Thr Gln Tyr Tyr Phe Gly Ser Val Asn Ala Ser Tyr Asn Ala
   1010                1015                1020

Ile Ile Asp Cys Gly Asn Cys Ser Arg Leu Phe His Ala Gln Arg Leu
1025                1030                1035                1040

Thr Asn Thr Asn Leu Leu Phe Val Val Ala Glu Lys Pro Leu Cys Ser
               1045                1050                1055

Gln Cys Glu Ala Gly Arg
           1060


<210> SEQ ID NO 5
<211> LENGTH: 1082
<212> TYPE: PRT
<213> ORGANISM: Homo sapiens

<400> SEQUENCE: 5

Met Ala Val Pro Ala Arg Thr Cys Gly Ala Ser Arg Pro Gly Pro Ala
  1               5                  10                  15

Arg Thr Ala Arg Pro Trp Pro Gly Cys Gly Pro His Pro Gly Pro Gly
             20                  25                  30

Thr Arg Arg Pro Thr Ser Gly Pro Pro Arg Pro Leu Trp Leu Leu Leu
         35                  40                  45

Pro Leu Leu Pro Leu Leu Ala Ala Pro Gly Ala Ser Ala Tyr Ser Phe
     50                  55                  60

Pro Gln Gln His Thr Met Gln His Trp Ala Arg Arg Leu Glu Gln Glu
 65                  70                  75                  80

Val Asp Gly Val Met Arg Ile Phe Gly Gly Val Gln Gln Leu Arg Glu
                 85                  90                  95

Ile Tyr Lys Asp Asn Arg Asn Leu Phe Glu Val Gln Glu Asn Glu Pro
            100                 105                 110

Gln Lys Leu Val Glu Lys Val Ala Gly Asp Ile Glu Ser Leu Leu Asp
        115                 120                 125

Arg Lys Val Gln Ala Leu Lys Arg Leu Ala Asp Ala Ala Glu Asn Phe
    130                 135                 140

Gln Lys Ala His Arg Trp Gln Asp Asn Ile Lys Glu Glu Asp Ile Val
145                 150                 155                 160

Tyr Tyr Asp Ala Lys Ala Asp Ala Glu Leu Asp Asp Pro Glu Ser Glu
                165                 170                 175

Asp Val Glu Arg Gly Ser Lys Ala Ser Thr Leu Arg Leu Asp Phe Ile
            180                 185                 190

Glu Asp Pro Asn Phe Lys Asn Lys Val Asn Tyr Ser Tyr Ala Ala Val
        195                 200                 205

Gln Ile Pro Thr Asp Ile Tyr Lys Gly Ser Thr Val Ile Leu Asn Glu
    210                 215                 220

Leu Asn Trp Thr Glu Ala Leu Glu Asn Val Phe Met Glu Asn Arg Arg
225                 230                 235                 240

Gln Asp Pro Thr Leu Leu Trp Gln Val Phe Gly Ser Ala Thr Gly Val
                245                 250                 255

Thr Arg Tyr Tyr Pro Ala Thr Pro Trp Arg Ala Pro Lys Lys Ile Asp
            260                 265                 270

Leu Tyr Asp Val Arg Arg Arg Pro Trp Tyr Ile Gln Gly Ala Ser Ser
        275                 280                 285

Pro Lys Asp Met Val Ile Ile Val Asp Val Ser Gly Ser Val Ser Gly
    290                 295                 300
```

-continued

```
Leu Thr Leu Lys Leu Met Lys Thr Ser Val Cys Glu Met Leu Asp Thr
305                 310                 315                 320

Leu Ser Asp Asp Asp Tyr Val Asn Val Ala Ser Phe Asn Glu Lys Ala
                325                 330                 335

Gln Pro Val Ser Cys Phe Thr His Leu Val Gln Ala Asn Val Arg Asn
            340                 345                 350

Lys Lys Val Phe Lys Glu Ala Val Gln Gly Met Val Ala Lys Gly Thr
        355                 360                 365

Thr Gly Tyr Lys Ala Gly Phe Glu Tyr Ala Phe Asp Gln Leu Gln Asn
    370                 375                 380

Ser Asn Ile Thr Arg Ala Asn Cys Asn Lys Met Ile Met Met Phe Thr
385                 390                 395                 400

Asp Gly Gly Glu Asp Arg Val Gln Asp Val Phe Glu Lys Tyr Asn Trp
                405                 410                 415

Pro Asn Arg Thr Val Arg Val Phe Thr Phe Ser Val Gly Gln His Asn
            420                 425                 430

Tyr Asp Val Thr Pro Leu Gln Trp Met Ala Cys Ala Asn Lys Gly Tyr
        435                 440                 445

Tyr Phe Glu Ile Pro Ser Ile Gly Ala Ile Arg Ile Asn Thr Gln Glu
    450                 455                 460

Tyr Leu Asp Val Leu Gly Arg Pro Met Val Leu Ala Gly Lys Glu Ala
465                 470                 475                 480

Lys Gln Val Gln Trp Thr Asn Val Tyr Glu Asp Ala Leu Gly Leu Gly
                485                 490                 495

Leu Val Val Thr Gly Thr Leu Pro Val Phe Asn Leu Thr Gln Asp Gly
            500                 505                 510

Pro Gly Glu Lys Lys Asn Gln Leu Ile Leu Gly Val Met Gly Ile Asp
        515                 520                 525

Val Ala Leu Asn Asp Ile Lys Arg Leu Thr Pro Asn Tyr Thr Leu Gly
    530                 535                 540

Ala Asn Gly Tyr Val Phe Ala Ile Asp Leu Asn Gly Tyr Val Leu Leu
545                 550                 555                 560

His Pro Asn Leu Lys Pro Gln Thr Thr Asn Phe Arg Glu Pro Val Thr
                565                 570                 575

Leu Asp Phe Leu Asp Ala Glu Leu Glu Asp Glu Asn Lys Glu Glu Ile
            580                 585                 590

Arg Arg Ser Met Ile Asp Gly Asn Lys Gly His Lys Gln Ile Arg Thr
        595                 600                 605

Leu Val Lys Ser Leu Asp Glu Arg Tyr Ile Asp Glu Val Thr Arg Asn
    610                 615                 620

Tyr Thr Trp Val Pro Ile Arg Ser Thr Asn Tyr Ser Leu Gly Leu Val
625                 630                 635                 640

Leu Pro Pro Tyr Ser Thr Phe Tyr Leu Gln Ala Asn Leu Ser Asp Gln
                645                 650                 655

Ile Leu Gln Val Lys Tyr Phe Glu Phe Leu Leu Pro Ser Ser Phe Glu
            660                 665                 670

Ser Glu Gly His Val Phe Ile Ala Pro Arg Glu Tyr Cys Lys Asp Leu
        675                 680                 685

Asn Ala Ser Asp Asn Asn Thr Glu Phe Leu Lys Asn Phe Ile Glu Leu
    690                 695                 700

Met Glu Lys Val Thr Pro Asp Ser Lys Gln Cys Asn Asn Phe Leu Leu
705                 710                 715                 720

His Asn Leu Ile Leu Asp Thr Gly Ile Thr Gln Gln Leu Val Glu Arg
```

-continued

```
                725                 730                 735

Val Trp Arg Asp Gln Asp Leu Asn Thr Tyr Ser Leu Leu Ala Val Phe
            740                 745                 750

Ala Ala Thr Asp Gly Gly Ile Thr Arg Val Phe Pro Asn Lys Ala Ala
        755                 760                 765

Glu Asp Trp Thr Glu Asn Pro Glu Pro Phe Asn Ala Ser Phe Tyr Arg
    770                 775                 780

Arg Ser Leu Asp Asn His Gly Tyr Val Phe Lys Pro Pro His Gln Asp
785                 790                 795                 800

Ala Leu Leu Arg Pro Leu Glu Leu Glu Asn Asp Thr Val Gly Ile Leu
                805                 810                 815

Val Ser Thr Ala Val Glu Leu Ser Leu Gly Arg Arg Thr Leu Arg Pro
            820                 825                 830

Ala Val Val Gly Val Lys Leu Asp Leu Glu Ala Trp Ala Glu Lys Phe
        835                 840                 845

Lys Val Leu Ala Ser Asn Arg Thr His Gln Asp Gln Pro Gln Lys Cys
    850                 855                 860

Gly Pro Asn Ser His Cys Glu Met Asp Cys Glu Val Asn Asn Glu Asp
865                 870                 875                 880

Leu Leu Cys Val Leu Ile Asp Asp Gly Gly Phe Leu Val Leu Ser Asn
                885                 890                 895

Gln Asn His Gln Trp Asp Gln Val Gly Arg Phe Phe Ser Glu Val Asp
            900                 905                 910

Ala Asn Leu Met Leu Ala Leu Tyr Asn Asn Ser Phe Tyr Thr Arg Lys
        915                 920                 925

Glu Ser Tyr Asp Tyr Gln Ala Ala Cys Ala Pro Gln Pro Pro Gly Asn
    930                 935                 940

Leu Gly Ala Ala Pro Arg Gly Val Phe Val Pro Thr Val Ala Asp Phe
945                 950                 955                 960

Leu Asn Leu Ala Trp Trp Thr Ser Ala Ala Ala Trp Ser Leu Phe Gln
                965                 970                 975

Gln Leu Leu Tyr Gly Leu Ile Tyr His Ser Trp Phe Gln Ala Asp Pro
            980                 985                 990

Ala Glu Ala Glu Gly Ser Pro Glu Thr Arg Glu Ser Ser Cys Val Met
        995                 1000                1005

Lys Gln Thr Gln Tyr Tyr Phe Gly Ser Val Asn Ala Ser Tyr Asn Ala
   1010                1015                1020

Ile Ile Asp Cys Gly Asn Cys Ser Arg Leu Phe His Ala Gln Arg Leu
1025                1030                1035                1040

Thr Asn Thr Asn Leu Leu Phe Val Val Ala Glu Lys Pro Leu Cys Ser
               1045                1050                1055

Gln Cys Glu Ala Gly Arg Leu Leu Gln Lys Glu Thr His Cys Pro Ala
           1060                1065                1070

Asp Gly Pro Glu Gln Cys Glu Leu Val Gln
       1075                1080


<210> SEQ ID NO 6
<211> LENGTH: 1109
<212> TYPE: PRT
<213> ORGANISM: Homo sapiens

<400> SEQUENCE: 6

Met Ala Val Pro Ala Arg Thr Cys Gly Ala Ser Arg Pro Gly Pro Ala
  1               5                  10                  15
```

-continued

```
Arg Thr Ala Arg Pro Trp Pro Gly Cys Gly Pro His Pro Gly Pro Gly
            20                  25                  30

Thr Arg Arg Pro Thr Ser Gly Pro Pro Arg Pro Leu Trp Leu Leu Leu
        35                  40                  45

Pro Leu Leu Pro Leu Leu Ala Ala Pro Gly Ala Ser Ala Tyr Ser Phe
    50                  55                  60

Pro Gln Gln His Thr Met Gln His Trp Ala Arg Arg Leu Glu Gln Glu
65                  70                  75                  80

Val Asp Gly Val Met Arg Ile Phe Gly Gly Val Gln Gln Leu Arg Glu
                85                  90                  95

Ile Tyr Lys Asp Asn Arg Asn Leu Phe Glu Val Gln Glu Asn Glu Pro
            100                 105                 110

Gln Lys Leu Val Glu Lys Val Ala Gly Asp Ile Glu Ser Leu Leu Asp
        115                 120                 125

Arg Lys Val Gln Ala Leu Lys Arg Leu Ala Asp Ala Ala Glu Asn Phe
    130                 135                 140

Gln Lys Ala His Arg Trp Gln Asp Asn Ile Lys Glu Glu Asp Ile Val
145                 150                 155                 160

Tyr Tyr Asp Ala Lys Ala Asp Ala Glu Leu Asp Asp Pro Glu Ser Glu
                165                 170                 175

Asp Val Glu Arg Gly Ser Lys Ala Ser Thr Leu Arg Leu Asp Phe Ile
            180                 185                 190

Glu Asp Pro Asn Phe Lys Asn Lys Val Asn Tyr Ser Tyr Ala Ala Val
        195                 200                 205

Gln Ile Pro Thr Asp Ile Tyr Lys Gly Ser Thr Val Ile Leu Asn Glu
    210                 215                 220

Leu Asn Trp Thr Glu Ala Leu Glu Asn Val Phe Met Glu Asn Arg Arg
225                 230                 235                 240

Gln Asp Pro Thr Leu Leu Trp Gln Val Phe Gly Ser Ala Thr Gly Val
                245                 250                 255

Thr Arg Tyr Tyr Pro Ala Thr Pro Trp Arg Ala Pro Lys Lys Ile Asp
            260                 265                 270

Leu Tyr Asp Val Arg Arg Arg Pro Trp Tyr Ile Gln Gly Ala Ser Ser
        275                 280                 285

Pro Lys Asp Met Val Ile Ile Val Asp Val Ser Gly Ser Val Ser Gly
    290                 295                 300

Leu Thr Leu Lys Leu Met Lys Thr Ser Val Cys Glu Met Leu Asp Thr
305                 310                 315                 320

Leu Ser Asp Asp Asp Tyr Val Asn Val Ala Ser Phe Asn Glu Lys Ala
                325                 330                 335

Gln Pro Val Ser Cys Phe Thr His Leu Val Gln Ala Asn Val Arg Asn
            340                 345                 350

Lys Lys Val Phe Lys Glu Ala Val Gln Gly Met Val Ala Lys Gly Thr
        355                 360                 365

Thr Gly Tyr Lys Ala Gly Phe Glu Tyr Ala Phe Asp Gln Leu Gln Asn
    370                 375                 380

Ser Asn Ile Thr Arg Ala Asn Cys Asn Lys Met Ile Met Met Phe Thr
385                 390                 395                 400

Asp Gly Gly Glu Asp Arg Val Gln Asp Val Phe Glu Lys Tyr Asn Trp
                405                 410                 415

Pro Asn Arg Thr Val Arg Val Phe Thr Phe Ser Val Gly Gln His Asn
            420                 425                 430

Tyr Asp Val Thr Pro Leu Gln Trp Met Ala Cys Ala Asn Lys Gly Tyr
```

-continued

```
        435                 440                 445

Tyr Phe Glu Ile Pro Ser Ile Gly Ala Ile Arg Ile Asn Thr Gln Glu
    450                 455                 460

Tyr Leu Asp Val Leu Gly Arg Pro Met Val Leu Ala Gly Lys Glu Ala
465                 470                 475                 480

Lys Gln Val Gln Trp Thr Asn Val Tyr Glu Asp Ala Leu Gly Leu Gly
                485                 490                 495

Leu Val Val Thr Gly Thr Leu Pro Val Phe Asn Leu Thr Gln Asp Gly
            500                 505                 510

Pro Gly Glu Lys Lys Asn Gln Leu Ile Leu Gly Val Met Gly Ile Asp
        515                 520                 525

Val Ala Leu Asn Asp Ile Lys Arg Leu Thr Pro Asn Tyr Thr Leu Gly
    530                 535                 540

Ala Asn Gly Tyr Val Phe Ala Ile Asp Leu Asn Gly Tyr Val Leu Leu
545                 550                 555                 560

His Pro Asn Leu Lys Pro Gln Thr Thr Asn Phe Arg Glu Pro Val Thr
                565                 570                 575

Leu Asp Phe Leu Asp Ala Glu Leu Glu Asp Glu Asn Lys Glu Glu Ile
            580                 585                 590

Arg Arg Ser Met Ile Asp Gly Asn Lys Gly His Lys Gln Ile Arg Thr
        595                 600                 605

Leu Val Lys Ser Leu Asp Glu Arg Tyr Ile Asp Glu Val Thr Arg Asn
    610                 615                 620

Tyr Thr Trp Val Pro Ile Arg Ser Thr Asn Tyr Ser Leu Gly Leu Val
625                 630                 635                 640

Leu Pro Pro Tyr Ser Thr Phe Tyr Leu Gln Ala Asn Leu Ser Asp Gln
                645                 650                 655

Ile Leu Gln Val Lys Tyr Phe Glu Phe Leu Leu Pro Ser Ser Phe Glu
            660                 665                 670

Ser Glu Gly His Val Phe Ile Ala Pro Arg Glu Tyr Cys Lys Asp Leu
        675                 680                 685

Asn Ala Ser Asp Asn Asn Thr Glu Phe Leu Lys Asn Phe Ile Glu Leu
    690                 695                 700

Met Glu Lys Val Thr Pro Asp Ser Lys Gln Cys Asn Asn Phe Leu Leu
705                 710                 715                 720

His Asn Leu Ile Leu Asp Thr Gly Ile Thr Gln Gln Leu Val Glu Arg
                725                 730                 735

Val Trp Arg Asp Gln Asp Leu Asn Thr Tyr Ser Leu Leu Ala Val Phe
            740                 745                 750

Ala Ala Thr Asp Gly Gly Ile Thr Arg Val Phe Pro Asn Lys Ala Ala
        755                 760                 765

Glu Asp Trp Thr Glu Asn Pro Glu Pro Phe Asn Ala Ser Phe Tyr Arg
    770                 775                 780

Arg Ser Leu Asp Asn His Gly Tyr Val Phe Lys Pro Pro His Gln Asp
785                 790                 795                 800

Ala Leu Leu Arg Pro Leu Glu Leu Glu Asn Asp Thr Val Gly Ile Leu
                805                 810                 815

Val Ser Thr Ala Val Glu Leu Ser Leu Gly Arg Arg Thr Leu Arg Pro
            820                 825                 830

Ala Val Val Gly Val Lys Leu Asp Leu Glu Ala Trp Ala Glu Lys Phe
        835                 840                 845

Lys Val Leu Ala Ser Asn Arg Thr His Gln Asp Gln Pro Gln Lys Cys
    850                 855                 860
```

```
Gly Pro Asn Ser His Cys Glu Met Asp Cys Glu Val Asn Asn Glu Asp
865                 870                 875                 880

Leu Leu Cys Val Leu Ile Asp Asp Gly Gly Phe Leu Val Leu Ser Asn
                885                 890                 895

Gln Asn His Gln Trp Asp Gln Val Gly Arg Phe Phe Ser Glu Val Asp
            900                 905                 910

Ala Asn Leu Met Leu Ala Leu Tyr Asn Asn Ser Phe Tyr Thr Arg Lys
        915                 920                 925

Glu Ser Tyr Asp Tyr Gln Ala Ala Cys Ala Pro Gln Pro Pro Gly Asn
    930                 935                 940

Leu Gly Ala Ala Pro Arg Gly Val Phe Val Pro Thr Val Ala Asp Phe
945                 950                 955                 960

Leu Asn Leu Ala Trp Trp Thr Ser Ala Ala Ala Trp Ser Leu Phe Gln
                965                 970                 975

Gln Leu Leu Tyr Gly Leu Ile Tyr His Ser Trp Phe Gln Ala Asp Pro
            980                 985                 990

Ala Glu Ala Glu Gly Ser Pro Glu Thr Arg Glu Ser Ser Cys Val Met
        995                 1000                1005

Lys Gln Thr Gln Tyr Tyr Phe Gly Ser Val Asn Ala Ser Tyr Asn Ala
   1010                1015                1020

Ile Ile Asp Cys Gly Asn Cys Ser Arg Leu Phe His Ala Gln Arg Leu
1025               1030                1035                1040

Thr Asn Thr Asn Leu Leu Phe Val Val Ala Glu Lys Pro Leu Cys Ser
               1045                1050                1055

Gln Cys Glu Ala Gly Arg Leu Leu Gln Lys Glu Thr His Cys Pro Ala
           1060                1065                1070

Asp Gly Pro Glu Gln Cys Glu Leu Val Gln Arg Pro Arg Tyr Arg Arg
       1075                1080                1085

Gly Pro His Ile Cys Phe Asp Tyr Asn Ala Thr Glu Asp Thr Ser Asp
   1090                1095                1100

Cys Gly Arg Gly Ala
1105
```

<210> SEQ ID NO 7
<211> LENGTH: 3057
<212> TYPE: DNA
<213> ORGANISM: Homo sapiens

<400> SEQUENCE: 7

```
atggccgggc cgggctcgcc gcgccgcgcg tcccgggggg cctcggcgct tctcgctgcc     60

gcgcttctct acgccgcgct gggggacgtg gtgcgctcgg agcagcagat accgctctcc    120

gtggtgaagc tctgggcctc ggcttttggt ggggagataa aatccattgc tgctaagtac    180

tccggttccc agcttctgca aaagaaatac aaagagtatg agaaagacgt tgccatagaa    240

gaaattgatg gcctccaact ggtaaagaag ctggcaaaga acatggaaga gatgtttcac    300

aagaagtctg aggccgtcag gcgtctggtg gaggctgcag aagaagcaca cctgaaacat    360

gaatttgatg cagacttaca gtatgaatac ttcaatgctg tgctgataaa tgaaagggac    420

aaagacggga attttttgga gctgggaaag gaattcatct tagccccaaa tgaccatttt    480

aataatttgc ctgtgaacat cagtctaagt gacgtccaag taccaacgaa catgtacaac    540

aaagaccctg caattgtcaa tggggtttat tggtctgaat ctctaaacaa agtttttgta    600

gataactttg accgtgaccc atctctcata tggcagtact ttggaagtgc aaagggcttt    660
```

-continued

```
tttaggcagt atccggggat taaatgggaa ccagatgaga atggagtcat tgccttcgac    720
tgcaggaacc gaaaatggta catccaggca gcaacttctc cgaaagacgt ggtcatttta    780
gttgacgtca gtggcagcat gaaaggactc cgtctgacta tcgcgaagca aacagtctca    840
tccattttgg atacacttgg ggatgatgac ttcttcaaca taattgctta taatgaggag    900
cttcactatg tggaaccttg cctgaatgga actttggtgc aagccgacag gacaaacaaa    960
gagcacttca gggagcatct ggacaaactt ttcgccaaag gaattggaat gttggatata   1020
gctctgaatg aggccttcaa cattctgagt gatttcaacc acacgggaca aggaagtatc   1080
tgcagtcagg ccatcatgct cataactgat ggggcggtgg acacctatga tacaatcttt   1140
gcaaaataca attggccaga tcgaaaggtt cgcatcttca catacctcat tggacgagag   1200
gctgcgtttg cagacaatct aaagtggatg gcctgtgcca acaaaggatt ttttacccag   1260
atctccacct tggctgatgt gcaggagaat gtcatggaat accttcacgt gcttagccgg   1320
cccaaagtca tcgaccagga gcatgatgtg gtgtggaccg aagcttacat tgacagcact   1380
ctgactgatg atcagggccc cgtcctgatg accactgtag ccatgcctgt gtttagtaag   1440
cagaacgaaa ccagatcgaa gggcattctt ctgggagtgg ttggcacaga tgtcccagtg   1500
aaagaacttc tgaagaccat ccccaaatac aagttaggga ttcacggtta tgcctttgca   1560
atcacaaata atggrtatat cctgacgcat ccggaactca ggctgctgta cgaagaagga   1620
aaaaagcgaa ggaaacctaa ctatagtagc gttgacctct ctgaggtgga gtgggaagac   1680
cgagatgacg tgttgagaaa tgctatggtg aatcgaaaga cggggaagtt ttccatggag   1740
gtgaagaaga cagtggacaa agggaaacgg gttttggtga tgacaaatga ctactattat   1800
acagacatca agggtactcc tttcagttta ggtgtggcgc tttccagagg tcatgggaaa   1860
tatttcttcc gagggaatgt aaccatcgaa gaaggcctgc atgacttaga acatcccgat   1920
gtgtccttgg cagatgaatg gtcctactgc aacactgacc tacaccctga gcaccgccat   1980
ctgtctcagt tagaagcgat taagctctac ctaaaaggca aagaacctct gctccagtgt   2040
gataaagaat tgatccaaga agtccttttt gacgcggtgg tgagtgcccc cattgaagcg   2100
tattggacca gcctggccct caacaaatct gaaaattctg acaagggcgt ggaggttgcc   2160
ttcctcggca ctcgcacggg cctctccaga atcaacctgt ttgtcggggc tgagcagctc   2220
accaatcagg acttcctgaa agctggcgac aaggagaaca tttttaacgc agaccatttc   2280
cctctctggt accgaagagc cgctgagcag attccaggga gcttcgtcta ctcgatccca   2340
ttcagcactg gaccagtcaa taaaagcaat gtggtgacag caagtacatc catccagctc   2400
ctggatgaac ggaaatctcc tgtggtggca gctgtaggca ttcagatgaa acttgaattt   2460
ttccaaagga agttctggac tgccagcaga cagtgtgctt ccctggatgg caaatgctcc   2520
atcagctgtg atgatgagac tgtgaattgt tacctcatag acaataatgg atttattttg   2580
gtgtctgaag actacacaca gactggagac ttttttggtg agatcgaggg agctgtgatg   2640
aacaaattgc taacaatggg ctcctttaaa agaattaccc tttatgacta ccaagccatg   2700
tgtagagcca acaaggaaag cagcgatggc gcccatggcc tcctggatcc ttataatgcc   2760
ttcctctctg cagtaaaatg gatcatgaca gaacttgtct tgttcctggt ggaatttaac   2820
ctctgcagtt ggtggcactc cgatatgaca gctaaagccc agaaattgaa acagaccctg   2880
gagccttgtg atactgaata tccagcattc gtctctgagc gcaccatcaa ggagactaca   2940
gggaatattg cttgtgaaga ctgctccaag tcctttgtca tccagcaaat cccaagcagc   3000
aacctgttca tggtggtggt ggacagcagc tgcctctgtg aatctgtggc ccccatc      3057
```

-continued

<210> SEQ ID NO 8
<211> LENGTH: 3114
<212> TYPE: DNA
<213> ORGANISM: Homo sapiens

<400> SEQUENCE: 8

```
atggccgggc cgggctcgcc gcgccgcgcg tcccgggggg cctcggcgct tctcgctgcc      60
gcgcttctct acgccgcgct gggggacgtg gtgcgctcgg agcagcagat accgctctcc     120
gtggtgaagc tctgggcctc ggcttttggt ggggagataa aatccattgc tgctaagtac     180
tccggttccc agcttctgca aaagaaatac aaagagtatg agaaagacgt tgccatagaa     240
gaaattgatg gcctccaact ggtaaagaag ctggcaaaga acatggaaga gatgtttcac     300
aagaagtctg aggccgtcag gcgtctggtg gaggctgcag aagaagcaca cctgaaacat     360
gaatttgatg cagacttaca gtatgaatac ttcaatgctg tgctgataaa tgaaagggac     420
aaagacggga attttttgga gctgggaaag gaattcatct tagccccaaa tgaccatttt     480
aataatttgc ctgtgaacat cagtctaagt gacgtccaag taccaacgaa catgtacaac     540
aaagaccctg caattgtcaa tggggtttat tggtctgaat ctctaaacaa agtttttgta     600
gataactttg accgtgaccc atctctcata tggcagtact ttggaagtgc aaagggcttt     660
tttaggcagt atccggggat taaatgggaa ccagatgaga atggagtcat tgccttcgac     720
tgcaggaacc gaaaatggta catccaggca gcaacttctc cgaaagacgt ggtcatttta     780
gttgacgtca gtggcagcat gaaaggactc cgtctgacta tcgcgaagca aacagtctca     840
tccattttgg atacacttgg ggatgatgac ttcttcaaca taattgctta taatgaggag     900
cttcactatg tggaaccttg cctgaatgga actttggtgc aagccgacag gacaaacaaa     960
gagcacttca gggagcatct ggacaaactt ttcgccaaag gaattggaat gttggatata    1020
gctctgaatg aggccttcaa cattctgagt gatttcaacc acacgggaca aggaagtatc    1080
tgcagtcagg ccatcatgct cataactgat ggggcggtgg acacctatga tacaatcttt    1140
gcaaaataca attggccaga tcgaaaggtt cgcatcttca catacctcat tggacgagag    1200
gctgcgtttg cagacaatct aaagtggatg gcctgtgcca acaaaggatt ttttacccag    1260
atctccacct tggctgatgt gcaggagaat gtcatggaat accttcacgt gcttagccgg    1320
cccaaagtca tcgaccagga gcatgatgtg gtgtggaccg aagcttacat tgacagcact    1380
ctgactgatg atcagggccc cgtcctgatg accactgtag ccatgcctgt gtttagtaag    1440
cagaacgaaa ccagatcgaa gggcattctt ctgggagtgg ttggcacaga tgtcccagtg    1500
aaagaacttc tgaagaccat ccccaaatac aagttaggga ttcacggtta tgcctttgca    1560
atcacaaata atggrtatat cctgacgcat ccggaactca ggctgctgta cgaagaagga    1620
aaaaagcgaa ggaaacctaa ctatagtagc gttgacctct ctgaggtgga gtgggaagac    1680
cgagatgacg tgttgagaaa tgctatggtg aatcgaaaga cggggaagtt ttccatggag    1740
gtgaagaaga cagtggacaa agggaaacgg gttttggtga tgacaaatga ctactattat    1800
acagacatca agggtactcc tttcagttta ggtgtggcgc tttccagagg tcatgggaaa    1860
tatttcttcc gagggaatgt aaccatcgaa gaaggcctgc atgacttaga acatcccgat    1920
gtgtccttgg cagatgaatg gtcctactgc aacactgacc tacaccctga gcaccgccat    1980
ctgtctcagt tagaagcgat taagctctac ctaaaaggca aagaacctct gctccagtgt    2040
gataaagaat tgatccaaga agtccttttt gacgcggtgg tgagtgcccc cattgaagcg    2100
```

-continued

```
tattggacca gcctggccct caacaaatct gaaaattctg acaagggcgt ggaggttgcc   2160
ttcctcggca ctcgcacggg cctctccaga atcaacctgt ttgtcggggc tgagcagctc   2220
accaatcagg acttcctgaa agctggcgac aaggagaaca tttttaacgc agaccatttc   2280
cctctctggt accgaagagc cgctgagcag attccaggga gcttcgtcta ctcgatccca   2340
ttcagcactg gaccagtcaa taaaagcaat gtggtgacag caagtacatc catccagctc   2400
ctggatgaac ggaaatctcc tgtggtggca gctgtaggca ttcagatgaa acttgaattt   2460
ttccaaagga agttctggac tgccagcaga cagtgtgctt ccctggatgg caaatgctcc   2520
atcagctgtg atgatgagac tgtgaattgt tacctcatag acaataatgg atttattttg   2580
gtgtctgaag actacacaca gactggagac tttttttggtg agatcgaggg agctgtgatg   2640
aacaaattgc taacaatggg ctcctttaaa agaattaccc tttatgacta ccaagccatg   2700
tgtagagcca acaaggaaag cagcgatggc gcccatggcc tcctggatcc ttataatgcc   2760
ttcctctctg cagtaaaatg gatcatgaca gaacttgtct tgttcctggt ggaatttaac   2820
ctctgcagtt ggtggcactc cgatatgaca gctaaagccc agaaattgaa acagaccctg   2880
gagccttgtg atactgaata tccagcattc gtctctgagc gcaccatcaa ggagactaca   2940
gggaatattg cttgtgaaga ctgctccaag tcctttgtca tccagcaaat cccaagcagc   3000
aacctgttca tggtggtggt ggacagcagc tgcctctgtg aatctgtggc cccatcacc    3060
atggcaccca ttgaaatcag gtataatgaa tcccttaagt gtgaacgtct aaag         3114
```

<210> SEQ ID NO 9
<211> LENGTH: 3213
<212> TYPE: DNA
<213> ORGANISM: Homo sapiens

<400> SEQUENCE: 9

```
atggccgggc cgggctcgcc gcgccgcgcg tcccgggggg cctcggcgct tctcgctgcc     60
gcgcttctct acgccgcgct gggggacgtg gtgcgctcgg agcagcagat accgctctcc    120
gtggtgaagc tctgggcctc ggcttttggt ggggagataa aatccattgc tgctaagtac    180
tccggttccc agcttctgca aaagaaatac aaagagtatg agaaagacgt tgccatagaa    240
gaaattgatg gcctccaact ggtaaagaag ctggcaaaga acatggaaga gatgtttcac    300
aagaagtctg aggccgtcag gcgtctggtg gaggctgcag aagaagcaca cctgaaacat    360
gaatttgatg cagacttaca gtatgaatac ttcaatgctg tgctgataaa tgaaagggac    420
aaagacggga attttttgga gctgggaaag gaattcatct tagccccaaa tgaccatttt    480
aataatttgc ctgtgaacat cagtctaagt gacgtccaag taccaacgaa catgtacaac    540
aaagaccctg caattgtcaa tggggtttat tggtctgaat ctctaaacaa agtttttgta    600
gataactttg accgtgaccc atctctcata tggcagtact ttggaagtgc aaagggcttt    660
tttaggcagt atccggggat taaatgggaa ccagatgaga atggagtcat tgccttcgac    720
tgcaggaacc gaaaatggta catccaggca gcaacttctc cgaaagacgt ggtcatttta    780
gttgacgtca gtggcagcat gaaaggactc cgtctgacta tcgcgaagca aacagtctca    840
tccattttgg atacacttgg ggatgatgac ttcttcaaca taattgctta taatgaggag    900
cttcactatg tggaaccttg cctgaatgga actttggtgc aagccgacag gacaaacaaa    960
gagcacttca gggagcatct ggacaaactt ttcgccaaag gaattggaat gttggatata   1020
gctctgaatg aggccttcaa cattctgagt gatttcaacc acacgggaca aggaagtatc   1080
tgcagtcagg ccatcatgct cataactgat ggggcggtgg acacctatga tacaatcttt   1140
```

-continued

```
gcaaaataca attggccaga tcgaaaggtt cgcatcttca catacctcat tggacgagag   1200

gctgcgtttg cagacaatct aaagtggatg gcctgtgcca acaaaggatt ttttacccag   1260

atctccacct tggctgatgt gcaggagaat gtcatggaat accttcacgt gcttagccgg   1320

cccaaagtca tcgaccagga gcatgatgtg gtgtggaccg aagcttacat tgacagcact   1380

ctgactgatg atcagggccc cgtcctgatg accactgtag ccatgcctgt gtttagtaag   1440

cagaacgaaa ccagatcgaa gggcattctt ctgggagtgg ttggcacaga tgtcccagtg   1500

aaagaacttc tgaagaccat ccccaaatac aagttaggga ttcacggtta tgcctttgca   1560

atcacaaata atggrtatat cctgacgcat ccggaactca ggctgctgta cgaagaagga   1620

aaaaagcgaa ggaaacctaa ctatagtagc gttgacctct ctgaggtgga gtgggaagac   1680

cgagatgacg tgttgagaaa tgctatggtg aatcgaaaga cggggaagtt ttccatggag   1740

gtgaagaaga cagtggacaa agggaaacgg gttttggtga tgacaaatga ctactattat   1800

acagacatca agggtactcc tttcagttta ggtgtggcgc tttccagagg tcatgggaaa   1860

tatttcttcc gagggaatgt aaccatcgaa gaaggcctgc atgacttaga acatcccgat   1920

gtgtccttgg cagatgaatg gtcctactgc aacactgacc tacaccctga gcaccgccat   1980

ctgtctcagt tagaagcgat taagctctac ctaaaaggca aagaacctct gctccagtgt   2040

gataaagaat tgatccaaga agtccttttt gacgcggtgg tgagtgcccc cattgaagcg   2100

tattggacca gcctggccct caacaaatct gaaaattctg acaagggcgt ggaggttgcc   2160

ttcctcggca ctcgcacggg cctctccaga atcaacctgt ttgtcggggc tgagcagctc   2220

accaatcagg acttcctgaa agctggcgac aaggagaaca tttttaacgc agaccatttc   2280

cctctctggt accgaagagc cgctgagcag attccaggga gcttcgtcta ctcgatccca   2340

ttcagcactg gaccagtcaa taaaagcaat gtggtgacag caagtacatc catccagctc   2400

ctggatgaac ggaaatctcc tgtggtggca gctgtaggca ttcagatgaa acttgaattt   2460

ttccaaagga agttctggac tgccagcaga cagtgtgctt ccctggatgg caaatgctcc   2520

atcagctgtg atgatgagac tgtgaattgt tacctcatag acaataatgg atttattttg   2580

gtgtctgaag actacacaca gactggagac tttttttggtg agatcgaggg agctgtgatg   2640

aacaaattgc taacaatggg ctcctttaaa agaattaccc tttatgacta ccaagccatg   2700

tgtagagcca acaaggaaag cagcgatggc gcccatggcc tcctggatcc ttataatgcc   2760

ttcctctctg cagtaaaatg gatcatgaca gaacttgtct tgttcctggt ggaatttaac   2820

ctctgcagtt ggtggcactc cgatatgaca gctaaagccc agaaattgaa acagaccctg   2880

gagccttgtg atactgaata tccagcattc gtctctgagc gcaccatcaa ggagactaca   2940

gggaatattg cttgtgaaga ctgctccaag tcctttgtca tccagcaaat cccaagcagc   3000

aacctgttca tggtggtggt ggacagcagc tgcctctgtg aatctgtggc ccccatcacc   3060

atggcaccca ttgaaatcag gtataatgaa tcccttaagt gtgaacgtct aaaggcccag   3120

aagatcagaa gggcccagaa gatcagaagg cgcccagaat cttgtcatgg cttccatcct   3180

gaggagaatg caagggagtg tgggggtgcg ccg                                3213
```

<210> SEQ ID NO 10
<211> LENGTH: 1019
<212> TYPE: PRT
<213> ORGANISM: Homo sapiens

<400> SEQUENCE: 10

-continued

```
Met Ala Gly Pro Gly Ser Pro Arg Arg Ala Ser Arg Gly Ala Ser Ala
  1               5                  10                  15

Leu Leu Ala Ala Ala Leu Leu Tyr Ala Ala Leu Gly Asp Val Val Arg
             20                  25                  30

Ser Glu Gln Gln Ile Pro Leu Ser Val Val Lys Leu Trp Ala Ser Ala
         35                  40                  45

Phe Gly Gly Glu Ile Lys Ser Ile Ala Ala Lys Tyr Ser Gly Ser Gln
     50                  55                  60

Leu Leu Gln Lys Lys Tyr Lys Glu Tyr Glu Lys Asp Val Ala Ile Glu
 65                  70                  75                  80

Glu Ile Asp Gly Leu Gln Leu Val Lys Lys Leu Ala Lys Asn Met Glu
                 85                  90                  95

Glu Met Phe His Lys Lys Ser Glu Ala Val Arg Arg Leu Val Glu Ala
            100                 105                 110

Ala Glu Glu Ala His Leu Lys His Glu Phe Asp Ala Asp Leu Gln Tyr
        115                 120                 125

Glu Tyr Phe Asn Ala Val Leu Ile Asn Glu Arg Asp Lys Asp Gly Asn
    130                 135                 140

Phe Leu Glu Leu Gly Lys Glu Phe Ile Leu Ala Pro Asn Asp His Phe
145                 150                 155                 160

Asn Asn Leu Pro Val Asn Ile Ser Leu Ser Asp Val Gln Val Pro Thr
                165                 170                 175

Asn Met Tyr Asn Lys Asp Pro Ala Ile Val Asn Gly Val Tyr Trp Ser
            180                 185                 190

Glu Ser Leu Asn Lys Val Phe Val Asp Asn Phe Asp Arg Asp Pro Ser
        195                 200                 205

Leu Ile Trp Gln Tyr Phe Gly Ser Ala Lys Gly Phe Phe Arg Gln Tyr
    210                 215                 220

Pro Gly Ile Lys Trp Glu Pro Asp Glu Asn Gly Val Ile Ala Phe Asp
225                 230                 235                 240

Cys Arg Asn Arg Lys Trp Tyr Ile Gln Ala Ala Thr Ser Pro Lys Asp
                245                 250                 255

Val Val Ile Leu Val Asp Val Ser Gly Ser Met Lys Gly Leu Arg Leu
            260                 265                 270

Thr Ile Ala Lys Gln Thr Val Ser Ser Ile Leu Asp Thr Leu Gly Asp
        275                 280                 285

Asp Asp Phe Phe Asn Ile Ile Ala Tyr Asn Glu Glu Leu His Tyr Val
    290                 295                 300

Glu Pro Cys Leu Asn Gly Thr Leu Val Gln Ala Asp Arg Thr Asn Lys
305                 310                 315                 320

Glu His Phe Arg Glu His Leu Asp Lys Leu Phe Ala Lys Gly Ile Gly
                325                 330                 335

Met Leu Asp Ile Ala Leu Asn Glu Ala Phe Asn Ile Leu Ser Asp Phe
            340                 345                 350

Asn His Thr Gly Gln Gly Ser Ile Cys Ser Gln Ala Ile Met Leu Ile
        355                 360                 365

Thr Asp Gly Ala Val Asp Thr Tyr Asp Thr Ile Phe Ala Lys Tyr Asn
    370                 375                 380

Trp Pro Asp Arg Lys Val Arg Ile Phe Thr Tyr Leu Ile Gly Arg Glu
385                 390                 395                 400

Ala Ala Phe Ala Asp Asn Leu Lys Trp Met Ala Cys Ala Asn Lys Gly
                405                 410                 415

Phe Phe Thr Gln Ile Ser Thr Leu Ala Asp Val Gln Glu Asn Val Met
```

-continued

```
            420                 425                 430

Glu Tyr Leu His Val Leu Ser Arg Pro Lys Val Ile Asp Gln Glu His
        435                 440                 445

Asp Val Val Trp Thr Glu Ala Tyr Ile Asp Ser Thr Leu Thr Asp Asp
    450                 455                 460

Gln Gly Pro Val Leu Met Thr Thr Val Ala Met Pro Val Phe Ser Lys
465                 470                 475                 480

Gln Asn Glu Thr Arg Ser Lys Gly Ile Leu Leu Gly Val Val Gly Thr
                485                 490                 495

Asp Val Pro Val Lys Glu Leu Leu Lys Thr Ile Pro Lys Tyr Lys Leu
            500                 505                 510

Gly Ile His Gly Tyr Ala Phe Ala Ile Thr Asn Asn Gly Tyr Ile Leu
        515                 520                 525

Thr His Pro Glu Leu Arg Leu Leu Tyr Glu Glu Gly Lys Lys Arg Arg
    530                 535                 540

Lys Pro Asn Tyr Ser Ser Val Asp Leu Ser Glu Val Glu Trp Glu Asp
545                 550                 555                 560

Arg Asp Asp Val Leu Arg Asn Ala Met Val Asn Arg Lys Thr Gly Lys
                565                 570                 575

Phe Ser Met Glu Val Lys Lys Thr Val Asp Lys Gly Lys Arg Val Leu
            580                 585                 590

Val Met Thr Asn Asp Tyr Tyr Tyr Thr Asp Ile Lys Gly Thr Pro Phe
        595                 600                 605

Ser Leu Gly Val Ala Leu Ser Arg Gly His Gly Lys Tyr Phe Phe Arg
    610                 615                 620

Gly Asn Val Thr Ile Glu Glu Gly Leu His Asp Leu Glu His Pro Asp
625                 630                 635                 640

Val Ser Leu Ala Asp Glu Trp Ser Tyr Cys Asn Thr Asp Leu His Pro
                645                 650                 655

Glu His Arg His Leu Ser Gln Leu Glu Ala Ile Lys Leu Tyr Leu Lys
            660                 665                 670

Gly Lys Glu Pro Leu Leu Gln Cys Asp Lys Glu Leu Ile Gln Glu Val
        675                 680                 685

Leu Phe Asp Ala Val Val Ser Ala Pro Ile Glu Ala Tyr Trp Thr Ser
    690                 695                 700

Leu Ala Leu Asn Lys Ser Glu Asn Ser Asp Lys Gly Val Glu Val Ala
705                 710                 715                 720

Phe Leu Gly Thr Arg Thr Gly Leu Ser Arg Ile Asn Leu Phe Val Gly
                725                 730                 735

Ala Glu Gln Leu Thr Asn Gln Asp Phe Leu Lys Ala Gly Asp Lys Glu
            740                 745                 750

Asn Ile Phe Asn Ala Asp His Phe Pro Leu Trp Tyr Arg Arg Ala Ala
        755                 760                 765

Glu Gln Ile Pro Gly Ser Phe Val Tyr Ser Ile Pro Phe Ser Thr Gly
    770                 775                 780

Pro Val Asn Lys Ser Asn Val Val Thr Ala Ser Thr Ser Ile Gln Leu
785                 790                 795                 800

Leu Asp Glu Arg Lys Ser Pro Val Val Ala Ala Val Gly Ile Gln Met
                805                 810                 815

Lys Leu Glu Phe Phe Gln Arg Lys Phe Trp Thr Ala Ser Arg Gln Cys
            820                 825                 830

Ala Ser Leu Asp Gly Lys Cys Ser Ile Ser Cys Asp Asp Glu Thr Val
        835                 840                 845
```

-continued

```
Asn Cys Tyr Leu Ile Asp Asn Asn Gly Phe Ile Leu Val Ser Glu Asp
    850                 855                 860

Tyr Thr Gln Thr Gly Asp Phe Phe Gly Glu Ile Glu Gly Ala Val Met
865                 870                 875                 880

Asn Lys Leu Leu Thr Met Gly Ser Phe Lys Arg Ile Thr Leu Tyr Asp
                885                 890                 895

Tyr Gln Ala Met Cys Arg Ala Asn Lys Glu Ser Ser Asp Gly Ala His
            900                 905                 910

Gly Leu Leu Asp Pro Tyr Asn Ala Phe Leu Ser Ala Val Lys Trp Ile
        915                 920                 925

Met Thr Glu Leu Val Leu Phe Leu Val Glu Phe Asn Leu Cys Ser Trp
    930                 935                 940

Trp His Ser Asp Met Thr Ala Lys Ala Gln Lys Leu Lys Gln Thr Leu
945                 950                 955                 960

Glu Pro Cys Asp Thr Glu Tyr Pro Ala Phe Val Ser Glu Arg Thr Ile
                965                 970                 975

Lys Glu Thr Thr Gly Asn Ile Ala Cys Glu Asp Cys Ser Lys Ser Phe
            980                 985                 990

Val Ile Gln Gln Ile Pro Ser Ser Asn Leu Phe Met Val Val Val Asp
        995                1000                1005

Ser Ser Cys Leu Cys Glu Ser Val Ala Pro Ile
   1010                1015


<210> SEQ ID NO 11
<211> LENGTH: 1038
<212> TYPE: PRT
<213> ORGANISM: Homo sapiens

<400> SEQUENCE: 11

Met Ala Gly Pro Gly Ser Pro Arg Arg Ala Ser Arg Gly Ala Ser Ala
  1               5                  10                  15

Leu Leu Ala Ala Ala Leu Leu Tyr Ala Ala Leu Gly Asp Val Val Arg
            20                  25                  30

Ser Glu Gln Gln Ile Pro Leu Ser Val Val Lys Leu Trp Ala Ser Ala
        35                  40                  45

Phe Gly Gly Glu Ile Lys Ser Ile Ala Ala Lys Tyr Ser Gly Ser Gln
     50                  55                  60

Leu Leu Gln Lys Lys Tyr Lys Glu Tyr Glu Lys Asp Val Ala Ile Glu
 65                  70                  75                  80

Glu Ile Asp Gly Leu Gln Leu Val Lys Lys Leu Ala Lys Asn Met Glu
                 85                  90                  95

Glu Met Phe His Lys Lys Ser Glu Ala Val Arg Arg Leu Val Glu Ala
            100                 105                 110

Ala Glu Glu Ala His Leu Lys His Glu Phe Asp Ala Asp Leu Gln Tyr
        115                 120                 125

Glu Tyr Phe Asn Ala Val Leu Ile Asn Glu Arg Asp Lys Asp Gly Asn
    130                 135                 140

Phe Leu Glu Leu Gly Lys Glu Phe Ile Leu Ala Pro Asn Asp His Phe
145                 150                 155                 160

Asn Asn Leu Pro Val Asn Ile Ser Leu Ser Asp Val Gln Val Pro Thr
                165                 170                 175

Asn Met Tyr Asn Lys Asp Pro Ala Ile Val Asn Gly Val Tyr Trp Ser
            180                 185                 190

Glu Ser Leu Asn Lys Val Phe Val Asp Asn Phe Asp Arg Asp Pro Ser
```

-continued

```
        195                 200                 205

Leu Ile Trp Gln Tyr Phe Gly Ser Ala Lys Gly Phe Phe Arg Gln Tyr
    210                 215                 220

Pro Gly Ile Lys Trp Glu Pro Asp Glu Asn Gly Val Ile Ala Phe Asp
225                 230                 235                 240

Cys Arg Asn Arg Lys Trp Tyr Ile Gln Ala Ala Thr Ser Pro Lys Asp
                245                 250                 255

Val Val Ile Leu Val Asp Val Ser Gly Ser Met Lys Gly Leu Arg Leu
            260                 265                 270

Thr Ile Ala Lys Gln Thr Val Ser Ser Ile Leu Asp Thr Leu Gly Asp
        275                 280                 285

Asp Asp Phe Phe Asn Ile Ile Ala Tyr Asn Glu Glu Leu His Tyr Val
    290                 295                 300

Glu Pro Cys Leu Asn Gly Thr Leu Val Gln Ala Asp Arg Thr Asn Lys
305                 310                 315                 320

Glu His Phe Arg Glu His Leu Asp Lys Leu Phe Ala Lys Gly Ile Gly
                325                 330                 335

Met Leu Asp Ile Ala Leu Asn Glu Ala Phe Asn Ile Leu Ser Asp Phe
            340                 345                 350

Asn His Thr Gly Gln Gly Ser Ile Cys Ser Gln Ala Ile Met Leu Ile
        355                 360                 365

Thr Asp Gly Ala Val Asp Thr Tyr Asp Thr Ile Phe Ala Lys Tyr Asn
    370                 375                 380

Trp Pro Asp Arg Lys Val Arg Ile Phe Thr Tyr Leu Ile Gly Arg Glu
385                 390                 395                 400

Ala Ala Phe Ala Asp Asn Leu Lys Trp Met Ala Cys Ala Asn Lys Gly
                405                 410                 415

Phe Phe Thr Gln Ile Ser Thr Leu Ala Asp Val Gln Glu Asn Val Met
            420                 425                 430

Glu Tyr Leu His Val Leu Ser Arg Pro Lys Val Ile Asp Gln Glu His
        435                 440                 445

Asp Val Val Trp Thr Glu Ala Tyr Ile Asp Ser Thr Leu Thr Asp Asp
    450                 455                 460

Gln Gly Pro Val Leu Met Thr Thr Val Ala Met Pro Val Phe Ser Lys
465                 470                 475                 480

Gln Asn Glu Thr Arg Ser Lys Gly Ile Leu Leu Gly Val Val Gly Thr
                485                 490                 495

Asp Val Pro Val Lys Glu Leu Leu Lys Thr Ile Pro Lys Tyr Lys Leu
            500                 505                 510

Gly Ile His Gly Tyr Ala Phe Ala Ile Thr Asn Asn Gly Tyr Ile Leu
        515                 520                 525

Thr His Pro Glu Leu Arg Leu Leu Tyr Glu Glu Gly Lys Lys Arg Arg
    530                 535                 540

Lys Pro Asn Tyr Ser Ser Val Asp Leu Ser Glu Val Glu Trp Glu Asp
545                 550                 555                 560

Arg Asp Asp Val Leu Arg Asn Ala Met Val Asn Arg Lys Thr Gly Lys
                565                 570                 575

Phe Ser Met Glu Val Lys Lys Thr Val Asp Lys Gly Lys Arg Val Leu
            580                 585                 590

Val Met Thr Asn Asp Tyr Tyr Tyr Thr Asp Ile Lys Gly Thr Pro Phe
        595                 600                 605

Ser Leu Gly Val Ala Leu Ser Arg Gly His Gly Lys Tyr Phe Phe Arg
    610                 615                 620
```

-continued

```
Gly Asn Val Thr Ile Glu Glu Gly Leu His Asp Leu Glu His Pro Asp
625                 630                 635                 640

Val Ser Leu Ala Asp Glu Trp Ser Tyr Cys Asn Thr Asp Leu His Pro
                645                 650                 655

Glu His Arg His Leu Ser Gln Leu Glu Ala Ile Lys Leu Tyr Leu Lys
            660                 665                 670

Gly Lys Glu Pro Leu Leu Gln Cys Asp Lys Glu Leu Ile Gln Glu Val
        675                 680                 685

Leu Phe Asp Ala Val Val Ser Ala Pro Ile Glu Ala Tyr Trp Thr Ser
    690                 695                 700

Leu Ala Leu Asn Lys Ser Glu Asn Ser Asp Lys Gly Val Glu Val Ala
705                 710                 715                 720

Phe Leu Gly Thr Arg Thr Gly Leu Ser Arg Ile Asn Leu Phe Val Gly
                725                 730                 735

Ala Glu Gln Leu Thr Asn Gln Asp Phe Leu Lys Ala Gly Asp Lys Glu
            740                 745                 750

Asn Ile Phe Asn Ala Asp His Phe Pro Leu Trp Tyr Arg Arg Ala Ala
        755                 760                 765

Glu Gln Ile Pro Gly Ser Phe Val Tyr Ser Ile Pro Phe Ser Thr Gly
    770                 775                 780

Pro Val Asn Lys Ser Asn Val Val Thr Ala Ser Thr Ser Ile Gln Leu
785                 790                 795                 800

Leu Asp Glu Arg Lys Ser Pro Val Val Ala Ala Val Gly Ile Gln Met
                805                 810                 815

Lys Leu Glu Phe Phe Gln Arg Lys Phe Trp Thr Ala Ser Arg Gln Cys
            820                 825                 830

Ala Ser Leu Asp Gly Lys Cys Ser Ile Ser Cys Asp Asp Glu Thr Val
        835                 840                 845

Asn Cys Tyr Leu Ile Asp Asn Asn Gly Phe Ile Leu Val Ser Glu Asp
    850                 855                 860

Tyr Thr Gln Thr Gly Asp Phe Phe Gly Glu Ile Glu Gly Ala Val Met
865                 870                 875                 880

Asn Lys Leu Leu Thr Met Gly Ser Phe Lys Arg Ile Thr Leu Tyr Asp
                885                 890                 895

Tyr Gln Ala Met Cys Arg Ala Asn Lys Glu Ser Ser Asp Gly Ala His
            900                 905                 910

Gly Leu Leu Asp Pro Tyr Asn Ala Phe Leu Ser Ala Val Lys Trp Ile
        915                 920                 925

Met Thr Glu Leu Val Leu Phe Leu Val Glu Phe Asn Leu Cys Ser Trp
    930                 935                 940

Trp His Ser Asp Met Thr Ala Lys Ala Gln Lys Leu Lys Gln Thr Leu
945                 950                 955                 960

Glu Pro Cys Asp Thr Glu Tyr Pro Ala Phe Val Ser Glu Arg Thr Ile
                965                 970                 975

Lys Glu Thr Thr Gly Asn Ile Ala Cys Glu Asp Cys Ser Lys Ser Phe
            980                 985                 990

Val Ile Gln Gln Ile Pro Ser Ser Asn Leu Phe Met Val Val Val Asp
        995                 1000                1005

Ser Ser Cys Leu Cys Glu Ser Val Ala Pro Ile Thr Met Ala Pro Ile
   1010                 1015                1020

Glu Ile Arg Tyr Asn Glu Ser Leu Lys Cys Glu Arg Leu Lys
1025                1030                1035
```

<210> SEQ ID NO 12
<211> LENGTH: 1065
<212> TYPE: PRT
<213> ORGANISM: Homo sapiens

<400> SEQUENCE: 12

```
Met Ala Gly Pro Gly Ser Pro Arg Arg Ala Ser Arg Gly Ala Ser Ala
  1               5                  10                  15

Leu Leu Ala Ala Ala Leu Leu Tyr Ala Ala Leu Gly Asp Val Val Arg
             20                  25                  30

Ser Glu Gln Gln Ile Pro Leu Ser Val Val Lys Leu Trp Ala Ser Ala
         35                  40                  45

Phe Gly Gly Glu Ile Lys Ser Ile Ala Ala Lys Tyr Ser Gly Ser Gln
     50                  55                  60

Leu Leu Gln Lys Lys Tyr Lys Glu Tyr Glu Lys Asp Val Ala Ile Glu
 65                  70                  75                  80

Glu Ile Asp Gly Leu Gln Leu Val Lys Lys Leu Ala Lys Asn Met Glu
                 85                  90                  95

Glu Met Phe His Lys Lys Ser Glu Ala Val Arg Arg Leu Val Glu Ala
            100                 105                 110

Ala Glu Glu Ala His Leu Lys His Glu Phe Asp Ala Asp Leu Gln Tyr
        115                 120                 125

Glu Tyr Phe Asn Ala Val Leu Ile Asn Glu Arg Asp Lys Asp Gly Asn
    130                 135                 140

Phe Leu Glu Leu Gly Lys Glu Phe Ile Leu Ala Pro Asn Asp His Phe
145                 150                 155                 160

Asn Asn Leu Pro Val Asn Ile Ser Leu Ser Asp Val Gln Val Pro Thr
                165                 170                 175

Asn Met Tyr Asn Lys Asp Pro Ala Ile Val Asn Gly Val Tyr Trp Ser
            180                 185                 190

Glu Ser Leu Asn Lys Val Phe Val Asp Asn Phe Asp Arg Asp Pro Ser
        195                 200                 205

Leu Ile Trp Gln Tyr Phe Gly Ser Ala Lys Gly Phe Phe Arg Gln Tyr
    210                 215                 220

Pro Gly Ile Lys Trp Glu Pro Asp Glu Asn Gly Val Ile Ala Phe Asp
225                 230                 235                 240

Cys Arg Asn Arg Lys Trp Tyr Ile Gln Ala Ala Thr Ser Pro Lys Asp
                245                 250                 255

Val Val Ile Leu Val Asp Val Ser Gly Ser Met Lys Gly Leu Arg Leu
            260                 265                 270

Thr Ile Ala Lys Gln Thr Val Ser Ser Ile Leu Asp Thr Leu Gly Asp
        275                 280                 285

Asp Asp Phe Phe Asn Ile Ile Ala Tyr Asn Glu Glu Leu His Tyr Val
    290                 295                 300

Glu Pro Cys Leu Asn Gly Thr Leu Val Gln Ala Asp Arg Thr Asn Lys
305                 310                 315                 320

Glu His Phe Arg Glu His Leu Asp Lys Leu Phe Ala Lys Gly Ile Gly
                325                 330                 335

Met Leu Asp Ile Ala Leu Asn Glu Ala Phe Asn Ile Leu Ser Asp Phe
            340                 345                 350

Asn His Thr Gly Gln Gly Ser Ile Cys Ser Gln Ala Ile Met Leu Ile
        355                 360                 365

Thr Asp Gly Ala Val Asp Thr Tyr Asp Thr Ile Phe Ala Lys Tyr Asn
    370                 375                 380
```

```
Trp Pro Asp Arg Lys Val Arg Ile Phe Thr Tyr Leu Ile Gly Arg Glu
385                 390                 395                 400

Ala Ala Phe Ala Asp Asn Leu Lys Trp Met Ala Cys Ala Asn Lys Gly
                405                 410                 415

Phe Phe Thr Gln Ile Ser Thr Leu Ala Asp Val Gln Glu Asn Val Met
            420                 425                 430

Glu Tyr Leu His Val Leu Ser Arg Pro Lys Val Ile Asp Gln Glu His
        435                 440                 445

Asp Val Val Trp Thr Glu Ala Tyr Ile Asp Ser Thr Leu Thr Asp Asp
    450                 455                 460

Gln Gly Pro Val Leu Met Thr Thr Val Ala Met Pro Val Phe Ser Lys
465                 470                 475                 480

Gln Asn Glu Thr Arg Ser Lys Gly Ile Leu Leu Gly Val Val Gly Thr
                485                 490                 495

Asp Val Pro Val Lys Glu Leu Leu Lys Thr Ile Pro Lys Tyr Lys Leu
            500                 505                 510

Gly Ile His Gly Tyr Ala Phe Ala Ile Thr Asn Asn Gly Tyr Ile Leu
        515                 520                 525

Thr His Pro Glu Leu Arg Leu Leu Tyr Glu Glu Gly Lys Lys Arg Arg
    530                 535                 540

Lys Pro Asn Tyr Ser Ser Val Asp Leu Ser Glu Val Glu Trp Glu Asp
545                 550                 555                 560

Arg Asp Asp Val Leu Arg Asn Ala Met Val Asn Arg Lys Thr Gly Lys
                565                 570                 575

Phe Ser Met Glu Val Lys Lys Thr Val Asp Lys Gly Lys Arg Val Leu
            580                 585                 590

Val Met Thr Asn Asp Tyr Tyr Tyr Thr Asp Ile Lys Gly Thr Pro Phe
        595                 600                 605

Ser Leu Gly Val Ala Leu Ser Arg Gly His Gly Lys Tyr Phe Phe Arg
    610                 615                 620

Gly Asn Val Thr Ile Glu Glu Gly Leu His Asp Leu Glu His Pro Asp
625                 630                 635                 640

Val Ser Leu Ala Asp Glu Trp Ser Tyr Cys Asn Thr Asp Leu His Pro
                645                 650                 655

Glu His Arg His Leu Ser Gln Leu Glu Ala Ile Lys Leu Tyr Leu Lys
            660                 665                 670

Gly Lys Glu Pro Leu Leu Gln Cys Asp Lys Glu Leu Ile Gln Glu Val
        675                 680                 685

Leu Phe Asp Ala Val Val Ser Ala Pro Ile Glu Ala Tyr Trp Thr Ser
    690                 695                 700

Leu Ala Leu Asn Lys Ser Glu Asn Ser Asp Lys Gly Val Glu Val Ala
705                 710                 715                 720

]Phe Leu Gly Thr Arg Thr Gly Leu Ser Arg Ile Asn Leu Phe Val Gly
                725                 730                 735
A
la Glu Gln Leu Thr Asn Gln Asp Phe Leu Lys Ala Gly Asp Lys Glu
            740                 745                 750

Asn Ile Phe Asn Ala Asp His Phe Pro Leu Trp Tyr Arg Arg Ala Ala
        755                 760                 765

Glu Gln Ile Pro Gly Ser Phe Val Tyr Ser Ile Pro Phe Ser Thr Gly
    770                 775                 780

Pro Val Asn Lys Ser Asn Val Val Thr Ala Ser Thr Ser Ile Gln Leu
785                 790                 795                 800
```

-continued

```
Leu Asp Glu Arg Lys Ser Pro Val Val Ala Ala Val Gly Ile Gln Met
                805                 810                 815

Lys Leu Glu Phe Phe Gln Arg Lys Phe Trp Thr Ala Ser Arg Gln Cys
            820                 825                 830

Ala Ser Leu Asp Gly Lys Cys Ser Ile Ser Cys Asp Asp Glu Thr Val
        835                 840                 845

Asn Cys Tyr Leu Ile Asp Asn Asn Gly Phe Ile Leu Val Ser Glu Asp
    850                 855                 860

Tyr Thr Gln Thr Gly Asp Phe Phe Gly Glu Ile Glu Gly Ala Val Met
865                 870                 875                 880

Asn Lys Leu Leu Thr Met Gly Ser Phe Lys Arg Ile Thr Leu Tyr Asp
                885                 890                 895

Tyr Gln Ala Met Cys Arg Ala Asn Lys Glu Ser Ser Asp Gly Ala His
            900                 905                 910

Gly Leu Leu Asp Pro Tyr Asn Ala Phe Leu Ser Ala Val Lys Trp Ile
        915                 920                 925

Met Thr Glu Leu Val Leu Phe Leu Val Glu Phe Asn Leu Cys Ser Trp
    930                 935                 940

Trp His Ser Asp Met Thr Ala Lys Ala Gln Lys Leu Lys Gln Thr Leu
945                 950                 955                 960

Glu Pro Cys Asp Thr Glu Tyr Pro Ala Phe Val Ser Glu Arg Thr Ile
                965                 970                 975

Lys Glu Thr Thr Gly Asn Ile Ala Cys Glu Asp Cys Ser Lys Ser Phe
            980                 985                 990

Val Ile Gln Gln Ile Pro Ser Ser Asn Leu Phe Met Val Val Val Asp
        995                1000                1005

Ser Ser Cys Leu Cys Glu Ser Val Ala Pro Ile Thr Met Ala Pro Ile
   1010                1015                1020

Glu Ile Arg Tyr Asn Glu Ser Leu Lys Cys Glu Arg Leu Lys Ala Gln
1025               1030                1035                1040

Lys Ile Arg Arg Arg Pro Glu Ser Cys His Gly Phe His Pro Glu Glu
               1045                1050                1055

Asn Ala Arg Glu Cys Gly Gly Ala Pro
           1060                1065


<210> SEQ ID NO 13
<211> LENGTH: 912
<212> TYPE: DNA
<213> ORGANISM: Homo sapiens

<400> SEQUENCE: 13

agtggcctcc tgagaagcag cttgttcgtg ggctccgaga aggtctccga caggaagttc      60

ctgacacctg aggacgaggc cagcgtgttc accctggacc gcttcccgct gtggtaccgc     120

caggcctcag agcatcctgc tggcagcttc gtcttcaacc tccgctgggc agaaggacca     180

gaaagtgcgg gtgaacccat ggtggtgacg gcaagcacag ctgtggcggt gaccgtggac     240

aagaggacag ccattgctgc agccgcgggc gtccaaatga agctggaatt cctccagcgc     300

aaattctggg cggcaacgcg gcagtgcagc actgtggatg ggccgtgcac acagagctgc     360

gaggacagtg atctggactg cttcgtcatc gacaacaacg ggttcattct gatctccaag     420

aggtcccgag agacgggaag atttctgggg gaggtggatg gtgctgtcct gacccagctg     480

ctcagcatgg gggtgttcag ccaagtgact atgtatgact atcaggccat gtgcaaaccc     540

tcgagtcacc accacagtgc agcccagccc ctggtcagcc caatttctgc cttcttgacg     600
```

-continued

```
gcgaccaggt ggctgctgca ggagctggtg ctgttcctgc tggagtggag tgtctggggc    660

tcctggtacg acagaggggc cgaggccaaa agtgtcttcc atcactccca caaacacaag    720

aagcaggacc cgctgcagcc ctgcgacacg gagtaccccg tgttcgtgta ccagccggcc    780

atccgggagg ccaacgggat cgtggagtgc gggccctgcc agaaggtatt tgtggtgcag    840

cagattccca acagtaacct cctcctcctg gtgacagacc ccacctgtga ctgcagcatc    900

ttcccaccag tg                                                        912
```

<210> SEQ ID NO 14
<211> LENGTH: 969
<212> TYPE: DNA
<213> ORGANISM: Homo sapiens

<400> SEQUENCE: 14

```
agtggcctcc tgagaagcag cttgttcgtg ggctccgaga aggtctccga caggaagttc     60

ctgacacctg aggacgaggc cagcgtgttc accctggacc gcttcccgct gtggtaccgc    120

caggcctcag agcatcctgc tggcagcttc gtcttcaacc tccgctgggc agaaggacca    180

gaaagtgcgg gtgaacccat ggtggtgacg gcaagcacag ctgtggcggt gaccgtggac    240

aagaggacag ccattgctgc agccgcgggc gtccaaatga agctggaatt cctccagcgc    300

aaattctggg cggcaacgcg gcagtgcagc actgtggatg ggccgtgcac acagagctgc    360

gaggacagtg atctggactg cttcgtcatc gacaacaacg ggttcattct gatctccaag    420

aggtcccgag agacgggaag atttctgggg gaggtggatg gtgctgtcct gacccagctg    480

ctcagcatgg gggtgttcag ccaagtgact atgtatgact atcaggccat gtgcaaaccc    540

tcgagtcacc accacagtgc agcccagccc ctggtcagcc caatttctgc cttcttgacg    600

gcgaccaggt ggctgctgca ggagctggtg ctgttcctgc tggagtggag tgtctggggc    660

tcctggtacg acagaggggc cgaggccaaa agtgtcttcc atcactccca caaacacaag    720

aagcaggacc cgctgcagcc ctgcgacacg gagtaccccg tgttcgtgta ccagccggcc    780

atccgggagg ccaacgggat cgtggagtgc gggccctgcc agaaggtatt tgtggtgcag    840

cagattccca acagtaacct cctcctcctg gtgacagacc ccacctgtga ctgcagcatc    900

ttcccaccag tgctgcagga ggcgacagaa gtcaaatata atgcctctgt caaatgtgac    960

cggatgcgc                                                            969
```

<210> SEQ ID NO 15
<211> LENGTH: 1050
<212> TYPE: DNA
<213> ORGANISM: Homo sapiens

<400> SEQUENCE: 15

```
agtggcctcc tgagaagcag cttgttcgtg ggctccgaga aggtctccga caggaagttc     60

ctgacacctg aggacgaggc cagcgtgttc accctggacc gcttcccgct gtggtaccgc    120

caggcctcag agcatcctgc tggcagcttc gtcttcaacc tccgctgggc agaaggacca    180

gaaagtgcgg gtgaacccat ggtggtgacg gcaagcacag ctgtggcggt gaccgtggac    240

aagaggacag ccattgctgc agccgcgggc gtccaaatga agctggaatt cctccagcgc    300

aaattctggg cggcaacgcg gcagtgcagc actgtggatg ggccgtgcac acagagctgc    360

gaggacagtg atctggactg cttcgtcatc gacaacaacg ggttcattct gatctccaag    420

aggtcccgag agacgggaag atttctgggg gaggtggatg gtgctgtcct gacccagctg    480

ctcagcatgg gggtgttcag ccaagtgact atgtatgact atcaggccat gtgcaaaccc    540
```

```
tcgagtcacc accacagtgc agcccagccc ctggtcagcc caatttctgc cttcttgacg    600

gcgaccaggt ggctgctgca ggagctggtg ctgttcctgc tggagtggag tgtctggggc    660

tcctggtacg acagaggggc cgaggccaaa agtgtcttcc atcactccca caaacacaag    720

aagcaggacc cgctgcagcc ctgcgacacg gagtaccccg tgttcgtgta ccagccggcc    780

atccgggagg ccaacgggat cgtggagtgc gggccctgcc agaaggtatt tgtggtgcag    840

cagattccca acagtaacct cctcctcctg gtgacagacc ccacctgtga ctgcagcatc    900

ttcccaccag tgctgcagga ggcgacagaa gtcaaatata atgcctctgt caaatgtgac    960

cggatgcgct cccagaagct ccgccggcga ccagactcct gccacgcctt ccatccagag   1020

gagaatgccc aggactgcgg cggcgcctcg                                    1050
```

```
<210> SEQ ID NO 16
<211> LENGTH: 304
<212> TYPE: PRT
<213> ORGANISM: Homo sapiens

<400> SEQUENCE: 16

Ser Gly Leu Leu Arg Ser Ser Leu Phe Val Gly Ser Glu Lys Val Ser
  1               5                  10                  15

Asp Arg Lys Phe Leu Thr Pro Glu Asp Glu Ala Ser Val Phe Thr Leu
             20                  25                  30

Asp Arg Phe Pro Leu Trp Tyr Arg Gln Ala Ser Glu His Pro Ala Gly
         35                  40                  45

Ser Phe Val Phe Asn Leu Arg Trp Ala Glu Gly Pro Glu Ser Ala Gly
     50                  55                  60

Glu Pro Met Val Val Thr Ala Ser Thr Ala Val Ala Val Thr Val Asp
 65                  70                  75                  80

Lys Arg Thr Ala Ile Ala Ala Ala Ala Gly Val Gln Met Lys Leu Glu
                 85                  90                  95

Phe Leu Gln Arg Lys Phe Trp Ala Ala Thr Arg Gln Cys Ser Thr Val
            100                 105                 110

Asp Gly Pro Cys Thr Gln Ser Cys Glu Asp Ser Asp Leu Asp Cys Phe
        115                 120                 125

Val Ile Asp Asn Asn Gly Phe Ile Leu Ile Ser Lys Arg Ser Arg Glu
    130                 135                 140

Thr Gly Arg Phe Leu Gly Glu Val Asp Gly Ala Val Leu Thr Gln Leu
145                 150                 155                 160

Leu Ser Met Gly Val Phe Ser Gln Val Thr Met Tyr Asp Tyr Gln Ala
                165                 170                 175

Met Cys Lys Pro Ser Ser His His His Ser Ala Ala Gln Pro Leu Val
            180                 185                 190

Ser Pro Ile Ser Ala Phe Leu Thr Ala Thr Arg Trp Leu Leu Gln Glu
        195                 200                 205

Leu Val Leu Phe Leu Leu Glu Trp Ser Val Trp Gly Ser Trp Tyr Asp
    210                 215                 220

Arg Gly Ala Glu Ala Lys Ser Val Phe His His Ser His Lys His Lys
225                 230                 235                 240

Lys Gln Asp Pro Leu Gln Pro Cys Asp Thr Glu Tyr Pro Val Phe Val
                245                 250                 255

Tyr Gln Pro Ala Ile Arg Glu Ala Asn Gly Ile Val Glu Cys Gly Pro
            260                 265                 270

Cys Gln Lys Val Phe Val Val Gln Gln Ile Pro Asn Ser Asn Leu Leu
```

```
        275                 280                 285

Leu Leu Val Thr Asp Pro Thr Cys Asp Cys Ser Ile Phe Pro Pro Val
    290                 295                 300
```

<210> SEQ ID NO 17
<211> LENGTH: 323
<212> TYPE: PRT
<213> ORGANISM: Homo sapiens

<400> SEQUENCE: 17

```
Ser Gly Leu Leu Arg Ser Ser Leu Phe Val Gly Ser Glu Lys Val Ser
  1               5                  10                  15

Asp Arg Lys Phe Leu Thr Pro Glu Asp Glu Ala Ser Val Phe Thr Leu
            20                  25                  30

Asp Arg Phe Pro Leu Trp Tyr Arg Gln Ala Ser Glu His Pro Ala Gly
        35                  40                  45

Ser Phe Val Phe Asn Leu Arg Trp Ala Glu Gly Pro Glu Ser Ala Gly
     50                  55                  60

Glu Pro Met Val Val Thr Ala Ser Thr Ala Val Ala Val Thr Val Asp
 65                  70                  75                  80

Lys Arg Thr Ala Ile Ala Ala Ala Ala Gly Val Gln Met Lys Leu Glu
                 85                  90                  95

Phe Leu Gln Arg Lys Phe Trp Ala Ala Thr Arg Gln Cys Ser Thr Val
            100                 105                 110

Asp Gly Pro Cys Thr Gln Ser Cys Glu Asp Ser Asp Leu Asp Cys Phe
        115                 120                 125

Val Ile Asp Asn Asn Gly Phe Ile Leu Ile Ser Lys Arg Ser Arg Glu
    130                 135                 140

Thr Gly Arg Phe Leu Gly Glu Val Asp Gly Ala Val Leu Thr Gln Leu
145                 150                 155                 160

Leu Ser Met Gly Val Phe Ser Gln Val Thr Met Tyr Asp Tyr Gln Ala
                165                 170                 175

Met Cys Lys Pro Ser Ser His His His Ser Ala Ala Gln Pro Leu Val
            180                 185                 190

Ser Pro Ile Ser Ala Phe Leu Thr Ala Thr Arg Trp Leu Leu Gln Glu
        195                 200                 205

Leu Val Leu Phe Leu Leu Glu Trp Ser Val Trp Gly Ser Trp Tyr Asp
    210                 215                 220

Arg Gly Ala Glu Ala Lys Ser Val Phe His His Ser His Lys His Lys
225                 230                 235                 240

Lys Gln Asp Pro Leu Gln Pro Cys Asp Thr Glu Tyr Pro Val Phe Val
                245                 250                 255

Tyr Gln Pro Ala Ile Arg Glu Ala Asn Gly Ile Val Glu Cys Gly Pro
            260                 265                 270

Cys Gln Lys Val Phe Val Val Gln Gln Ile Pro Asn Ser Asn Leu Leu
        275                 280                 285

Leu Leu Val Thr Asp Pro Thr Cys Asp Cys Ser Ile Phe Pro Pro Val
    290                 295                 300

Leu Gln Glu Ala Thr Glu Val Lys Tyr Asn Ala Ser Val Lys Cys Asp
305                 310                 315                 320

Arg Met Arg
```

<210> SEQ ID NO 18
<211> LENGTH: 350
<212> TYPE: PRT

```
<213> ORGANISM: Homo sapiens

<400> SEQUENCE: 18

Ser Gly Leu Leu Arg Ser Ser Leu Phe Val Gly Ser Glu Lys Val Ser
  1               5                  10                  15

Asp Arg Lys Phe Leu Thr Pro Glu Asp Glu Ala Ser Val Phe Thr Leu
             20                  25                  30

Asp Arg Phe Pro Leu Trp Tyr Arg Gln Ala Ser Glu His Pro Ala Gly
         35                  40                  45

Ser Phe Val Phe Asn Leu Arg Trp Ala Glu Gly Pro Glu Ser Ala Gly
     50                  55                  60

Glu Pro Met Val Val Thr Ala Ser Thr Ala Val Ala Val Thr Val Asp
 65                  70                  75                  80

Lys Arg Thr Ala Ile Ala Ala Ala Ala Gly Val Gln Met Lys Leu Glu
                 85                  90                  95

Phe Leu Gln Arg Lys Phe Trp Ala Ala Thr Arg Gln Cys Ser Thr Val
            100                 105                 110

Asp Gly Pro Cys Thr Gln Ser Cys Glu Asp Ser Asp Leu Asp Cys Phe
        115                 120                 125

Val Ile Asp Asn Asn Gly Phe Ile Leu Ile Ser Lys Arg Ser Arg Glu
    130                 135                 140

Thr Gly Arg Phe Leu Gly Glu Val Asp Gly Ala Val Leu Thr Gln Leu
145                 150                 155                 160

Leu Ser Met Gly Val Phe Ser Gln Val Thr Met Tyr Asp Tyr Gln Ala
                165                 170                 175

Met Cys Lys Pro Ser Ser His His His Ser Ala Ala Gln Pro Leu Val
            180                 185                 190

Ser Pro Ile Ser Ala Phe Leu Thr Ala Thr Arg Trp Leu Leu Gln Glu
        195                 200                 205

Leu Val Leu Phe Leu Leu Glu Trp Ser Val Trp Gly Ser Trp Tyr Asp
    210                 215                 220

Arg Gly Ala Glu Ala Lys Ser Val Phe His His Ser His Lys His Lys
225                 230                 235                 240

Lys Gln Asp Pro Leu Gln Pro Cys Asp Thr Glu Tyr Pro Val Phe Val
                245                 250                 255

Tyr Gln Pro Ala Ile Arg Glu Ala Asn Gly Ile Val Glu Cys Gly Pro
            260                 265                 270

Cys Gln Lys Val Phe Val Val Gln Gln Ile Pro Asn Ser Asn Leu Leu
        275                 280                 285

Leu Leu Val Thr Asp Pro Thr Cys Asp Cys Ser Ile Phe Pro Pro Val
    290                 295                 300

Leu Gln Glu Ala Thr Glu Val Lys Tyr Asn Ala Ser Val Lys Cys Asp
305                 310                 315                 320

Arg Met Arg Ser Gln Lys Leu Arg Arg Arg Pro Asp Ser Cys His Ala
                325                 330                 335

Phe His Pro Glu Glu Asn Ala Gln Asp Cys Gly Gly Ala Ser
            340                 345                 350


<210> SEQ ID NO 19
<211> LENGTH: 5482
<212> TYPE: DNA
<213> ORGANISM: Homo sapiens

<400> SEQUENCE: 19

cgggcagcgc agcccgcaga ggcgctgcgg cccgtgcagc cccggaggcc cctcgcggag      60
```

-continued

```
aaggcggcgg cggaggagag gccgagttac cgcccgccgc ccgcgccccc ccaaccccgc    120
cgccgccgcc gccgccgcca ctgccccccc tccccgcggc gccgcatctt gaatggaaac    180
atggcggtgc cggctcggac ctgcggcgcc tctcggcccg gcccagcgcg gactgcgcgc    240
ccctggcccg gctgcggccc ccaccctggc cccggcaccc ggcgcccgac gtccgggccc    300
ccgcgcccgc tgtggctgct gctgccgctt ctaccgctgc tcgccgcccc cggcgcctct    360
gcctacagct tcccccagca gcacacgatg cagcactggg cccggcgtct ggagcaggag    420
gtcgacggcg tgatgcggat ttttggaggc gtccagcagc tccgtgagat ttacaaggac    480
aaccggaacc tgttcgaggt acaggagaat gagcctcaga agttggtgga gaaggtggca    540
ggggacattg agagccttct ggacaggaag gtgcaggccc tgaagagact ggctgatgct    600
gcagagaact tccagaaagc acaccgctgg caggacaaca tcaaggagga agacatcgtg    660
tactatgacg ccaaggctga cgctgagctg gacgaccctg agagtgagga tgtggaaagg    720
gggtctaagg ccagcaccct aaggctggac ttcatcgagg acccaaactt caagaacaag    780
gtcaactatt catacgcggc tgtacagatc cctacggaca tctacaaagg ctccactgtc    840
atcctcaatg agctcaactg gacagaggcc ctggagaatg tgttcatgga aaaccgcaga    900
caagacccca cactgctgtg gcaggtcttc ggcagcgcca caggagtcac tcgctactac    960
ccggccaccc cgtggcgagc ccccaagaag atcgacctgt acgatgtccg aaggagaccc   1020
tggtatatcc agggggcctc gtcacccaaa gacatggtca tcatcgtgga tgtgagtggc   1080
agtgtgagcg gcctgaccct gaagctgatg aagacatctg tctgcgagat gctggacacg   1140
ctgtctgatg atgactatgt gaatgtggcc tcgttcaacg agaaggcaca gcctgtgtca   1200
tgcttcacac acctggtgca ggccaatgtg cgcaacaaga aggtgttcaa ggaagctgtg   1260
cagggcatgg tggccaaggg caccacaggc tacaaggccg gctttgagta tgcctttgac   1320
cagctgcaga actccaacat cactcgggcc aactgcaaca agatgatcat gatgttcacg   1380
gatggtggtg aggaccgcgt gcaggacgtc tttgagaagt acaattggcc aaaccggacg   1440
gtgcgcgtgt ttactttctc cgtggggcag cataactatg acgtcacacc gctgcagtgg   1500
atggcctgtg ccaacaaagg ctactatttt gagatccctt ccatcggagc catccgcatc   1560
aacacacagg aatatctaga tgtgttgggc aggcccatgg tgctggcagg caaggaggcc   1620
aagcaggttc agtggaccaa cgtgtatgag gatgcactgg gactggggtt ggtggtaaca   1680
gggaccctcc ctgttttcaa cctgacacag gatggccctg ggaaaaagaa gaaccagctg   1740
atcctgggcg tgatgggcat tgacgtggct ctgaatgaca tcaagaggct gacccccaac   1800
tacacgcttg gagccaacgg ctatgtgttt gccattgacc tgaacggcta cgtgttgctg   1860
caccccaatc tcaagcccca gaccaccaac ttccgggagc ctgtgactct ggacttcctg   1920
gatgcggagc tagaggatga gaacaaggaa gagatccgtc ggagcatgat tgatggcaac   1980
aagggccaca agcagatcag aacgttggtc aagtccctgg atgagaggta catagatgag   2040
gtgacacgga actacacctg ggtgcctata aggagcacta actacagcct ggggctggtg   2100
ctcccaccct acagcacctt ctacctccaa gccaatctca gtgaccagat cctgcaggtc   2160
aagtattttg agttcctgct ccccagcagc tttgagtctg aaggacacgt tttcattgct   2220
cccagagagt actgcaagga cctgaatgcc tcagacaaca acaccgagtt cctgaaaaac   2280
tttattgagc tcatggagaa agtgactcca gactccaagc agtgcaacaa cttccttctg   2340
cacaacctga tcttggacac gggcatcacg cagcagctgg tagagcgtgt gtggagggac   2400
```

-continued

```
caggatctca acacgtacag cctactggcc gtgttcgctg ccacagacgg tggcatcacc   2460
cgagtcttcc ccaacaaggc agctgaggac tggacagaga accctgagcc cttcaatgcc   2520
agcttctacc gccgcagcct ggataaccac ggttatgtct tcaagccccc acaccaggat   2580
gccctgttaa ggccgctgga gctggagaat gacactgtgg gcatcctcgt cagcacagct   2640
gtggagctca gcctaggcag gcgcacactg aggccagcag tggtgggcgt caagctggac   2700
ctagaggctt gggctgagaa gttcaaggtg ctagccagca accgtaccca ccaagaccag   2760
cctcagaagt gcggccccaa cagccactgt gagatggact gcgaggttaa caatgaggac   2820
ttactctgtg tcctcattga tgatggagga ttcctggtgc tgtcaaacca gaaccatcag   2880
tgggaccagg tgggcaggtt cttcagtgag gtggatgcca acctgatgct ggcactctac   2940
aataactcct tctacacccg caaggagtcc tatgactatc aggcagcctg tgcccctcag   3000
cccccctggca acctgggtgc tgcaccccgg ggtgtctttg tgcccaccgt tgcagatttc   3060
cttaacctgg cctggtggac ctctgctgcc gcctggtccc tgttccagca gcttctctac   3120
ggcctcatct accacagctg gttccaagca gaccccgcgg aggccgaggg gagccccgag   3180
acgcgcgaga gcagctgcgt catgaaacag acccagtact acttcggctc ggtaaacgcc   3240
tcctacaacg ccatcatcga ctgcggaaac tgctccaggc tgttccacgc gcagagactg   3300
accaacacca atcttctctt tgtggtggcc gagaagccgc tgtgcagcca gtgcgaggct   3360
ggccggctgc tgcagaagga gacgcactgc ccagcggacg gcccggagca gtgtgagcta   3420
gtgcagagac cgcgataccg gagaggcccg cacatctgct tcgactacaa cgcgacagaa   3480
gatacctcag actgtggccg cggggcctcc ttcccgccgt cgctgggcgt cctggtctcc   3540
ctgcaactgc tgctcctcct gggcctgccg ccccggccgc agcctcaagt cctcgtccac   3600
gcctctcgcc gcctctgagc accctgcccc accccacctc cactcccacc tcacccggcc   3660
tcttcgcctt tcccaccctc ctgccccaca ctccccgcct tagagcctcg tccctccctc   3720
actgaaggac ctgagctggc caggccctga gagtctggtc tgcgccttgg gatggggagt   3780
cccaaagcgg gacgccgcag gtgtttggca cccaaatcac atctcacctc cgaactgttc   3840
aagtgtcccc agacccttct tgcctgctgg gctcccccca gtgggatggg acagggaggc   3900
cacacgcact ggtgccaaaa ccaggcctct gctgccgccc ttcctggagg ctgcctatgt   3960
tggggggac cctgcctcag ctgacccggc ctctctgccc cacccaagcc caaacttggt   4020
ttctgtgaga atagtggagg aaggtgagat ggccagtttg aagcctgtgc ctcccagctt   4080
aaatcctagc aggagagagg ctctggggca gcccccatgg gctcctgccc ctttcaggcc   4140
tacagccaca tccccaagcc caccaggtgt caggatagtc acagtgatac cagttcagac   4200
actaccccat atacacctgg aacattgagg atggaaactg gactcacatt cgacataccc   4260
cactgggcac acgcacaaac acacacacta tggggtgggg tgggtgtagg ggcttacaaa   4320
gccttacaca gggcgagggg ttggtgggag ggttggcacc tgcacactcc atctcctgct   4380
caccacctgc ctctaatctg agctgcagcc tggctggtcc tcccatttct aaagctgaat   4440
gtcaaacagt gccaaatgct ggggcagggg gtgaagaacc ctctgtccca cccctagcca   4500
ccagtgtcct ccaagtgccc cctcacctct ccaggtgctc attgtaacca tttctcacta   4560
gtgtcaggcc cccagtggga ccacatgcca ctgcctgcac ctttcggcag aggaaccccc   4620
accagacatc accctttgcc ttagcagggg tgactttgtc tctcctggct gggccatcct   4680
tccgccaatc tggcccttac acactcaggc ctgtgcccac tccctatctc cttcccaccc   4740
ctacacacac actccctgct tgcaggaggc caaactgtcc ctcccttgct gaacacacac   4800
```

```
acacacacac acacacaggt ggggactggg cacagctctt cacaccattc attctggtca   4860

tttcccccaa aggcatccca gcctgggggc cagtggggaa ctgagggcaa ggggatatag   4920

tgatggggct cagatggact gggaggaggg ggagggtgat gcattaatta atggcttcgt   4980

taattaatgt catgttgctt gtcgctttct cagtgtgtgt gtgtggtcca tgcccactgc   5040

tggtgccagg gtgggtgtcc atgtgcaccc ggcctggatg ccagctgtgt ccttcggggg   5100

cgtgcgtgta actgtagtgt agtcaggtgc tcaatggaga atataaacat atacagaaaa   5160

atatatattt taagtttaaa aaacagaaaa acagacaaaa caatccccat caggtagctg   5220

tctaaccccc agctgggtct aatccttctc attacccacc cgacctggct gcccctcacc   5280

ttgggctggg ggactggggg gccatttcct tttctctgcc ctttttttgt tgttctattt   5340

tgtacagaca agttggaaaa acaacagcga caaaaaagtc aagaaacttt gtaaaatatc   5400

gtgtgtgtga ttccttgtaa aatattttca aatggtttat tacagaagat cagttattaa   5460

ataatgttca tattttcact tc                                             5482
```

```
<210> SEQ ID NO 20
<211> LENGTH: 1145
<212> TYPE: PRT
<213> ORGANISM: Homo sapiens

<400> SEQUENCE: 20

Met Ala Val Pro Ala Arg Thr Cys Gly Ala Ser Arg Pro Gly Pro Ala
  1               5                  10                  15

Arg Thr Ala Arg Pro Trp Pro Gly Cys Gly Pro His Pro Gly Pro Gly
             20                  25                  30

Thr Arg Arg Pro Thr Ser Gly Pro Pro Arg Pro Leu Trp Leu Leu Leu
         35                  40                  45

Pro Leu Leu Pro Leu Leu Ala Ala Pro Gly Ala Ser Ala Tyr Ser Phe
     50                  55                  60

Pro Gln Gln His Thr Met Gln His Trp Ala Arg Arg Leu Glu Gln Glu
 65                  70                  75                  80

Val Asp Gly Val Met Arg Ile Phe Gly Gly Val Gln Gln Leu Arg Glu
                 85                  90                  95

Ile Tyr Lys Asp Asn Arg Asn Leu Phe Glu Val Gln Glu Asn Glu Pro
            100                 105                 110

Gln Lys Leu Val Glu Lys Val Ala Gly Asp Ile Glu Ser Leu Leu Asp
        115                 120                 125

Arg Lys Val Gln Ala Leu Lys Arg Leu Ala Asp Ala Ala Glu Asn Phe
    130                 135                 140

Gln Lys Ala His Arg Trp Gln Asp Asn Ile Lys Glu Glu Asp Ile Val
145                 150                 155                 160

Tyr Tyr Asp Ala Lys Ala Asp Ala Glu Leu Asp Asp Pro Glu Ser Glu
                165                 170                 175

Asp Val Glu Arg Gly Ser Lys Ala Ser Thr Leu Arg Leu Asp Phe Ile
            180                 185                 190

Glu Asp Pro Asn Phe Lys Asn Lys Val Asn Tyr Ser Tyr Ala Ala Val
        195                 200                 205

Gln Ile Pro Thr Asp Ile Tyr Lys Gly Ser Thr Val Ile Leu Asn Glu
    210                 215                 220

Leu Asn Trp Thr Glu Ala Leu Glu Asn Val Phe Met Glu Asn Arg Arg
225                 230                 235                 240

Gln Asp Pro Thr Leu Leu Trp Gln Val Phe Gly Ser Ala Thr Gly Val
```

-continued

```
            245                 250                 255

Thr Arg Tyr Tyr Pro Ala Thr Pro Trp Arg Ala Pro Lys Lys Ile Asp
            260                 265                 270

Leu Tyr Asp Val Arg Arg Arg Pro Trp Tyr Ile Gln Gly Ala Ser Ser
        275                 280                 285

Pro Lys Asp Met Val Ile Ile Val Asp Val Ser Gly Ser Val Ser Gly
    290                 295                 300

Leu Thr Leu Lys Leu Met Lys Thr Ser Val Cys Glu Met Leu Asp Thr
305                 310                 315                 320

Leu Ser Asp Asp Asp Tyr Val Asn Val Ala Ser Phe Asn Glu Lys Ala
                325                 330                 335

Gln Pro Val Ser Cys Phe Thr His Leu Val Gln Ala Asn Val Arg Asn
            340                 345                 350

Lys Lys Val Phe Lys Glu Ala Val Gln Gly Met Val Ala Lys Gly Thr
        355                 360                 365

Thr Gly Tyr Lys Ala Gly Phe Glu Tyr Ala Phe Asp Gln Leu Gln Asn
    370                 375                 380

Ser Asn Ile Thr Arg Ala Asn Cys Asn Lys Met Ile Met Met Phe Thr
385                 390                 395                 400

Asp Gly Gly Glu Asp Arg Val Gln Asp Val Phe Glu Lys Tyr Asn Trp
                405                 410                 415

Pro Asn Arg Thr Val Arg Val Phe Thr Phe Ser Val Gly Gln His Asn
            420                 425                 430

Tyr Asp Val Thr Pro Leu Gln Trp Met Ala Cys Ala Asn Lys Gly Tyr
        435                 440                 445

Tyr Phe Glu Ile Pro Ser Ile Gly Ala Ile Arg Ile Asn Thr Gln Glu
    450                 455                 460

Tyr Leu Asp Val Leu Gly Arg Pro Met Val Leu Ala Gly Lys Glu Ala
465                 470                 475                 480

Lys Gln Val Gln Trp Thr Asn Val Tyr Glu Asp Ala Leu Gly Leu Gly
                485                 490                 495

Leu Val Val Thr Gly Thr Leu Pro Val Phe Asn Leu Thr Gln Asp Gly
            500                 505                 510

Pro Gly Glu Lys Lys Asn Gln Leu Ile Leu Gly Val Met Gly Ile Asp
        515                 520                 525

Val Ala Leu Asn Asp Ile Lys Arg Leu Thr Pro Asn Tyr Thr Leu Gly
    530                 535                 540

Ala Asn Gly Tyr Val Phe Ala Ile Asp Leu Asn Gly Tyr Val Leu Leu
545                 550                 555                 560

His Pro Asn Leu Lys Pro Gln Thr Thr Asn Phe Arg Glu Pro Val Thr
                565                 570                 575

Leu Asp Phe Leu Asp Ala Glu Leu Glu Asp Glu Asn Lys Glu Glu Ile
            580                 585                 590

Arg Arg Ser Met Ile Asp Gly Asn Lys Gly His Lys Gln Ile Arg Thr
        595                 600                 605

Leu Val Lys Ser Leu Asp Glu Arg Tyr Ile Asp Glu Val Thr Arg Asn
    610                 615                 620

Tyr Thr Trp Val Pro Ile Arg Ser Thr Asn Tyr Ser Leu Gly Leu Val
625                 630                 635                 640

Leu Pro Pro Tyr Ser Thr Phe Tyr Leu Gln Ala Asn Leu Ser Asp Gln
                645                 650                 655

Ile Leu Gln Val Lys Tyr Phe Glu Phe Leu Leu Pro Ser Ser Phe Glu
            660                 665                 670
```

-continued

```
Ser Glu Gly His Val Phe Ile Ala Pro Arg Glu Tyr Cys Lys Asp Leu
        675                 680                 685

Asn Ala Ser Asp Asn Asn Thr Glu Phe Leu Lys Asn Phe Ile Glu Leu
    690                 695                 700

Met Glu Lys Val Thr Pro Asp Ser Lys Gln Cys Asn Asn Phe Leu Leu
705                 710                 715                 720

His Asn Leu Ile Leu Asp Thr Gly Ile Thr Gln Gln Leu Val Glu Arg
                725                 730                 735

Val Trp Arg Asp Gln Asp Leu Asn Thr Tyr Ser Leu Leu Ala Val Phe
            740                 745                 750

Ala Ala Thr Asp Gly Gly Ile Thr Arg Val Phe Pro Asn Lys Ala Ala
        755                 760                 765

Glu Asp Trp Thr Glu Asn Pro Glu Pro Phe Asn Ala Ser Phe Tyr Arg
    770                 775                 780

Arg Ser Leu Asp Asn His Gly Tyr Val Phe Lys Pro Pro His Gln Asp
785                 790                 795                 800

Ala Leu Leu Arg Pro Leu Glu Leu Glu Asn Asp Thr Val Gly Ile Leu
                805                 810                 815

Val Ser Thr Ala Val Glu Leu Ser Leu Gly Arg Arg Thr Leu Arg Pro
            820                 825                 830

Ala Val Val Gly Val Lys Leu Asp Leu Glu Ala Trp Ala Glu Lys Phe
        835                 840                 845

Lys Val Leu Ala Ser Asn Arg Thr His Gln Asp Gln Pro Gln Lys Cys
    850                 855                 860

Gly Pro Asn Ser His Cys Glu Met Asp Cys Glu Val Asn Asn Glu Asp
865                 870                 875                 880

Leu Leu Cys Val Leu Ile Asp Asp Gly Gly Phe Leu Val Leu Ser Asn
                885                 890                 895

Gln Asn His Gln Trp Asp Gln Val Gly Arg Phe Phe Ser Glu Val Asp
            900                 905                 910

Ala Asn Leu Met Leu Ala Leu Tyr Asn Asn Ser Phe Tyr Thr Arg Lys
        915                 920                 925

Glu Ser Tyr Asp Tyr Gln Ala Ala Cys Ala Pro Gln Pro Pro Gly Asn
    930                 935                 940

Leu Gly Ala Ala Pro Arg Gly Val Phe Val Pro Thr Val Ala Asp Phe
945                 950                 955                 960

Leu Asn Leu Ala Trp Trp Thr Ser Ala Ala Ala Trp Ser Leu Phe Gln
                965                 970                 975

Gln Leu Leu Tyr Gly Leu Ile Tyr His Ser Trp Phe Gln Ala Asp Pro
            980                 985                 990

Ala Glu Ala Glu Gly Ser Pro Glu Thr Arg Glu Ser Ser Cys Val Met
        995                 1000                1005

Lys Gln Thr Gln Tyr Tyr Phe Gly Ser Val Asn Ala Ser Tyr Asn Ala
   1010                1015                1020

Ile Ile Asp Cys Gly Asn Cys Ser Arg Leu Phe His Ala Gln Arg Leu
1025               1030                1035                1040

Thr Asn Thr Asn Leu Leu Phe Val Val Ala Glu Lys Pro Leu Cys Ser
               1045                1050                1055

Gln Cys Glu Ala Gly Arg Leu Leu Gln Lys Glu Thr His Cys Pro Ala
           1060                1065                1070

Asp Gly Pro Glu Gln Cys Glu Leu Val Gln Arg Pro Arg Tyr Arg Arg
       1075                1080                1085
```

-continued

```
Gly Pro His Ile Cys Phe Asp Tyr Asn Ala Thr Glu Asp Thr Ser Asp
   1090                1095                1100

Cys Gly Arg Gly Ala Ser Phe Pro Pro Ser Leu Gly Val Leu Val Ser
1105               1110                1115                1120

Leu Gln Leu Leu Leu Leu Leu Gly Leu Pro Pro Arg Pro Gln Pro Gln
               1125                1130                1135

Val Leu Val His Ala Ser Arg Arg Leu
           1140                1145


<210> SEQ ID NO 21
<211> LENGTH: 3770
<212> TYPE: DNA
<213> ORGANISM: Homo sapiens

<400> SEQUENCE: 21

tactataggg cggccgcgaa ttcggcacga ggcggcgcgg agcggagcag gcagccccgc     60

gcgctcgccc accgcccgct ccgcgcagct ccccgcggcc gctctcgtcg ccgccgcagc    120

gggcgcgtcg gagggagccc agcatggccg ggccgggctc gccgcgccgc gcgtcccggg    180

gggcctcggc gcttctcgct gccgcgcttc tctacgccgc gctgggggac gtggtgcgct    240

cggagcagca gataccgctc tccgtggtga agctctgggc ctcggctttt ggtggggaga    300

taaaatccat tgctgctaag tactccggtt cccagcttct gcaaaagaaa tacaaagagt    360

atgagaaaga cgttgccata gaagaaattg atggcctcca actggtaaag aagctggcaa    420

agaacatgga agagatgttt cacaagaagt ctgaggccgt caggcgtctg gtggaggctg    480

cagaagaagc acacctgaaa catgaatttg atgcagactt acagtatgaa tacttcaatg    540

ctgtgctgat aaatgaaagg gacaaagacg ggaatttttt ggagctggga aaggaattca    600

tcttagcccc aaatgaccat tttaataatt tgcctgtgaa catcagtcta agtgacgtcc    660

aagtaccaac gaacatgtac aacaaagacc ctgcaattgt caatggggtt tattggtctg    720

aatctctaaa caaagttttt gtagataact ttgaccgtga cccatctctc atatggcagt    780

actttggaag tgcaaagggc ttttttaggc agtatccggg gattaaatgg gaaccagatg    840

agaatggagt cattgccttc gactgcagga accgaaaatg gtacatccag gcagcaactt    900

ctccgaaaga cgtggtcatt ttagttgacg tcagtggcag catgaaagga ctccgtctga    960

ctatcgcgaa gcaaacagtc tcatccattt tggatacact tggggatgat gacttcttca   1020

acataattgc ttataatgag gagcttcact atgtggaacc ttgcctgaat ggaactttgg   1080

tgcaagccga caggacaaac aaagagcact tcagggagca tctggacaaa cttttcgcca   1140

aaggaattgg aatgttggat atagctctga atgaggcctt caacattctg agtgatttca   1200

accacacggg acaaggaagt atctgcagtc aggccatcat gctcataact gatggggcgg   1260

tggacaccta tgatacaatc tttgcaaaat acaattggcc agatcgaaag gttcgcatct   1320

tcacatacct cattggacga gaggctgcgt ttgcagacaa tctaaagtgg atggcctgtg   1380

ccaacaaagg atttttttacc cagatctcca ccttggctga tgtgcaggag aatgtcatgg   1440

aataccttca cgtgcttagc cggcccaaag tcatcgacca ggagcatgat gtggtgtgga   1500

ccgaagctta cattgacagc actctgactg atgatcaggg ccccgtcctg atgaccactg   1560

tagccatgcc tgtgtttagt aagcagaacg aaaccagatc gaagggcatt cttctgggag   1620

tggttggcac agatgtccca gtgaaagaac ttctgaagac catcccccaaa tacaagttag   1680

ggattcacgg ttatgccttt gcaatcacaa ataatggrta tatcctgacg catccggaac   1740

tcaggctgct gtacgaagaa ggaaaaaagc gaaggaaacc taactatagt agcgttgacc   1800
```

-continued

```
tctctgaggt ggagtgggaa gaccgagatg acgtgttgag aaatgctatg gtgaatcgaa   1860
agacggggaa gttttccatg gaggtgaaga agacagtgga caaagggaaa cgggttttgg   1920
tgatgacaaa tgactactat tatacagaca tcaagggtac tcctttcagt ttaggtgtgg   1980
cgctttccag aggtcatggg aaatatttct tccgagggaa tgtaaccatc gaagaaggcc   2040
tgcatgactt agaacatccc gatgtgtcct tggcagatga atggtcctac tgcaacactg   2100
acctacaccc tgagcaccgc catctgtctc agttagaagc gattaagctc tacctaaaag   2160
gcaaagaacc tctgctccag tgtgataaag aattgatcca agaagtcctt tttgacgcgg   2220
tggtgagtgc ccccattgaa gcgtattgga ccagcctggc cctcaacaaa tctgaaaatt   2280
ctgacaaggg cgtggaggtt gccttcctcg gcactcgcac gggcctctcc agaatcaacc   2340
tgtttgtcgg ggctgagcag ctcaccaatc aggacttcct gaaagctggc gacaaggaga   2400
acatttttaa cgcagaccat ttccctctct ggtaccgaag agccgctgag cagattccag   2460
ggagcttcgt ctactcgatc ccattcagca ctggaccagt caataaaagc aatgtggtga   2520
cagcaagtac atccatccag ctcctggatg aacggaaatc tcctgtggtg gcagctgtag   2580
gcattcagat gaaacttgaa tttttccaaa ggaagttctg gactgccagc agacagtgtg   2640
cttccctgga tggcaaatgc tccatcagct gtgatgatga gactgtgaat tgttacctca   2700
tagacaataa tggatttatt ttggtgtctg aagactacac acagactgga gactttttttg   2760
gtgagatcga gggagctgtg atgaacaaat tgctaacaat gggctccttt aaaagaatta   2820
ccctttatga ctaccaagcc atgtgtagag ccaacaagga aagcagcgat ggcgcccatg   2880
gcctcctgga tccttataat gccttcctct ctgcagtaaa atggatcatg acagaacttg   2940
tcttgttcct ggtggaattt aacctctgca gttggtggca ctccgatatg acagctaaag   3000
cccagaaatt gaaacagacc ctggagcctt gtgatactga atatccagca ttcgtctctg   3060
agcgcaccat caaggagact acagggaata ttgcttgtga agactgctcc aagtcctttg   3120
tcatccagca aatcccaagc agcaacctgt tcatggtggt ggtggacagc agctgcctct   3180
gtgaatctgt ggcccccatc accatggcac ccattgaaat caggtataat gaatccctta   3240
agtgtgaacg tctaaaggcc cagaagatca gaaggcgccc agaatcttgt catggcttcc   3300
atcctgagga gaatgcaagg gagtgtgggg gtgcgccgag tctccaagcc cagacagtcc   3360
tccttctgct ccctctgctt ttgatgctct tctcaaggtg acactgactg agatgttctc   3420
ttactgactg agatgttctc ttggcatgct aaatcatgga taaactgtga accaaaatat   3480
ggtgcaacat acgagacatg aatatagtcc aaccatcagc atctcatcat gattttaaac   3540
tgtgcgtgat ataaactctt aaagatatgt tgacaaaaag ttatctatca tctttttact   3600
ttgccagtca tgcaaatgtg agtttgccac atgataatca cccttcatca gaaatgggac   3660
cgcaagtggt aggcagtgtc ccttctgctt gaaacctatt gaaaccaatt taaaactgtg   3720
tactttttaa ataaagtata ttaaaatcat aaaaaaaaaa aaaaaaaaa              3770
```

<210> SEQ ID NO 22
<211> LENGTH: 1085
<212> TYPE: PRT
<213> ORGANISM: Homo sapiens

<400> SEQUENCE: 22

```
Met Ala Gly Pro Gly Ser Pro Arg Arg Ala Ser Arg Gly Ala Ser Ala
  1               5                  10                  15

Leu Leu Ala Ala Ala Leu Leu Tyr Ala Ala Leu Gly Asp Val Val Arg
```

-continued

```
            20                  25                  30

Ser Glu Gln Gln Ile Pro Leu Ser Val Val Lys Leu Trp Ala Ser Ala
        35                  40                  45

Phe Gly Gly Glu Ile Lys Ser Ile Ala Ala Lys Tyr Ser Gly Ser Gln
    50                  55                  60

Leu Leu Gln Lys Lys Tyr Lys Glu Tyr Glu Lys Asp Val Ala Ile Glu
 65                  70                  75                  80

Glu Ile Asp Gly Leu Gln Leu Val Lys Lys Leu Ala Lys Asn Met Glu
                85                  90                  95

Glu Met Phe His Lys Lys Ser Glu Ala Val Arg Arg Leu Val Glu Ala
            100                 105                 110

Ala Glu Glu Ala His Leu Lys His Glu Phe Asp Ala Asp Leu Gln Tyr
        115                 120                 125

Glu Tyr Phe Asn Ala Val Leu Ile Asn Glu Arg Asp Lys Asp Gly Asn
    130                 135                 140

Phe Leu Glu Leu Gly Lys Glu Phe Ile Leu Ala Pro Asn Asp His Phe
145                 150                 155                 160

Asn Asn Leu Pro Val Asn Ile Ser Leu Ser Asp Val Gln Val Pro Thr
                165                 170                 175

Asn Met Tyr Asn Lys Asp Pro Ala Ile Val Asn Gly Val Tyr Trp Ser
            180                 185                 190

Glu Ser Leu Asn Lys Val Phe Val Asp Asn Phe Asp Arg Asp Pro Ser
        195                 200                 205

Leu Ile Trp Gln Tyr Phe Gly Ser Ala Lys Gly Phe Phe Arg Gln Tyr
    210                 215                 220

Pro Gly Ile Lys Trp Glu Pro Asp Glu Asn Gly Val Ile Ala Phe Asp
225                 230                 235                 240

Cys Arg Asn Arg Lys Trp Tyr Ile Gln Ala Ala Thr Ser Pro Lys Asp
                245                 250                 255

Val Val Ile Leu Val Asp Val Ser Gly Ser Met Lys Gly Leu Arg Leu
            260                 265                 270

Thr Ile Ala Lys Gln Thr Val Ser Ser Ile Leu Asp Thr Leu Gly Asp
        275                 280                 285

Asp Asp Phe Phe Asn Ile Ile Ala Tyr Asn Glu Glu Leu His Tyr Val
    290                 295                 300

Glu Pro Cys Leu Asn Gly Thr Leu Val Gln Ala Asp Arg Thr Asn Lys
305                 310                 315                 320

Glu His Phe Arg Glu His Leu Asp Lys Leu Phe Ala Lys Gly Ile Gly
                325                 330                 335

Met Leu Asp Ile Ala Leu Asn Glu Ala Phe Asn Ile Leu Ser Asp Phe
            340                 345                 350

Asn His Thr Gly Gln Gly Ser Ile Cys Ser Gln Ala Ile Met Leu Ile
        355                 360                 365

Thr Asp Gly Ala Val Asp Thr Tyr Asp Thr Ile Phe Ala Lys Tyr Asn
    370                 375                 380

Trp Pro Asp Arg Lys Val Arg Ile Phe Thr Tyr Leu Ile Gly Arg Glu
385                 390                 395                 400

Ala Ala Phe Ala Asp Asn Leu Lys Trp Met Ala Cys Ala Asn Lys Gly
                405                 410                 415

Phe Phe Thr Gln Ile Ser Thr Leu Ala Asp Val Gln Glu Asn Val Met
            420                 425                 430

Glu Tyr Leu His Val Leu Ser Arg Pro Lys Val Ile Asp Gln Glu His
        435                 440                 445
```

-continued

```
Asp Val Val Trp Thr Glu Ala Tyr Ile Asp Ser Thr Leu Thr Asp Asp
    450                 455                 460

Gln Gly Pro Val Leu Met Thr Thr Val Ala Met Pro Val Phe Ser Lys
465                 470                 475                 480

Gln Asn Glu Thr Arg Ser Lys Gly Ile Leu Leu Gly Val Val Gly Thr
                485                 490                 495

Asp Val Pro Val Lys Glu Leu Leu Lys Thr Ile Pro Lys Tyr Lys Leu
            500                 505                 510

Gly Ile His Gly Tyr Ala Phe Ala Ile Thr Asn Asn Gly Tyr Ile Leu
        515                 520                 525

Thr His Pro Glu Leu Arg Leu Leu Tyr Glu Glu Gly Lys Lys Arg Arg
    530                 535                 540

Lys Pro Asn Tyr Ser Ser Val Asp Leu Ser Glu Val Glu Trp Glu Asp
545                 550                 555                 560

Arg Asp Asp Val Leu Arg Asn Ala Met Val Asn Arg Lys Thr Gly Lys
                565                 570                 575

Phe Ser Met Glu Val Lys Lys Thr Val Asp Lys Gly Lys Arg Val Leu
            580                 585                 590

Val Met Thr Asn Asp Tyr Tyr Tyr Thr Asp Ile Lys Gly Thr Pro Phe
        595                 600                 605

Ser Leu Gly Val Ala Leu Ser Arg Gly His Gly Lys Tyr Phe Phe Arg
    610                 615                 620

Gly Asn Val Thr Ile Glu Glu Gly Leu His Asp Leu Glu His Pro Asp
625                 630                 635                 640

Val Ser Leu Ala Asp Glu Trp Ser Tyr Cys Asn Thr Asp Leu His Pro
                645                 650                 655

Glu His Arg His Leu Ser Gln Leu Glu Ala Ile Lys Leu Tyr Leu Lys
            660                 665                 670

Gly Lys Glu Pro Leu Leu Gln Cys Asp Lys Glu Leu Ile Gln Glu Val
        675                 680                 685

Leu Phe Asp Ala Val Val Ser Ala Pro Ile Glu Ala Tyr Trp Thr Ser
    690                 695                 700

Leu Ala Leu Asn Lys Ser Glu Asn Ser Asp Lys Gly Val Glu Val Ala
705                 710                 715                 720

Phe Leu Gly Thr Arg Thr Gly Leu Ser Arg Ile Asn Leu Phe Val Gly
                725                 730                 735

Ala Glu Gln Leu Thr Asn Gln Asp Phe Leu Lys Ala Gly Asp Lys Glu
            740                 745                 750

Asn Ile Phe Asn Ala Asp His Phe Pro Leu Trp Tyr Arg Arg Ala Ala
        755                 760                 765

Glu Gln Ile Pro Gly Ser Phe Val Tyr Ser Ile Pro Phe Ser Thr Gly
    770                 775                 780

Pro Val Asn Lys Ser Asn Val Val Thr Ala Ser Thr Ser Ile Gln Leu
785                 790                 795                 800

Leu Asp Glu Arg Lys Ser Pro Val Val Ala Ala Val Gly Ile Gln Met
                805                 810                 815

Lys Leu Glu Phe Phe Gln Arg Lys Phe Trp Thr Ala Ser Arg Gln Cys
            820                 825                 830

Ala Ser Leu Asp Gly Lys Cys Ser Ile Ser Cys Asp Asp Glu Thr Val
        835                 840                 845

Asn Cys Tyr Leu Ile Asp Asn Asn Gly Phe Ile Leu Val Ser Glu Asp
    850                 855                 860
```

-continued

```
Tyr Thr Gln Thr Gly Asp Phe Phe Gly Glu Ile Glu Gly Ala Val Met
865                 870                 875                 880

Asn Lys Leu Leu Thr Met Gly Ser Phe Lys Arg Ile Thr Leu Tyr Asp
                885                 890                 895

Tyr Gln Ala Met Cys Arg Ala Asn Lys Glu Ser Ser Asp Gly Ala His
            900                 905                 910

Gly Leu Leu Asp Pro Tyr Asn Ala Phe Leu Ser Ala Val Lys Trp Ile
        915                 920                 925

Met Thr Glu Leu Val Leu Phe Leu Val Glu Phe Asn Leu Cys Ser Trp
    930                 935                 940

Trp His Ser Asp Met Thr Ala Lys Ala Gln Lys Leu Lys Gln Thr Leu
945                 950                 955                 960

Glu Pro Cys Asp Thr Glu Tyr Pro Ala Phe Val Ser Glu Arg Thr Ile
                965                 970                 975

Lys Glu Thr Thr Gly Asn Ile Ala Cys Glu Asp Cys Ser Lys Ser Phe
            980                 985                 990

Val Ile Gln Gln Ile Pro Ser Ser Asn Leu Phe Met Val Val Val Asp
        995                 1000                1005

Ser Ser Cys Leu Cys Glu Ser Val Ala Pro Ile Thr Met Ala Pro Ile
   1010                1015                1020

Glu Ile Arg Tyr Asn Glu Ser Leu Lys Cys Glu Arg Leu Lys Ala Gln
1025                1030                1035                1040

Lys Ile Arg Arg Arg Pro Glu Ser Cys His Gly Phe His Pro Glu Glu
               1045                1050                1055

Asn Ala Arg Glu Cys Gly Gly Ala Pro Ser Leu Gln Ala Gln Thr Val
           1060                1065                1070

Leu Leu Leu Leu Pro Leu Leu Leu Met Leu Phe Ser Arg
       1075                1080                1085


<210> SEQ ID NO 23
<211> LENGTH: 1115
<212> TYPE: PRT
<213> ORGANISM: Homo sapiens

<400> SEQUENCE: 23

Met Ala Val Pro Ala Arg Thr Cys Gly Ala Ser Arg Pro Gly Pro Ala
  1               5                  10                  15

Arg Thr Ala Arg Pro Trp Pro Gly Cys Gly Pro His Pro Gly Pro Gly
             20                  25                  30

Thr Arg Arg Pro Thr Ser Gly Pro Pro Arg Pro Leu Trp Leu Leu Leu
         35                  40                  45

Pro Leu Leu Pro Leu Leu Ala Ala Pro Gly Ala Ser Ala Tyr Ser Phe
     50                  55                  60

Pro Gln Gln His Thr Met Gln His Trp Ala Arg Arg Leu Glu Gln Glu
 65                  70                  75                  80

Val Asp Gly Val Met Arg Ile Phe Gly Gly Val Gln Gln Leu Arg Glu
                 85                  90                  95

Ile Tyr Lys Asp Asn Arg Asn Leu Phe Glu Val Gln Glu Asn Glu Pro
            100                 105                 110

Gln Lys Leu Val Glu Lys Val Ala Gly Asp Ile Glu Ser Leu Leu Asp
        115                 120                 125

Arg Lys Val Gln Ala Leu Lys Arg Leu Ala Asp Ala Ala Glu Asn Phe
    130                 135                 140

Gln Lys Ala His Arg Trp Gln Asp Asn Ile Lys Glu Glu Asp Ile Val
145                 150                 155                 160
```

-continued

```
Tyr Tyr Asp Ala Lys Ala Asp Ala Glu Leu Asp Asp Pro Glu Ser Glu
                165                 170                 175

Asp Val Glu Arg Gly Ser Lys Ala Ser Thr Leu Arg Leu Asp Phe Ile
            180                 185                 190

Glu Asp Pro Asn Phe Lys Asn Lys Val Asn Tyr Ser Tyr Ala Ala Val
        195                 200                 205

Gln Ile Pro Thr Asp Ile Tyr Lys Gly Ser Thr Val Ile Leu Asn Glu
    210                 215                 220

Leu Asn Trp Thr Glu Ala Leu Glu Asn Val Phe Met Glu Asn Arg Arg
225                 230                 235                 240

Gln Asp Pro Thr Leu Leu Trp Gln Val Phe Gly Ser Ala Thr Gly Val
                245                 250                 255

Thr Arg Tyr Tyr Pro Ala Thr Pro Trp Arg Ala Pro Lys Lys Ile Asp
            260                 265                 270

Leu Tyr Asp Val Arg Arg Arg Pro Trp Tyr Ile Gln Gly Ala Ser Ser
        275                 280                 285

Pro Lys Asp Met Val Ile Ile Val Asp Val Ser Gly Ser Val Ser Gly
    290                 295                 300

Leu Thr Leu Lys Leu Met Lys Thr Ser Val Cys Glu Met Leu Asp Thr
305                 310                 315                 320

Leu Ser Asp Asp Asp Tyr Val Asn Val Ala Ser Phe Asn Glu Lys Ala
                325                 330                 335

Gln Pro Val Ser Cys Phe Thr His Leu Val Gln Ala Asn Val Arg Asn
            340                 345                 350

Lys Lys Val Phe Lys Glu Ala Val Gln Gly Met Val Ala Lys Gly Thr
        355                 360                 365

Thr Gly Tyr Lys Ala Gly Phe Glu Tyr Ala Phe Asp Gln Leu Gln Asn
    370                 375                 380

Ser Asn Ile Thr Arg Ala Asn Cys Asn Lys Met Ile Met Met Phe Thr
385                 390                 395                 400

Asp Gly Gly Glu Asp Arg Val Gln Asp Val Phe Glu Lys Tyr Asn Trp
                405                 410                 415

Pro Asn Arg Thr Val Arg Val Phe Thr Phe Ser Val Gly Gln His Asn
            420                 425                 430

Tyr Asp Val Thr Pro Leu Gln Trp Met Ala Cys Ala Asn Lys Gly Tyr
        435                 440                 445

Tyr Phe Glu Ile Pro Ser Ile Gly Ala Ile Arg Ile Asn Thr Gln Glu
    450                 455                 460

Tyr Leu Asp Val Leu Gly Arg Pro Met Val Leu Ala Gly Lys Glu Ala
465                 470                 475                 480

Lys Gln Val Gln Trp Thr Asn Val Tyr Glu Asp Ala Leu Gly Leu Gly
                485                 490                 495

Leu Val Val Thr Gly Thr Leu Pro Val Phe Asn Leu Thr Gln Asp Gly
            500                 505                 510

Pro Gly Glu Lys Lys Asn Gln Leu Ile Leu Gly Val Met Gly Ile Asp
        515                 520                 525

Val Ala Leu Asn Asp Ile Lys Arg Leu Thr Pro Asn Tyr Thr Leu Gly
    530                 535                 540

Ala Asn Gly Tyr Val Phe Ala Ile Asp Leu Asn Gly Tyr Val Leu Leu
545                 550                 555                 560

His Pro Asn Leu Lys Pro Gln Thr Thr Asn Phe Arg Glu Pro Val Thr
                565                 570                 575
```

-continued

```
Leu Asp Phe Leu Asp Ala Glu Leu Glu Asp Glu Asn Lys Glu Glu Ile
            580                 585                 590

Arg Arg Ser Met Ile Asp Gly Asn Lys Gly His Lys Gln Ile Arg Thr
        595                 600                 605

Leu Val Lys Ser Leu Asp Glu Arg Tyr Ile Asp Glu Val Thr Arg Asn
    610                 615                 620

Tyr Thr Trp Val Pro Ile Arg Ser Thr Asn Tyr Ser Leu Gly Leu Val
625                 630                 635                 640

Leu Pro Pro Tyr Ser Thr Phe Tyr Leu Gln Ala Asn Leu Ser Asp Gln
                645                 650                 655

Ile Leu Gln Val Lys Tyr Phe Glu Phe Leu Leu Pro Ser Ser Phe Glu
            660                 665                 670

Ser Glu Gly His Val Phe Ile Ala Pro Arg Glu Tyr Cys Lys Asp Leu
        675                 680                 685

Asn Ala Ser Asp Asn Asn Thr Glu Phe Leu Lys Asn Phe Ile Glu Leu
    690                 695                 700

Met Glu Lys Val Thr Pro Asp Ser Lys Gln Cys Asn Asn Phe Leu Leu
705                 710                 715                 720

His Asn Leu Ile Leu Asp Thr Gly Ile Thr Gln Gln Leu Val Glu Arg
                725                 730                 735

Val Trp Arg Asp Gln Asp Leu Asn Thr Tyr Ser Leu Leu Ala Val Phe
            740                 745                 750

Ala Ala Thr Asp Gly Gly Ile Thr Arg Val Phe Pro Asn Lys Ala Ala
        755                 760                 765

Glu Asp Trp Thr Glu Asn Pro Glu Pro Phe Asn Ala Ser Phe Tyr Arg
    770                 775                 780

Arg Ser Leu Asp Asn His Gly Tyr Val Phe Lys Pro Pro His Gln Asp
785                 790                 795                 800

Ala Leu Leu Arg Pro Leu Glu Leu Glu Asn Asp Thr Val Gly Ile Leu
                805                 810                 815

Val Ser Thr Ala Val Glu Leu Ser Leu Gly Arg Arg Thr Leu Arg Pro
            820                 825                 830

Ala Val Val Gly Val Lys Leu Asp Leu Glu Ala Trp Ala Glu Lys Phe
        835                 840                 845

Lys Val Leu Ala Ser Asn Arg Thr His Gln Asp Gln Pro Gln Lys Cys
    850                 855                 860

Gly Pro Asn Ser His Cys Glu Met Asp Cys Glu Val Asn Asn Glu Asp
865                 870                 875                 880

Leu Leu Cys Val Leu Ile Asp Asp Gly Gly Phe Leu Val Leu Ser Asn
                885                 890                 895

Gln Asn His Gln Trp Asp Gln Val Gly Arg Phe Phe Ser Glu Val Asp
            900                 905                 910

Ala Asn Leu Met Leu Ala Leu Tyr Asn Asn Ser Phe Tyr Thr Arg Lys
        915                 920                 925

Glu Ser Tyr Asp Tyr Gln Ala Ala Cys Ala Pro Gln Pro Pro Gly Asn
    930                 935                 940

Leu Gly Ala Ala Pro Arg Gly Val Phe Val Pro Thr Val Ala Asp Phe
945                 950                 955                 960

Leu Asn Leu Ala Trp Trp Thr Ser Ala Ala Ala Trp Ser Leu Phe Gln
                965                 970                 975

Gln Leu Leu Tyr Gly Leu Ile Tyr His Ser Trp Phe Gln Ala Asp Pro
            980                 985                 990

Ala Glu Ala Glu Gly Ser Pro Glu Thr Arg Glu Ser Ser Cys Val Met
```

-continued

```
        995                 1000                1005

Lys Gln Thr Gln Tyr Tyr Phe Gly Ser Val Asn Ala Ser Tyr Asn Ala
   1010                1015                1020

Ile Ile Asp Cys Gly Asn Cys Ser Arg Leu Phe His Ala Gln Arg Leu
1025                1030                1035                1040

Thr Asn Thr Asn Leu Leu Phe Val Val Ala Glu Lys Pro Leu Cys Ser
               1045                1050                1055

Gln Cys Glu Ala Gly Arg Leu Leu Gln Lys Glu Thr His Cys Pro Ala
           1060                1065                1070

Asp Gly Pro Glu Gln Cys Glu Leu Val Gln Arg Pro Arg Tyr Arg Arg
       1075                1080                1085

Gly Pro His Ile Cys Phe Asp Tyr Asn Ala Thr Glu Asp Thr Ser Asp
   1090                1095                1100

Cys Gly Arg Gly Ala His His His His His His
1105                1110                1115


<210> SEQ ID NO 24
<211> LENGTH: 1077
<212> TYPE: PRT
<213> ORGANISM: Mus musculus

<400> SEQUENCE: 24

Met Ala Gly Pro Gly Ser Leu Cys Cys Ala Ser Arg Gly Ala Ser Ala
  1               5                  10                  15

Leu Leu Ala Thr Ala Leu Leu Tyr Ala Ala Leu Gly Asp Val Val Arg
             20                  25                  30

Ser Glu Gln Gln Ile Pro Leu Ser Val Val Lys Leu Trp Ala Ser Ala
        35                  40                  45

Phe Gly Gly Glu Ile Lys Ser Ile Ala Ala Lys Tyr Ser Gly Ser Gln
     50                  55                  60

Leu Leu Gln Lys Lys Tyr Lys Glu Tyr Glu Lys Asp Val Ala Ile Glu
 65                  70                  75                  80

Glu Ile Asp Gly Leu Gln Leu Val Lys Lys Leu Ala Lys Ile Met Glu
                 85                  90                  95

Glu Met Phe His Lys Lys Ser Glu Ala Val Arg Arg Leu Val Glu Ala
            100                 105                 110

Ala Glu Glu Ala His Leu Lys His Glu Phe Asp Ala Asp Leu Gln Tyr
        115                 120                 125

Glu Tyr Phe Asn Ala Val Leu Ile Asn Glu Arg Asp Lys Asp Gly Asn
    130                 135                 140

Phe Leu Glu Leu Gly Lys Glu Phe Ile Leu Ala Pro Asn Asp His Phe
145                 150                 155                 160

Asn Asn Leu Pro Val Asn Ile Ser Leu Ser Asp Val Gln Val Pro Thr
                165                 170                 175

Asn Met Tyr Asn Lys Asp Pro Ala Ile Val Asn Gly Val Tyr Trp Ser
            180                 185                 190

Glu Ser Leu Asn Lys Val Phe Val Asp Asn Phe Asp Arg Asp Pro Ser
        195                 200                 205

Leu Ile Trp Gln Tyr Phe Gly Ser Ala Lys Gly Phe Phe Arg Gln Tyr
    210                 215                 220

Pro Gly Ile Lys Trp Glu Pro Asp Glu Asn Gly Val Ile Ala Phe Asp
225                 230                 235                 240

Cys Arg Asn Arg Lys Trp Tyr Ile Gln Ala Ala Thr Ser Pro Lys Asp
                245                 250                 255
```

```
Val Val Ile Leu Val Asp Val Ser Gly Ser Met Lys Gly Leu Arg Leu
            260                 265                 270

Thr Ile Ala Lys Gln Thr Val Ser Ser Ile Leu Asp Thr Leu Gly Asp
        275                 280                 285

Asp Asp Phe Phe Asn Ile Ile Thr Tyr Asn Glu Glu Leu His Tyr Val
    290                 295                 300

Glu Pro Cys Leu Asn Gly Thr Leu Val Gln Ala Asp Arg Thr Asn Lys
305                 310                 315                 320

Glu His Phe Arg Glu His Leu Asp Lys Leu Phe Ala Lys Gly Ile Gly
                325                 330                 335

Met Leu Asp Ile Ala Leu Asn Glu Ala Phe Asn Ile Leu Ser Asp Phe
            340                 345                 350

Asn His Thr Gly Gln Gly Ser Ile Cys Ser Gln Ala Ile Met Leu Ile
        355                 360                 365

Thr Asp Gly Ala Val Asp Thr Tyr Asp Thr Ile Phe Ala Lys Tyr Asn
    370                 375                 380

Trp Pro Asp Arg Lys Val Arg Ile Phe Thr Tyr Leu Ile Gly Arg Glu
385                 390                 395                 400

Ala Ala Phe Ala Asp Asn Leu Lys Trp Met Ala Cys Ala Asn Lys Gly
                405                 410                 415

Phe Phe Thr Gln Ile Ser Thr Leu Ala Asp Val Gln Glu Asn Val Met
            420                 425                 430

Glu Tyr Leu His Val Leu Ser Arg Pro Lys Val Ile Asp Gln Glu His
        435                 440                 445

Asp Val Val Trp Thr Glu Ala Tyr Ile Asp Ser Thr Leu Pro Gln Ala
    450                 455                 460

Gln Lys Leu Ala Asp Asp Gln Gly Leu Val Leu Met Thr Thr Val Ala
465                 470                 475                 480

Met Pro Val Phe Ser Lys Gln Asn Glu Thr Arg Ser Lys Gly Ile Leu
                485                 490                 495

Leu Gly Val Val Gly Thr Asp Val Pro Val Lys Glu Leu Leu Lys Thr
            500                 505                 510

Ile Pro Lys Tyr Lys Leu Gly Ile His Gly Tyr Ala Phe Ala Ile Thr
        515                 520                 525

Asn Asn Gly Tyr Ile Leu Thr His Pro Glu Leu Arg Pro Leu Tyr Glu
    530                 535                 540

Glu Gly Lys Lys Arg Arg Lys Pro Asn Tyr Ser Ser Val Asp Leu Ser
545                 550                 555                 560

Glu Val Glu Trp Glu Asp Arg Asp Asp Val Leu Arg Asn Ala Met Val
                565                 570                 575

Asn Arg Lys Thr Gly Lys Phe Ser Met Glu Val Lys Lys Thr Val Asp
            580                 585                 590

Lys Gly Lys Arg Val Leu Val Met Thr Asn Asp Tyr Tyr Tyr Thr Asp
        595                 600                 605

Ile Lys Gly Thr Pro Phe Ser Leu Gly Val Ala Leu Ser Arg Gly His
    610                 615                 620

Gly Lys Tyr Phe Phe Arg Gly Asn Val Thr Ile Glu Glu Gly Leu His
625                 630                 635                 640

Asp Leu Glu His Pro Asp Val Ser Leu Ala Asp Glu Trp Ser Tyr Cys
                645                 650                 655

Asn Thr Asp Leu His Pro Glu His Arg His Leu Ser Gln Leu Glu Ala
            660                 665                 670

Ile Lys Leu Tyr Leu Lys Gly Lys Glu Pro Leu Leu Gln Cys Asp Lys
```

-continued

```
        675                 680                 685

Glu Leu Ile Gln Glu Val Leu Phe Asp Ala Val Val Ser Ala Pro Ile
    690                 695                 700

Glu Ala Tyr Trp Thr Ser Leu Ala Leu Asn Lys Ser Glu Asn Ser Asp
705                 710                 715                 720

Lys Gly Val Glu Val Ala Phe Leu Gly Thr Arg Thr Gly Leu Ser Arg
                725                 730                 735

Ile Asn Leu Phe Val Gly Ala Glu Gln Leu Thr Asn Gln Asp Phe Leu
            740                 745                 750

Lys Ala Gly Asp Lys Glu Asn Ile Phe Asn Ala Asp His Phe Pro Leu
        755                 760                 765

Trp Tyr Arg Arg Ala Ala Glu Gln Ile Ala Gly Ser Phe Val Tyr Ser
    770                 775                 780

Ile Pro Phe Ser Thr Gly Thr Val Asn Lys Ser Asn Val Val Thr Ala
785                 790                 795                 800

Ser Thr Ser Ile Gln Leu Leu Asp Glu Arg Lys Ser Pro Val Val Ala
                805                 810                 815

Ala Val Gly Ile Gln Met Lys Leu Glu Phe Phe Gln Arg Lys Phe Trp
            820                 825                 830

Thr Ala Ser Arg Gln Cys Ala Ser Leu Asp Gly Lys Cys Ser Ile Ser
        835                 840                 845

Cys Asp Asp Glu Thr Val Asn Cys Tyr Leu Ile Asp Asn Asn Gly Phe
    850                 855                 860

Ile Leu Val Ser Glu Asp Tyr Thr Gln Thr Gly Asp Phe Phe Gly Glu
865                 870                 875                 880

Val Glu Gly Ala Val Met Asn Lys Leu Leu Thr Met Gly Ser Phe Lys
                885                 890                 895

Arg Ile Thr Leu Tyr Asp Tyr Gln Ala Met Cys Arg Ala Asn Lys Glu
            900                 905                 910

Ser Ser Asp Ser Ala His Gly Leu Leu Asp Pro Tyr Lys Ala Phe Leu
        915                 920                 925

Ser Ala Ala Lys Trp Ile Met Thr Glu Leu Val Leu Phe Leu Val Glu
    930                 935                 940

Phe Asn Leu Cys Ser Trp Trp His Ser Asp Met Thr Ala Lys Ala Gln
945                 950                 955                 960

Lys Leu Lys Gln Thr Leu Glu Pro Cys Asp Thr Glu Tyr Pro Ala Phe
                965                 970                 975

Val Ser Glu Arg Thr Ile Lys Glu Thr Thr Gly Asn Ile Ala Cys Glu
            980                 985                 990

Asp Cys Ser Lys Ser Phe Val Ile Gln Gln Ile Pro Ser Ser Asn Leu
        995                 1000                1005

Phe Met Val Val Val Asp Ser Ser Cys Leu Cys Glu Ser Val Ala Pro
   1010                1015                1020

Ile Thr Met Ala Pro Ile Glu Ile Arg Tyr Asn Glu Ser Leu Lys Cys
1025               1030                1035                1040

Glu Arg Leu Lys Ala Gln Lys Ile Arg Arg Arg Pro Glu Ser Cys His
               1045                1050                1055

Gly Phe His Pro Glu Glu Asn Ala Arg Glu Cys Gly Gly Ala Ser His
           1060                1065                1070

His His His His His
       1075

<210> SEQ ID NO 25
```

-continued

```
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 25

tcgccaccat ggcggtgccg gctc                                        24


<210> SEQ ID NO 26
<211> LENGTH: 49
<212> TYPE: DNA
<213> ORGANISM: Artificial Sequence
<220> FEATURE:
<223> OTHER INFORMATION: Description of Artificial Sequence: primer

<400> SEQUENCE: 26

tcggaattcc tcagtgatgg tgatggtgat gggccccgcg gccacagtc             49


<210> SEQ ID NO 27
<211> LENGTH: 23
<212> TYPE: DNA
<213> ORGANISM: Artificial Sequence
<220> FEATURE:
<223> OTHER INFORMATION: Description of Artificial Sequence: primer

<400> SEQUENCE: 27

tcgccaccat ggccgggccg ggc                                         23


<210> SEQ ID NO 28
<211> LENGTH: 43
<212> TYPE: DNA
<213> ORGANISM: Artificial Sequence
<220> FEATURE:
<223> OTHER INFORMATION: Description of Artificial Sequence: primer

<400> SEQUENCE: 28

tctcagtgat ggtgatggtg atgcgatgca cccccacact ctc                   43
```